(12) United States Patent
Mallick et al.

(10) Patent No.: US 12,092,642 B2
(45) Date of Patent: Sep. 17, 2024

(54) SYSTEMS AND METHODS FOR BIOMOLECULE QUANTITATION

(71) Applicant: NAUTILUS SUBSIDIARY, INC., Seattle, WA (US)

(72) Inventors: Parag Mallick, San Mateo, CA (US); Jarrett D. Egertson, Rancho Palos Verdes, CA (US); Gregory Kapp, San Carlos, CA (US)

(73) Assignee: NAUTILUS SUBSIDIARY, INC., Seattle, WA (US)

( * ) Notice: Subject to any disclaimer, the term of this patent is extended or adjusted under 35 U.S.C. 154(b) by 0 days.

(21) Appl. No.: 17/579,576

(22) Filed: Jan. 19, 2022

(65) Prior Publication Data

US 2022/0236282 A1 Jul. 28, 2022

Related U.S. Application Data

(60) Provisional application No. 63/193,486, filed on May 26, 2021, provisional application No. 63/139,739, filed on Jan. 20, 2021.

(51) Int. Cl.
*G01N 33/543* (2006.01)
*G01N 33/68* (2006.01)

(52) U.S. Cl.
CPC .............................. *G01N 33/6845* (2013.01)

(58) Field of Classification Search
None
See application file for complete search history.

(56) References Cited

U.S. PATENT DOCUMENTS

| | | | |
|---|---|---|---|
| 7,306,904 B2 | 12/2007 | Landegren et al. | |
| 7,351,528 B2 | 4/2008 | Landegren | |
| 7,855,054 B2 | 12/2010 | Schneider et al. | |
| 7,964,356 B2 | 6/2011 | Zichi et al. | |
| 8,013,134 B2 | 9/2011 | Fredriksson | |
| 8,222,047 B2 | 7/2012 | Duffy et al. | |
| 8,236,574 B2 | 8/2012 | Duffy et al. | |
| 8,268,554 B2 | 9/2012 | Schallmeiner | |
| 8,404,830 B2 | 3/2013 | Zichi et al. | |
| 8,415,171 B2 | 4/2013 | Rissin et al. | |
| 8,945,830 B2 | 2/2015 | Heil et al. | |
| 8,975,026 B2 | 3/2015 | Zichi et al. | |
| 8,975,388 B2 | 3/2015 | Zichi et al. | |
| 9,163,056 B2 | 10/2015 | Rohloff et al. | |
| 9,395,359 B2 | 7/2016 | Walt et al. | |
| 9,404,919 B2 | 8/2016 | Schneider et al. | |
| 9,625,469 B2 | 4/2017 | Marcotte et al. | |
| 9,678,068 B2 | 6/2017 | Duffy et al. | |
| 9,777,315 B2 | 10/2017 | Fredriksson et al. | |
| 9,926,566 B2 | 3/2018 | Ochsner et al. | |
| 9,938,314 B2 | 4/2018 | Rohloff et al. | |
| 10,221,207 B2 | 3/2019 | Rohloff et al. | |
| 10,221,421 B2 | 3/2019 | Jarvis et al. | |
| 10,239,908 B2 | 3/2019 | Rohloff et al. | |
| 10,316,321 B2 | 6/2019 | Zichi et al. | |
| 10,392,621 B2 | 8/2019 | Ochsner et al. | |
| 10,473,654 B1 | 11/2019 | Mallick | |
| 10,545,153 B2 | 1/2020 | Marcotte et al. | |
| 11,203,612 B2 | 12/2021 | Gremyachinskiy et al. | |
| 2019/0145982 A1 | 5/2019 | Chee et al. | |
| 2020/0082914 A1 | 3/2020 | Patel et al. | |
| 2020/0286584 A9 | 9/2020 | Patel et al. | |
| 2020/0318101 A1 | 10/2020 | Mallick et al. | |
| 2020/0348307 A1 | 11/2020 | Beierle et al. | |
| 2020/0348308 A1 | 11/2020 | Chee et al. | |
| 2021/0239705 A1 | 8/2021 | Mallick | |
| 2021/0390705 A1 | 12/2021 | Egertson et al. | |

FOREIGN PATENT DOCUMENTS

| | | |
|---|---|---|
| EP | 1 491 894 A2 | 12/2004 |
| WO | WO 2019/236749 A2 | 12/2019 |
| WO | WO-2020106889 A1 | 5/2020 |
| WO | WO-2020223368 A1 | 11/2020 |
| WO | WO-2021087402 A1 | 5/2021 |

OTHER PUBLICATIONS

Nielsen et al (PNAS 100:9330-5) (Year: 2003).*
Nielsen, et al. "Multiplexed sandwich assays in microarray format", Journal of Immunological Methods, Elsevier Science Publishers B.V., Amsterdam, NL, vol. 290, No. 1-2, Jul. 1, 2002, pp. 107-120. DOI: 10.1016/J.JIM.2004.04.012.
Kim, et al. "Direct Profiling the Post-Translational Modification Codes of a Single Protein Immobilized on a Surface Using Cu-free Click Chemistry", ACS Central Science, vol. 4, No. 5, Apr. 18, 2018, pp. 614-623.DOI: 10.1021/acscentsci.8b00114.
Alfaro, et al. "The emerging landscape of single-molecule protein sequencing technologies", Nature Publishing Group US, New York, vol. 18, No. 6, Jun. 1, 2021, pp. 604-617.
International Search Report and Written Opinion issued Jul. 18, 2022 in PCT/US2022/013017.
Aebersold, R., et al. How many human proteoforms are there? Nat Chem Biol 14, 206-214 (2018).
Anderson & Anderson. The human plasma proteome: history, character, and diagnostic prospects. Molecular & cellular proteomics: MCP vol. 1,11 (2002): 845-67.
Chang, Jui Yoa. A novel Edman-type degradation: direct formation of the thiohydantoin ring in alkaline solution by reaction of Edman-type reagents with N-monomethyl amino acids. FEBS letters 91.1 (1978): 63-68.

(Continued)

*Primary Examiner* — Christopher M Gross

(74) *Attorney, Agent, or Firm* — Knobbe, Martens, Olson & Bear LLP

(57) ABSTRACT

Systems and methods for obtaining qualitative or quantitative measurements of proteoforms of polypeptides are described. The described methods include measurements of affinity reagent binding on single-molecule polypeptide arrays to distinguish between polypeptide isoforms. The described methods may provide high resolution quantitative comparisons of proteoforms with very low copy numbers.

17 Claims, 21 Drawing Sheets

(56) References Cited

OTHER PUBLICATIONS

Egertson et al. A theoretical framework for proteome-scale single-molecule protein identification using multi-affinity protein binding reagents. BioRxiv (2021), DOI: 10.1101/2021.10.11.463967.

Ho, et al. Unification of Protein Abundance Datasets Yields a Quantitative *Saccharomyces cerevisiae* Proteome. Cell systems vol. 6,2 (2018): 192-205.e3. doi: 10.1016/j.cels.2017.12.004.

Smith, Lloyd M. et al. Proteoform: a single term describing protein complexity. Nature methods vol. 10,3 (2013): 186-7. doi:10.1038/nmeth.2369.

Swaminathan, J. et al. Highly parallel single-molecule identification of proteins in zeptomole-scale mixtures. Nat Biotechnol 36, 1076-1082 (2018). https://doi.org/10.1038/nbt.4278.

Walker, J M. The dansyl method for identifying N-terminal amino acids. Methods in molecular biology (Clifton, N.J.) vol. 1 (1984): 203-12. doi:10.1385/0-89603-062-8:203.

Winiewski, Jacek et al. A Proteomic Ruler for Protein Copy Number and Concentration Estimation without Spike-in Standards. Molecular & cellular proteomics. Molecular & Cellular Proteomics 13:10. 1074 (2014).

\* cited by examiner

SYSTEMS AND METHODS FOR BIOMOLECULE QUANTITATION

CROSS REFERENCE

This application claims priority to U.S. Provisional Application No. 63/193,486, filed on May 26, 2021, and U.S. Provisional Application No. 63/139,739, filed on Jan. 20, 2021, each of which is incorporated herein in its entirety by reference.

BACKGROUND OF THE INVENTION

Proteomics is the study of proteins and protein interactions in or from biological systems. Proteomics may include the study of proteins and protein systems at any protein scale from the sub-molecular level to the organismal level. Proteomics may include the study of the interactions between the proteome and other system such as, for example, interactions between a proteome and genome or interactions between a proteome and transcriptome. A proteome may include thousands of polypeptides with unique biological roles. A polypeptide encoded by a single gene may have multiple variants or proteoforms depending upon certain pre-translational or post-translational processes that occur within a biological system. Quantitation of particular proteoforms at the level of single species, polypeptide families, proteomes, microbiomes, or biomes can provide important information on biological systems, including diagnostic markers for certain disease states.

SUMMARY OF THE INVENTION

The present disclosure provides a method of characterizing proteoforms of a polypeptide. The method can include steps of (a) providing an array having a plurality of polypeptides, wherein the plurality of polypeptides includes a first proteoform of a polypeptide and a second proteoform of the polypeptide, and wherein each proteoform of the polypeptide is present at an individually observable address on the array; (b) contacting the array with a first affinity reagent and a second affinity reagent, wherein the first affinity reagent binds to the first proteoform and the second affinity reagent binds to the second proteoform, and wherein at least one of the first and second affinity reagents binds promiscuously to the first and second proteoforms of the polypeptide; and (c) detecting the presence or absence of binding of the affinity reagents at the individually observable addresses on the array, thereby characterizing at least one of the proteoforms of the polypeptide.

In an aspect, described herein is a method, comprising: a) providing an array of polypeptides, wherein the array of polypeptides comprises a first proteoform of a polypeptide and a second proteoform of the polypeptide, and wherein each polypeptide of the array of polypeptides is present at an individually observable address of the array; b) contacting the array of polypeptides with a first affinity reagent, wherein the first affinity reagent has a first characterized binding affinity, wherein the first affinity reagent comprises a first detectable label that is configured to transmit a first detectable signal; c) detecting a presence or absence of the first detectable signal at each observable address on the solid support; d) contacting the array of polypeptides with a second affinity reagent, wherein the second affinity reagent has a second characterized binding affinity, wherein the second affinity reagent comprises a second detectable label that is configured to transmit a second detectable signal; e) detecting a presence or absence of the second detectable signal at each observable address on the solid support; and f) characterizing presence or absence of the first proteoform and the second proteoform at each address of the array based upon the first characterized binding affinity of the first affinity reagent and the second characterized binding affinity of the second affinity reagent.

In some embodiments, each address of the array comprises a single coupled polypeptide. In some embodiments, each address of the array comprises more than one coupled polypeptide.

In some embodiments, the first proteoform or the second proteoform is a post-translational modification (PTM) isoform of the polypeptide. In some embodiments, the PTM is selected from the groups consisting of glycosylation, methylation, phosphorylation, acetylation, ubiquitination, formylation, pyroglutamyl, alkylation, acylation, and nitrosylation. In some embodiments, the first proteoform or the second proteoform is a splicing isoform of the polypeptide.

In some embodiments, the first characterized binding affinity comprises a higher probability of binding to the first proteoform compared to the probability of binding to the second proteoform. In some embodiments, the second characterized binding affinity comprises a lower probability of binding to the first proteoform compared to the probability of binding to the second proteoform.

In some embodiments, the characterizing the presence or absence of the first proteoform and the second proteoform at each observable address of the array comprises: i) providing the presence or absence of the first detectable signal at each address of the array and the presence or absence of the second detectable signal at each address of the array to a computer-implemented decoding algorithm; and ii) determining a characterization of polypeptide identity at each address of the array using the decoding algorithm, wherein the characterization of polypeptide identity is selected from the group consisting of the first proteoform, the second proteoform, both proteoforms, neither proteoform, and uncertain. In some embodiments, the determining a characterization of polypeptide identity further comprises determining a confidence interval for the characterization of polypeptide identity.

In some embodiments, one or more of steps b)-e) are repeated. In some embodiments, the method further comprises contacting the array with one or more additional affinity reagents comprising a characterized binding affinity.

In some embodiments, the method further comprises removing the first affinity reagent from the array. In some embodiments, the method further comprises removing the second affinity reagent from the array.

In some embodiments, the method further comprises calculating a quantity of the first proteoform or a quantity of the second proteoform in the array of polypeptides. In some embodiments, the polypeptide species has one or more additional proteoforms. In some embodiments, the array of polypeptides comprises one or more additional (of the same or different) polypeptide species. In some embodiments, at least one polypeptide species of the one or more additional polypeptide species comprises two or more proteoforms.

In some embodiments, steps b) through f) are repeated for the at least one polypeptide species. In some embodiments, steps b) through f) are repeated for each polypeptide species comprising two or more proteoforms. In some embodiments, the one or more additional polypeptide species comprises at least about 10 polypeptide species. In some embodiments, the one or more additional polypeptide species comprises at least about 100 polypeptide species. In some embodiments, the one or more additional polypeptide species comprises at least about 1000 polypeptide species.

In some embodiments, the polypeptides of the array of polypeptides are derived from a proteomic sample. In some embodiments, the proteomic sample comprises a sample derived from a human, domesticated animal, wild animal, domesticated plant, wild plant, engineered microorganism, or natural microorganism.

In some embodiments, the first affinity reagent or the second affinity reagent comprises a characterized binding affinity for a PTM. In some embodiments, the characterized binding affinity comprises a binding affinity for the PTM that is independent of sequence context. In some embodiments, the characterized binding affinity comprises a binding affinity for the PTM that is dependent upon sequence context.

In some embodiments, the first detectable label or the second detectable label is selected from the group consisting of a fluorescent label, a luminescent label, a radiolabel, an isotopic label, and a nucleic acid label. In some embodiments, the first detectable label is the same as the second detectable label. In some embodiments, the first detectable label is different from the second detectable label. In some embodiments, a first detectable label or a second detectable label may be selected from the group consisting of one or more fluorescent labels, intramolecular fluorescent FRET systems, intramolecular time-resolved FRET systems, FRET cassette systems, intramolecular fluorescent-quencher systems, and dyes which are only fluorescent with restricted intramolecular rotation.

In certain embodiments, detection methods include fluorescence lifetime (FLT), two photon excitation (TPE), surface plasmon resonance (SPR), fluorescence polarization (FP) and evanescent methods, such as total internal reflection (TIRF) microscopy, or used in single or array wells, for example, in zero mode waveguides (ZMW). These methods may be used exclusively or combined with other detection described herein and they may be used in single-molecule array format.

In some embodiments, the array comprises a solid support and each polypeptide of the array is coupled to an address on the solid support. In some embodiments, the solid support comprises a metal, metal oxide, semiconductor, polymer, glass, or ceramic. In some embodiments, the solid support comprises a patterned array. In some embodiments, the solid support comprises a non-patterned array. In some embodiments, the solid support may comprise one or more differentially soluble polymers (for example, polyethyleneglycol, or PEG polymers) which are differentially soluble in different solvents or buffers. Polymers that are soluble in aqueous solvents and insoluble in particular non-aqueous solvents can be particularly useful. Advantages of differentially soluble polymers include ease of separation of PEG polymers from reagents by precipitation of the PEG polymer followed by simple filtration to remove chemical reagents or other unwanted species which remain in solution. The PEG polymers may be barcoded with small molecule or oligo nucleic acids unique molecular tag.

In some embodiments, each observable address comprises an anchoring group coupled to the array. In some embodiments, each polypeptide of the array of polypeptides is coupled to the solid support by the anchoring group. In some embodiments, an anchoring group comprises a single polypeptide of the array of polypeptides. In some embodiments, an anchoring group comprises two or more polypeptides of the array of polypeptides.

In some embodiments, the anchoring group comprises a structured nucleic acid particle. In some embodiments, the structured nucleic acid particle comprises a DNA nanoball, a DNA nanotube, or a DNA origami particle.

In another aspect, described herein is a method, comprising: a) performing the method of any one of the above-described embodiments; and b) quantifying proteoforms for at least about 10% of a proteome.

In some embodiments, the quantifying comprises quantifying at least about 50% of a proteome. In some embodiments, the quantifying comprises quantifying at least about 90% of a proteome.

In some embodiments, the polypeptide comprises a polypeptide complex, wherein the polypeptide complex comprises the polypeptide and a second biomolecule (the first biomolecule comprising the polypeptide). In some embodiments, the second biomolecule comprises a second polypeptide, a nucleic acid, a polysaccharide, or a lipid, monomeric nucleotide, monomeric amino acid, metabolite or small molecule.

In some embodiments, the polypeptides of the array of polypeptides are derived from a non-biological source. In some embodiments, the non-biological source comprises a forensic sample, an industrial sample, a consumer product, a geological sample, an archeological sample, a paleontological sample, and an extraterrestrial sample. In some embodiments, the polypeptides of the array of polypeptides are derived from a population of organisms or a microbiome.

In other embodiments a protein characterization method may comprise characterizing proteoforms of a polypeptide by providing a plurality of the proteoforms of a polypeptide at a plurality of sites in an array. The plurality of proteoforms may be contacted with a first set of affinity reagents, each affinity reagent comprising a detectable label, wherein at least one affinity reagent binds independently to two or more different proteoforms of the polypeptide, and wherein at least one proteoform of the polypeptide binds to two or more different affinity reagents of the first set of affinity reagents. The presence or absence of binding reporter signals from the detectable labels may be detected and the first set of affinity reagents from the proteoforms removed. The steps for the first set of affinity reagents may be repeated with a second set of affinity reagents and the binding reporter signals analyzed thereby at least one of the proteoforms in the array may be characterized.

The present disclosure further provides a method, including steps of generally (a) providing an array including a plurality of polypeptides, wherein the plurality of polypeptides includes a first polypeptide having a first proteoform and a second polypeptide having a second proteoform, and wherein a polypeptide of the plurality of polypeptides is present at an individually observable address of the array; (b) contacting the array with a first affinity reagent and a second affinity reagent, wherein the first affinity reagent is configured to bind to the first proteoform and the second affinity reagent is configured to bind to the second proteoform; (c) detecting signals indicative of the first affinity reagent binding to the first polypeptide and the second affinity reagent binding to the second polypeptide; and (d) using the signals to characterize the first proteoform and the second proteoform.

Optionally, the method can further include (i) contacting an array with a first affinity reagent; (ii) detecting a first signal indicative of the first affinity reagent binding to the first polypeptide; (iii) subsequently contacting the array with a second affinity reagent; and (iv) detecting a second signal indicative of the second affinity reagent binding to the second polypeptide, wherein the signals comprise the first signal and the second signals.

Alternatively, or additionally, the method can further include: (i) contemporaneously contacting the array with a first affinity reagent and a second affinity reagent; (ii) detecting a first signal indicative of the first affinity reagent binding to the first polypeptide; and (iii) detecting a second signal indicative of the second affinity reagent binding to the second polypeptide, wherein the signals comprise the first signal and the second signals. In some cases, a first polypeptide having a first proteoform may be derived from the same gene as a second polypeptide having a second proteoform. That is, first and second polypeptides comprising corresponding first and second proteoforms may be related to each other by originating from a common gene. In some cases, a first polypeptide having a first proteoform may not be derived from the same gene as a second polypeptide having a second proteoform (they may not be related to each other).

In some embodiments proteoforms of a polypeptide, may be characterized by providing an array comprising a plurality of polypeptides, wherein the plurality of polypeptides includes a first polypeptide having a first proteoform and a second polypeptide having a second proteoform, and wherein each polypeptide of the plurality of polypeptides is present at an individually observable address on the array. The array may be contacted with a first affinity reagent and a second affinity reagent, wherein the first affinity reagent binds to the first proteoform and the second affinity reagent binds to the second proteoform, wherein at least one of the first and second affinity reagents binds independently to two or more different proteoforms of the polypeptide, and wherein at least one proteoform of the polypeptide binds independently to at least the first affinity reagent and the second affinity reagent. The presence or absence of binding of the affinity reagents to the polypeptides may be detected and characterization of at least one of the proteoforms of a polypeptide in the array may be performed using unique computer methods to differentiate between the proteoforms. The first and second affinity reagents may include a detectable label for detecting the presence or absence of binding reporter signals from the detectable labels. Analyzing the binding reporter signals may characterize at least one of the proteoforms of a polypeptide in the array.

In some embodiments, proteoform characterization may include Edman-type sequencing steps, where the N-terminal regions may be probed with affinity reagents before removal of an N-terminal residue by the Edman process or equivalent process. Affinity reagents may be used to form specific affinity complexes which include an initial Edman N-terminal complex (prior to N-terminal cleavage). Affinity reagents may be used both before and after Edman complex formation. Edman complexes may include one the Edman moiety, fluorescent chemical groups, biotin, linkers, photoactive groups, groups which affect water solubilities, hydrophobic groups, reporter groups, click chemistry groups, and the like. Edman groups may be configured to be removed under acidic, basic or neutral conditions with a variety of known chemical reagents.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
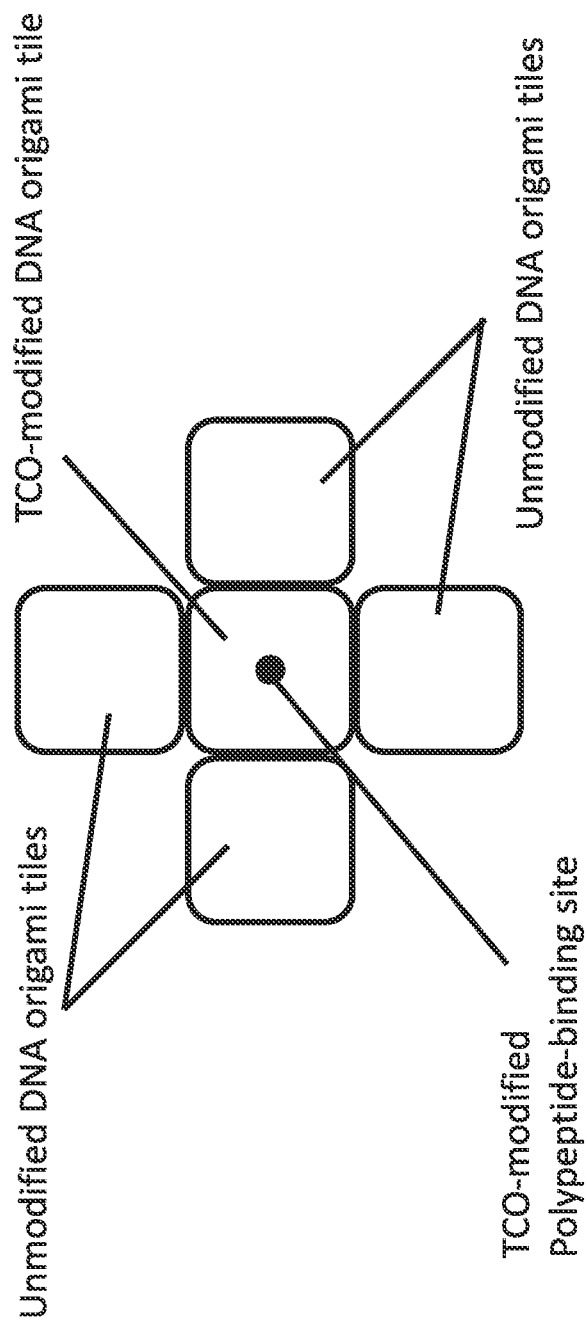
FIG. 1 illustrates a schematic of a DNA-origami tile configured to couple a polypeptide to a solid support, in accordance with some embodiments.

The complexity of a proteome or biological system may derive not only from the diversity of polypeptide sequences within the proteome or biological system, but also from the numerous proteoforms of many polypeptides. While a genome may include thousands, or even tens of thousands of unique genes, the number of distinct polypeptide or protein isoforms (i.e. proteoforms) within a proteome or biological system may number into the millions. In some cases, the presence or relative abundance of differing proteoforms of one or more genes may provide important information about the function of biological systems. In a clinical setting, the presence or relative abundance of differing proteoforms of one or more genes may serve as a diagnostic or prognostic marker of a disease state or a health state. As an example, the EGFR protein is an important biomarker with numerous known proteoforms. Alternative splicing proteoforms of EGFR protein have been implicated as a possible cause or biomarker for several forms of cancer, including certain lung, brain, and skin cancers.

In a complex system, such as a proteome (e.g., the human proteome) or a microbiome, the accurate quantitation of proteoforms provides a substantially deeper source of information than simple genomic or transcriptomic analyses. However, to fully understand the mechanisms underlying proteoform production and resulting system effects, it is important to have proteomic analyses that can provide quantitative measures of proteoform abundances with a wide dynamic range. In a complex proteome or system (e.g., the human proteome), there may be upwards of 9 or 10 orders of magnitude in difference between the most abundant proteins and the least abundant proteins. Quantitation of proteoform abundances becomes a challenge at both the high and low concentration ranges of polypeptide abundance. For example, in a traditional proteomic technique such as mass spectrometry, low abundance polypeptides can be difficult to observe and/or quantitate, especially when attempting to distinguish individual proteoforms. At high abundance of a particular polypeptide species, it may be difficult to distinguish small amounts of rare or low abundance proteoforms within the signal of high abundance proteoforms.

Described herein are systems and methods for detecting polypeptide proteoforms utilizing single-molecule polypeptide arrays. In particular configurations of the systems and methods, different proteoforms can be distinguished from each other even when the proteoforms are expressed from the same gene. Optionally, polypeptide proteoforms can be quantified using the systems and methods set forth herein. The single-molecule polypeptide arrays can be contacted with multiple differing affinity reagents that are permitted to bind with polypeptides on the polypeptide array and observations of the presence or absence of binding can be performed for each polypeptide on the polypeptide array. Information on the presence or absence of binding for each polypeptide on the polypeptide array may be provided to a decoding algorithm that infers the identity of each polypeptide on the polypeptide array. The systems and methods described herein may permit the identification or quantification of particular polypeptide species within a complex mixture of polypeptides, as well as the identification or quantification of individual polypeptide proteoforms of the particular polypeptide species.

Definitions

As used herein, the term "polypeptide" refers to a molecule including two or more amino acids joined by a peptide bond. A polypeptide may also be referred to as a "protein," "oligopeptide" or "peptide". Although the terms "protein," "polypeptide," "oligopeptide" and "peptide" may optionally be used when distinguishing molecules having different characteristics, such as amino acid sequence length, molecular weight, origin of the molecule or the like, the terms are not intended to inherently delineate such distinctions in all contexts. A polypeptide may be a naturally occurring molecule, an artificial or synthetic molecule, or a molecule with a combination of both natural and unnatural chemical components. A polypeptide may include or exclude small molecule cofactors, metal ions or any other molecular, ionic or polymeric moieties. A polypeptide may have a quaternary structure that includes a covalent or non-covalent complex between two or more amino acid chains. A polypeptide may include or exclude one or more non-natural, chemically or otherwise modified amino acids, or non-amino acid moieties. A polypeptide may be modified naturally or synthetically, such as by PTMs. Whereas most naturally occurring proteins include L-amino acids, polypeptides described herein may include or exclude one or more D-amino acids or one or more mixtures including both D- or L- in any proportion, including racemic mixtures of D- and L-amino acids.

A polypeptide may be an enzyme or an enzyme associated with a covalent substrate (for example, with a covalent suicide inhibitor in its active site). A polypeptide may include one or more biotinylated or fluorescently labeled polypeptides which may be present as one or more amino acid side chain modifications, N- or C-terminus modifications, or as modifications of the amide backbone of the polypeptide. As described herein, a polypeptide may include one or more chemical linking groups or spacers between any two amino acid residues in a given polypeptide, for example, polypeptides may include polyethyleneglycol or polyimine linking groups at their termini or anywhere within the body of the polypeptide. A polypeptide may also include one or more chemical linking groups between, amino acid side chains, amino or carboxy termini, or anywhere on the polyamide backbone. For example, in the polypeptide H-Tyr-Lys-Ala-Cys-Pro-OH, a polyethylene glycol, oligoethylene glycol or a single ethylene glycol linker may span between the N-terminal amino group on the Tyr residue and the Cys side-chain thiol group, for example, as a way to form a cyclized polypeptide.

A polypeptide as described herein may include isotopically enriched elements, for example, wherein one or more of the amino acids is naturally or artificially enriched with $^{15}N$, $^{2}H$, $^{13}C$, or $^{34}S$ stable isotopes. Polypeptides as described herein may include radioactive isotopically enriched elements, for example, wherein one or more of the polypeptide's nitrogen atoms is enriched with $^{3}H$, $^{14}C$, $^{32}P$ or $^{35}S$ radioactive or unstable isotopes. A polypeptide may be attached to one or more oligonucleotides, for example, as barcodes.

As used herein, the term "proteoform," when used in reference to a polypeptide encoded by a gene, refers to a molecular form of the polypeptide. Variant molecular forms of the polypeptide are different proteoforms of the polypeptide. Proteoforms can differ, for example, due to presence, absence or relative arrangement of different regions of amino acid sequence (e.g., splicing variants, or protein processing variants), or due to presence or absence of different moieties on particular amino acids (e.g., post-translationally modified variants). Proteoforms can optionally differ due to a genetic variation, such as a single nucleotide polymorphism, deletion, insertion or mutation, or due to an errors in translation of mRNA to protein. A particular proteoform can be derived from an in vivo process, in vitro process, natural process or synthetic process. Differing proteoforms may be derived from within a single cell or a single organism. Differing proteoforms may be derived from different sources such as differing biological fluids, cells or tissues, provided the different sources include the same gene(s) that give(s) rise to the proteoforms or isoforms. Different proteoforms can also occur for polypeptides that have the same amino acid sequence whether or not the polypeptides are expressed by a gene. For example, variants of a particular polypeptide sequence can differ with respect to presence or absence of different moieties on particular amino acids. The term "proteoform" is intended to be used consistently with Smith et al., Proteoform: a single term describing protein complexity. *Nat. Methods*, 10:186-187 (2013), which is incorporated herein by reference. Accordingly, the term can be used to designate all of the different molecular forms in which the polypeptide product of a single gene can be found including changes due to genetic variations, alternatively spliced RNA transcripts and post-translational modifications (PTMs). This includes all PTMs classified by the PSI-MOD ontology. It follows that all proteoforms are polypeptides but not all polypeptides are proteoforms. The term "isoform," when used in reference to a polypeptide, is intended to be synonymous with the term "proteoform."

As used herein, the term "post translational modification" refers to a change to the chemical composition of a polypeptide compared to the chemical composition encoded by the gene for the polypeptide. Exemplary changes include those that alter the presence, absence or relative arrangement of different regions of amino acid sequence (e.g., splicing variants, or protein processing variants), or due to presence or absence of different moieties on particular amino acids (e.g., post-translationally modified variants). A post translational modification can be derived from an in vivo process or in vitro process. A post translational modification can be derived from a natural process or a synthetic process. Exemplary post translational modifications include those classified by the PSI-MOD ontology. See Smith et al., Proteoform: a single term describing protein complexity. Nat. Methods, 10:186-187 (2013).

As used herein, the term "functionalized," when used in reference to a material or substance, refers to a form of the material or substance that has been modified to include a moiety or functional group that was not present prior to the modification. A functionalized material or substance may be naturally or synthetically functionalized. For example, a polypeptide can be naturally functionalized with a phosphate group, an oligosaccharide group (e.g., glycosyl, glycosylphosphatidylinositol or phosphoglycosyl), nitrosyl, methyl, acetyl, formyl, pyroglutamyl, alkyl, acyl, lipid (e.g., glycosyl phosphatidylinositol, myristoyl or prenyl), ubiquitin or other naturally occurring PTM. A material or substance that is derived from a natural source can be functionalized to include an exogenous moiety that is not found in the material or substance in its native milieu. A functionalized material or substance may be functionalized for any given purpose, including altering chemical properties (e.g., altering hydrophobicity or changing surface charge density) or altering reactivity (e.g. capable of reacting with a moiety or reagent to form a covalent bond to the moiety or reagent).

As used herein, the term "reactive handle" refers to a pendant, reactive functional group (e.g., activated ester, azide or click reagent) that is attached to a material or substance. A reactive handle may be covalently or non-covalently attached to a material or substance.

As used herein, the term "anchoring group" refers to a moiety, molecule or particle that serves as an intermediary entity when attaching a polypeptide to a surface (e.g., where the surface is a solid support or a microbead). An anchoring group may be covalently or non-covalently attached to a surface and/or a polypeptide. An anchoring group may include one or any combination of a biomolecule, polymer, particle, nanoparticle, or any other entity that is capable of attaching to a surface or polypeptide. In some cases, an anchoring group may be a structured nucleic acid particle.

As used herein, the term "structured nucleic acid particle" (or "SNAP") refers to a single- or multi-chain polynucleotide molecule having a compacted three-dimensional structure. The compacted three-dimensional structure can optionally be characterized in terms of hydrodynamic radius or Stoke's radius of the SNAP relative to a random coil or other non-structured state for a nucleic acid having the same sequence length as the SNAP. The compacted three-dimensional structure can optionally have a characteristic tertiary structure. For example, a SNAP can be configured to have an increased number of internal binding interactions between regions of a polynucleotide strand, less distance between the regions, increased number of bends in the strand, and/or more acute bends in the strand, as compared to the same nucleic acid molecule in a random coil or other non-structured state. Alternatively, or additionally, the compacted three-dimensional structure can optionally have a characteristic quaternary structure. For example, a SNAP can be configured to have an increased number of interactions between polynucleotide strands or less distance between the strands, as compared to the same nucleic acid molecule in a random coil or other non-structured state. In some configurations, the secondary structure (i.e., the helical twist or direction of the polynucleotide strand) of a SNAP can be configured to be denser than the same nucleic acid molecule in a random coil or other non-structured state. SNAPs may include deoxyribonucleic acid (DNA), ribonucleic acid (RNA), peptide nucleic acid (PNA), and combinations thereof. SNAPs may have naturally-arising or engineered secondary, tertiary, or quaternary structures. Exemplary SNAPs may include nucleic acid nanoballs (e.g. DNA nanoballs, RCA products), nucleic acid nanotubes (e.g. DNA nanotubes), and nucleic acid origami (e.g. DNA origami). A SNAP may be functionalized to include one or more reactive handles or other moieties. Exemplary SNAPs include, for example, nucleic acid origami and nucleic acid nanoballs.

As used herein, the term "nucleic acid origami" refers to a nucleic acid construct having an engineered tertiary or quaternary structure. A nucleic acid origami may include DNA, RNA, PNA, modified or non-natural nucleic acids, or combinations thereof. A nucleic acid origami may include a plurality of oligonucleotides that hybridize via sequence complementarity to produce the engineered structuring of the origami. A nucleic acid origami may include sections of single-stranded or double-stranded nucleic acid, or combinations thereof. Exemplary nucleic acid origami structures may include nanotubes, nanowires, cages, tiles, nanospheres, blocks, and combinations thereof. A nucleic acid origami can optionally include a relatively long scaffold nucleic acid to which multiple smaller nucleic acids hybridize, thereby creating folds and bends in the scaffold that produce an engineered structure. The scaffold nucleic acid can be circular or linear. The scaffold nucleic acid can be single-stranded but for hybridization to the smaller nucleic acids. A smaller nucleic acid (sometimes referred to as a "staple") can hybridize to two regions of the scaffold, wherein the two regions of the scaffold are separated by an intervening region that does not hybridize to the smaller nucleic acid.

As used herein, the term "polypeptide composite" refers to a molecule that is formed by the coupling of a polypeptide to one or more anchoring groups. The coupling between molecules in a polypeptide composite may be covalent or non-covalent. For example, a polypeptide composite may be covalently linked by a covalent bond between a reactive handle on a polypeptide with a reactive handle on an anchoring group. In another example, a polypeptide composite may be non-covalently linked by an interaction such as hybridization between complementary oligonucleotides or a receptor-ligand linkage such as a streptavidin-biotin linkage.

As used herein, the term "species" refers to a molecule with a unique, distinguishable chemical structure. As used herein, the term "polypeptide species" refers to a polypeptide with a unique, distinguishable sequence of genetically encoded amino acids. The sequence of genetically encoded amino acids of a polypeptide is known as the primary structure of the polypeptide. Two polypeptides are considered to be of the same species if they possess the same primary structure. Polypeptide proteoforms (or isoforms) are distinguishable forms of the same polypeptide species. In another example, members of an "anchoring group species" have a unique, distinguishable structure that is common to the members. Anchoring group species may be identified, for example, by common shape, molecular structure, number of coupling sites, or type of coupling sites.

As used herein, the term "click reaction" or "biorthogonal reaction" may refer to a single-step, thermodynamically-favorable conjugation reaction utilizing biocompatible reagents. A click reaction may utilize no toxic or biologically incompatible reagents (e.g., acids, bases, heavy metals) or generate no toxic or biologically incompatible byproducts. A click reaction may utilize an aqueous solvent or buffer (e.g., phosphate buffer solution, Tris buffer, saline buffer, MOPS, etc.). For example, a click reaction may be thermodynamically favorable if it has a negative Gibbs free energy of reaction, for example a Gibbs free energy of reaction of less than about −5 kiloJoules/mole (kJ/mol), −10 kJ/mol, −25 kJ/mol, −50 kJ/mol, −100 kJ/mol, −200 kJ/mol, −300 kJ/mol, −400 kJ/mol, or less. Exemplary bioorthogonal and click reactions are described in detail in WO 2019/195633A1, which is herein incorporated by reference in its entirety. Exemplary click reactions may include metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2] cycloaddition, [4+1] cycloaddition, nucleophilic substitution, dihydroxylation, thiol-yne reaction, photoclick, nitrone dipole cycloaddition, norbornene cycloaddition, oxanorbornadiene cycloaddition, tetrazine ligation, and tetrazole photoclick reactions. Exemplary functional groups or reactive handles utilized to perform click reactions may include alkenes, alkynes, azides, allenes, epoxides, amines, thiols, nitrones, isonitriles, isocyanides, aziridines, activated esters, and tetrazines. Other well-known click conjugation reactions may be used having complementary biorthogonal reaction species, for example, where a first click component includes a hydrazine moiety and a second click component includes an aldehyde or ketone group and where the product of such a reaction includes a hydrazone functional group or equivalent.

As used herein, the term "array" refers to a population of molecules that are attached to one or more solid supports such that the molecules at one address can be distinguished from molecules at other addresses. An array can include different molecules that are each located at different addresses on a solid support. Alternatively, an array can include separate solid supports each functioning as an address that bears a different molecule, wherein the different molecules can be identified according to the locations of the solid supports on a surface to which the solid supports are attached, or according to the locations of the solid supports in a liquid such as a fluid stream. The molecules of the array can be, for example, nucleic acids such as SNAPs, polypeptides, proteins, peptides, oligopeptides, enzymes, ligands, or receptors such as antibodies, functional fragments of antibodies or aptamers. The addresses of an array can optionally be optically observable and, in some configurations, adjacent addresses can be optically distinguishable when detected using a method or apparatus set forth herein.

As used herein, the term "address," when used in reference to an array, means a location in an array where a particular molecule or molecules are present. An address may include a resolvable address. A resolvable address may be a location within the array that is uniquely identifiable by a physical detection mechanism, such as optical detection, electrical detection, or magnetic detection. An address can contain only a single molecule, or it can contain a population of several molecules of the same species (i.e. an ensemble of the molecules). Alternatively, an address can include a population of molecules that are different species. Addresses of an array are typically discrete. The discrete addresses can be contiguous, or they can have interstitial spaces between each other. An array useful herein can have, for example, addresses that are separated by less than 100 microns, 50 microns, 10 microns, 5 microns, 1 micron, or 0.5 micron. Alternatively, or additionally, an array can have addresses that are separated by at least 0.5 micron, 1 micron, 5 microns, 10 microns, 50 microns or 100 microns. The addresses can each have an area of less than 1 square millimeter, 500 square microns, 100 square microns, 25 square microns, 1 square micron or less. An address may be denoted and distinguished from other address by using molecular barcodes, for example, using DNA or amino-acids or both as molecular barcodes.

As used herein, the term "solid support" refers to a substrate that is insoluble in aqueous liquid. The substrate can be non-porous or porous. The solid support can optionally be rigid, gelatinous or otherwise insoluble in an aqueous liquid. The substrate can optionally be capable of taking up a liquid (e.g., due to porosity). As a further option, the substrate can be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor™, silica or silica-based materials including silicon and modified silicon, carbon, metals, inorganic glasses, optical fiber bundles, gels (e.g., hydrogels), and polymers.

As used herein, the terms "group" and "moiety" are intended to be synonymous when used in reference to the structure of a molecule. The terms refer to a component or part of the molecule. The terms do not necessarily denote the relative size of the component or part compared to the molecule, unless indicated otherwise. The terms do not necessarily denote the relative size of the component or part compared to any other component or part of the molecule, unless indicated otherwise. A group or moiety can contain one or more atom.

As used herein, the term "affinity reagent" refers to a molecule or other substance that is capable of specifically or reproducibly binding to an analyte (e.g. polypeptide or proteoform) or moiety (e.g. post-translational modification of a polypeptide). Binding can optionally be used to identify, track, capture, alter, or influence the binding partner. The binding partner can optionally be larger than, smaller than or the same size as the affinity reagent. An affinity reagent may form a reversible or irreversible interaction with a binding partner. An affinity reagent may bind with a binding partner in a covalent or non-covalent manner. An affinity reagent may be configured to perform a chemical modification (e.g., ligation, cleavage, concatenation, etc.) that produces a detectable change in the larger molecule, thereby permitting observation of the interaction that occurred. Affinity reagents may include reactive affinity reagents (e.g., kinases, ligases, proteases, nucleases, etc.) and non-reactive affinity reagents (e.g., antibodies, antibody fragments, aptamers, DARPins, peptamers, etc.). An affinity agent can be non-reactive and non-catalytic, thereby not permanently altering the chemical structure of an analyte to which it binds. An affinity reagent may include one or more known and/or characterized binding components or binding sites (e.g., complementarity-defining regions) that mediate or facilitate binding with a binding partner. Accordingly, an affinity reagent can be monovalent or multivalent (e.g., bivalent, trivalent, tetravalent, etc.).

As used herein, the term "nucleic acid nanoball" refers to a globular or spherical nucleic acid structure. A nucleic acid nanoball may include a concatemer of oligonucleotides that arranges in a globular structure. A nucleic acid nanoball may be formed by a method such as ligation of nucleic acid strands or rolling circle amplification of a concatemeric nucleic acid sequence. A nucleic acid nanoball may include DNA, RNA, PNA, modified or non-natural nucleic acids, or combinations thereof.

As used herein, the terms "binding affinity" or "affinity" refers to the strength or extent of binding between two entities such as molecules, moieties and or solid supports. For example, the terms can refer to the strength or extent of binding between an affinity reagent and a binding partner, the strength or extent of binding between an affinity reagent and an affinity target or the strength or extent of binding between an affinity reagent and a target moiety. Two entities are considered to have apparent binding affinity when the strength or extent of binding between the two entities can be detected or observed. A binding affinity of an affinity reagent for a binding partner, affinity target, or target moiety may be qualified as being a "high affinity," "medium affinity," or "low affinity." A binding affinity of an affinity reagent for a binding partner, affinity target, or target moiety may be quantified as being "high affinity" if the interaction has a dissociation constant of less than about 100 nM, "medium affinity" if the interaction has a dissociation constant between about 100 nM and 1 mM, and "low affinity" if the interaction has a dissociation constant of greater than about 1 mM. Binding affinity can be described in terms known in the art of biochemistry such as equilibrium dissociation constant (KD), equilibrium association constant (KA), association rate constant (kon), dissociation rate constant (koff) and the like. See, for example, Segel, Enzyme Kinetics John Wiley and Sons, New York (1975), which is incorporated herein by reference in its entirety. In some cases, two entities are considered to have no binding affinity, for example, when binding between the two entities is of insufficient strength or extent to be detected or observed. The binding affinity between two entities, for example, between an affinity reagent and a binding partner, affinity target, or target moiety, may be vanishingly small, not apparent or effectively zero.

As used herein, the term "promiscuity," when used in reference to an affinity reagent, refers to the affinity reagent binding to, or having the capability of binding to, two or more different analytes. For example, a promiscuous affinity reagent may: 1) bind to a plurality of different binding partners due to the presence of a common epitope within the structures of the different binding partners; or 2) bind to a plurality of different epitopes; or 3) a combination of both properties. Additional concepts pertaining to binding promiscuity are discussed in WO 2020106889A1, which is incorporated herein by reference in its entirety.

As used herein, the term "epitope" refers to an affinity target within a polypeptide or other analyte. Epitopes may include amino acid sequences that are sequentially adjacent in the primary structure of a polypeptide or amino acids that are structurally adjacent in the secondary, tertiary or quaternary structure of a polypeptide. An epitope can optionally be recognized by or bound to an antibody. However, an epitope need not necessarily be recognized by any antibody, for example, instead being recognized by an aptamer, miniprotein or other affinity reagent. An epitope can optionally bind an antibody to elicit an immune response. However, an epitope need not necessarily participate in, nor be capable of, eliciting an immune response.

As used herein, the term "binding probability" refers to the probability that an affinity reagent may be observed to interact with a binding partner and/or an affinity target within a particular binding context. A binding probability may be expressed as a percentage or as a discrete number (e.g., 40% or 0.40), a matrix of discrete numbers, or as mathematical model (e.g., a theoretical or empirical model). A binding probability may include one or more factors, including the binding specificity, the likelihood of locating the affinity target, or the likelihood of binding for a sufficient amount of time for the binding interaction to be detected. An overall binding probability may include binding probability when all factors have been weighted relative to the binding context.

As used herein, the term "binding context" refers to the environmental conditions in which an affinity reagent-binding partner interaction is observed. Environmental conditions may include any factors that may influence an interaction between an affinity reagent and a binding partner, such as temperature, fluid properties (e.g., ionic strength, pH), relative concentrations, absolute concentrations, fluid composition, binding partner conformation, affinity reagent conformation, and combinations thereof.

The term "comprising" is intended herein to be open-ended, including not only the recited elements, but further encompassing any additional elements (e.g. additional components or steps).

As used herein, the term "each," when used in reference to a collection of items, is intended to identify an individual item in the collection but does not necessarily refer to every item in the collection. Exceptions can occur if explicit disclosure or context clearly dictates otherwise.

Protein Characterization Methods

Described herein is a method, including: a) providing an array of polypeptides, wherein the array of polypeptides includes a first proteoform of a polypeptide and a second proteoform of the polypeptide, and wherein each polypeptide of the array of polypeptides is present at an individually observable address of the array; b) contacting the array of polypeptides with a first affinity reagent, wherein the first affinity reagent has a first characterized binding probability, wherein the first affinity reagent includes a first detectable label that is configured to transmit a first detectable signal; c) detecting a presence or absence of the first detectable signal at each observable address on the solid support; d) contacting the array of polypeptides with a second affinity reagent, wherein the second affinity reagent has a second characterized binding probability, wherein the second affinity reagent includes a second detectable label that is configured to transmit a second detectable signal; e) detecting a presence or absence of the second detectable signal at each observable address on the solid support; and f) characterizing presence or absence of the first proteoform and the second proteoform at each address of the array based upon the first characterized binding probability of the first affinity reagent and the second characterized binding probability of the second affinity reagent. The detectable label can be endogenous to the affinity reagent, e.g., the charge or mass of the reagent as detected by Surface Plasmon Resonance (SPR) or Field Effect Transistor, or the label can be exogenous to the affinity reagent, e.g., a fluorescent, magnetic or charged moiety conjugated synthetically to the reagent.

The systems described herein may include an array of polypeptides that are coupled to a solid support. The solid support may include a plurality of addresses that are configured to couple one or more polypeptides. In some configurations each address of the array includes a single coupled polypeptide. In other configurations, each address of the array includes more than one coupled polypeptide. An address on the array may include at least about 1, 2, 3, 4, 5, 6, 7, 8, 9, 10, 15, 20, 25, 30, 35, 40, 45, 50, 75, 100, 150, 200, 300, 400, 500, 750, 1000, or more than 1000 polypeptide(s). Alternatively or additionally, an address on the array may include no more than about 1000, 750, 500, 400, 300, 200, 150, 100, 75, 50, 45, 40, 35, 30, 25, 20, 15, 10, 9, 8, 7, 6, 5, 4, 3, 2, or 1 polypeptide(s).

An array of polypeptides may include a particular polypeptide species that has more than one distinguishable proteoform. An array of polypeptides may include more than one polypeptide species that has more than one distinguishable proteoform. In some cases, a polypeptide species may have a first known or characterized proteoform and/or a second known or characterized proteoform. In other cases, a polypeptide species may have a first unknown or uncharacterized proteoform and/or a second unknown or uncharacterized proteoform. In some configurations, performing a method set forth herein, such as the above-described method, may include identifying and/or quantifying one or more unknown proteoforms of a polypeptide species. In other configurations, performing a method set forth herein, such as the above-described method, may include identifying and/or quantifying one or more known proteoforms of a polypeptide species. In some configurations, performing a method set forth herein, such as the above-described method, may include identifying and/or quantifying one or more unknown proteoforms of two or more polypeptide species. In other configurations, performing a method set forth herein, such as the above-described method, may include identifying and/or quantifying one or more known proteoforms of two or more polypeptide species.

A polypeptide species of the present invention may comprise two or more isoforms. Accordingly, two or more polypeptides can have the same amino acid sequence but nevertheless be different proteoforms, for example, due to a particular post translational modification (PTM) at a given amino acid in the sequence A first proteoform and a second proteoform can have the same genetically encoded amino acid sequence, but differ with regard to the number and/or type of PTMs present. Two proteoforms having the same amino acid sequence can differ, for example, due to (i) the presence and absence of a PTM at a particular amino acid position in the amino acid sequence, (ii) the presence and absence of a PTM at a particular type of amino acid in the amino acid sequence, (iii) the number of PTMs in the amino acid sequence, (iv) the type of PTM(s) present at one or more amino acid positions in the amino acid sequence, (v) the type of PTM(s) present at one or more type of amino acids in the amino acid sequence, or (vi) a combination of two or more of the foregoing.

Exemplary post translational modifications include, but are not limited to, myristoylation, palmitoylation, isoprenylation, prenylation, farnesylation, geranylgeranylation, lipoylation, flavin moiety attachment, Heme C attachment, phosphopantetheinylation, retinylidene Schiff base formation, dipthamide formation, ethanolamine phosphoglycerol attachment, hypusine, beta-Lysine addition, acylation, acetylation, deacetylation, formylation, alkylation, methylation, C-terminal amidation, arginylation, polyglutamylation, polyglyclyation, butyrylation, gamma-carboxylation, glycosylation, glycation, polysialylation, malonylation, hydroxylation, iodination, nucleotide addition, phosphoate ester formation, phosphoramidate formation, phosphorylation, adenylylation, uridylylation, propionylation, pyrolglutamate formation, S-glutathionylation, S-nitrosylation, S-sulfenylation, S-sulfinylation, S-sulfonylation, succinylation, sulfation, glycation, carbamylation, carbonylation, isopeptide bond formation, biotinylation, carbamylation, oxidation, reduction, pegylation, ISGylation, SUMOylation, ubiquitination, neddylation, pupylation, citrullination, deamidation, elminylation, disulfide bridge formation, proteolytic cleavage, isoaspartate formation, and racemization. Further examples of post translational modifications include proteolysis and alternative splicing which can produce proteoforms that differ with respect to the length of the amino acid sequence or the relative order of amino acid sequence domains, despite the different proteoforms being expressed from the same gene.

PTMs may occur at particular amino acid residues of a polypeptide. For example, the phosphate moiety of a particular proteoform can be present on a serine, threonine, tyrosine, histidine, cysteine, lysine, aspartate or glutamate residue of the polypeptide. In another example, an acetyl moiety of a particular proteoform can be present on the N-terminus or on a lysine of the polypeptide. In another example, a serine or threonine residue of a proteoform can have an 0-linked glycosyl moiety, or an asparagine residue of a proteoform can have an N-linked glycosyl moiety. In another example, a proline, lysine, asparagine, aspartate or histidine amino acid of a proteoform can be hydroxylated. In another example, a proteoform can be methylated at an arginine or lysine amino acid. In another example, a proteoform can be ubiquitinated at the N-terminal methionine or at a lysine amino acid.

Proteoforms may be isolated in a degraded, truncated, or damaged state due to a natural cellular or extracellular process, such as oxidation, reduction, radical damage, or enzymatic cleavage. Exemplary proteoforms include those that have been modified or changed by a non-biological process, including but not limited to, cell lysis, fractionation of cellular components, synthetic procedures, biological assays, clinical assays or biochemical assays. Proteoforms may include partially or severely degraded proteins, truncated proteins, partially or fully denatured proteins, agglomerated proteins, damaged proteins, protein fragments, or modified proteins.

Polypeptides of a sample may be treated to remove at least one type of polypeptide PTM. For example, a polypeptide may be treated with a natural or unnatural glycosidase enzyme or equivalent chemical reagents known to remove at least some post translational glycans. Treating polypeptides with more than one type of PTM may remove at least some of the glycan PTMs while retaining, for example, phosphorylated amino acid residues. A polypeptide may be treated with a reducing agent to reduce disulfide bonds within the polypeptide and subsequently treated with a chemical reagent, for example, an haloacetamide reagent (for example, iodoacetamide or any other known thiol capping group) which "caps" resulting free thiols residing on cysteine side chains. Capped cysteine thiols may be susceptible to binding at least one of a set of affinity reagents which may result in at least partial polypeptide characterization. Polypeptides may be treated with phosphatases to remove phosphate groups in some cases while retaining different PTM groups. In some cases, polypeptides can be treated with a phosphatase that selectively removes phosphates from a particular type of amino acid or peptide motif without removing phosphates from another type of amino acid or peptide motif. Particularly useful phosphatases are tyrosine-specific phosphatases, serine/threonine-specific phosphatases, histidine-specific phosphatases and dual specificity phosphatases (e.g., tyrosine/serine/threonine-specific phosphatases). Other non-limiting PTMs may be (differentially) removed including, for example: acetate, amide groups, methyl groups, lipids, ubiquitin, myristoylation, palmitoylation, isoprenylation or prenylation (e.g., farnesol and geranylgeraniol), farnesylation, geranylgeranylation, glypiation, lipoylation, flavin moiety attachment, phosphopantetheinylation, and retinylidene Schiff base products. Samples may be treated to retain selected PTMs, for example, in some examples, phosphatase inhibitors may be added to a sample to retain one or more phosphorylated amino acid residues, for example, in the presence of biological fluids.

A protein characterization method may be used to identify and/or quantify a biochemical pathway which involves proteoforms. A biochemical pathway may include a series of linked or coupled protein molecules that act in concert to produce a biological outcome (e.g., the conversion of a reactant to a product or signal transduction). A protein characterization method may identify and/or quantify one or more unique protein molecules involved in a biochemical pathway. A protein characterization method may identify and/or quantify one or more unique protein molecules in an alternative pathway that diverts from or augments the main biochemical pathway. A protein characterization method may identify or quantify one or more ancillary or associated proteins with a biochemical pathway. For example, a structural protein or membrane protein may be co-expressed with proteins that constitute an activated biochemical pathway.

A protein characterization method may be used to determine absolute or relative amounts of various protein molecules including proteoforms in a biochemical pathway. A protein characterization method may be used to identify or quantify one or more rate-limiting enzymes or protein molecules in a biochemical pathway. A protein characterization method may allow the determination of the throughput of a biochemical pathway based upon observed amounts of protein molecules. In some cases, the results of a protein characterization method may be used to engineer the expression levels and/or degradation rates of one or more proteoforms within a biochemical pathway to enhance or optimize the throughput of the pathway. In some cases, the results of a protein characterization method may be used to determine or quantify the amount of increase or decrease in expression levels of one or more proteoforms within a biochemical pathway, for example, to enhance or optimize the throughput of the pathway. In some cases, the results of a protein characterization method may be used to determine or quantify the amount of increase or decrease in degradation rates of one or more proteoforms within a biochemical pathway, for example, to enhance or optimize the throughput of the pathway. In some cases, the results of a protein characterization method may be used to alter one or more proteoforms within a biochemical pathway to enhance or optimize the throughput of the pathway. In some cases, methods described herein may be used to quantify or compare total amounts of the same or different proteins between different cellular samples.

Exemplary biochemical pathways that can be characterized, in whole or part, using methods or compositions set forth herein include metabolic pathways, signal transduction pathways, genome replication, DNA transcription, RNA translation, protein secretion, protein degradation, apoptosis, etc. Exemplary metabolic pathways include, but are not limited to anabolic pathways, catabolic pathways, amphibolic pathways, carbohydrate metabolism, photosynthesis, cellular respiration, amino acid metabolism, vitamin and cofactor metabolism, nucleotide metabolism, protein metabolism, and lipid metabolism. Exemplary signal transduction pathways include, but are not limited to, Akt/PKB signalling pathway, AMPK signalling pathway, cAMP-dependent pathway, Eph/ephrin signalling pathway, Hedgehog signalling pathway, Hippo signalling pathway, Insulin signal transduction pathway, JAK-STAT signalling pathway, MAPK/ERK signalling pathway, mTOR signalling pathway, Nodal signalling pathway, Notch signalling pathway, PI3K/AKT/mTOR signalling pathway, TGF beta signalling pathway, TLR signalling pathway, VEGF signalling pathway and Wnt signalling pathway.

A protein characterization method may be used to determine the effect of manipulating a cell, tissue, biological fluid or organism on various proteins including, for example, various proteoforms. Polypeptides can be acquired from a cell, tissue, biological fluid or organism that has been manipulated, and the polypeptides can be assayed using a method set forth herein. Exemplary manipulations include, but are not limited to, genetic modifications, such as expression of a heterologous protein, mutation of an exon, mutation of an intron, mutation of a genetic regulatory element, or modification to the expression of a native protein; treatment with a substance such as a, known or suspected, energy source, vitamin, therapeutic agent, carcinogen, pathogen, or toxin; modifications to the physical environment, such as air pressure, air quality, temperature, light intensity, spectral range of light, pH, ionic strength, or osmotic pressure; or the like.

A polypeptide species may include a first proteoform and a second proteoform, where the first proteoform and/or the second proteoform is a splicing isoform of the polypeptide. Splicing variants may arise due to any one of several differing transcriptional processes, including constitutive splicing, exon skipping, intron retention, mutually exclusive exons, alternative 5' splicing sites, alternative 3' splicing sites, and combinations thereof.

A polypeptide species may include any number of proteoforms. A polypeptide species may include at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, or more proteoforms. Alternatively or additionally, a polypeptide species may include no more than about 1000, 900, 800, 700, 600, 500, 450, 400, 350, 300, 250, 200, 190, 180, 170, 160, 150, 140, 130, 120, 110, 100, 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, 2, or 1 proteoforms.

The present invention may utilize affinity reagents with known or characterized binding probabilities and/or binding affinities. An affinity reagent of the present invention may be characterized to have binding promiscuity, i.e., the ability to bind two or more different binding targets. For example, an affinity reagent may be promiscuous with respect to binding (i) two or more different polypeptide species, (ii) two or more different proteoforms, (iii) two or more different epitopes, or (iv) two or more different PTMs. Alternatively, an affinity reagent of the present invention may be characterized to have a lack of binding promiscuity, i.e., the characterized property of binding a highly-specific binding target. For example, an affinity reagent may selectively bind one proteoform of a particular polypeptide in a binding assay compared to other proteoforms of the polypeptide in the assay; an affinity reagent may selectively bind one polypeptide species in a binding assay compared to other polypeptide species in the assay; an affinity reagent may selectively bind one epitope in a binding assay compared to other epitopes in the assay; or an affinity reagent may selectively bind one PTM in a binding assay compared to other PTMs in the assay. In another example, an affinity reagent may have specificity for binding a polypeptide epitope having a particular PTM compared to a variant of the polypeptide epitope that lacks the PTM. In some cases, a promiscuous affinity reagent may be characterized as binding to two or more binding targets. In other cases, a promiscuous affinity reagent may be characterized as binding to the same target in differing sequence contexts (e.g., differing flanking amino acid sequences, differing tertiary structures, etc.). For a given context, an affinity reagent may be characterized as binding to two or more binding targets with unique binding probabilities for each binding target, or unique binding affinities (e.g., as measured by dissociation constant) for each binding target.

A polypeptide array including a polypeptide species may be contacted with one or more affinity reagents, for example, in a method set forth herein. A polypeptide array may be contacted with the one or more affinity reagents for sufficient time to permit an interaction between a polypeptide and the affinity reagent to occur. In some cases, the affinity reagent-polypeptide interaction may include a binding interaction. The array may be contacted with a plurality of affinity reagents in a simultaneous or stepwise fashion. The polypeptide array may be contacted with an affinity reagent with a known or characterized binding affinity or binding probability for the polypeptide species, or an isoform of the polypeptide species. In some configurations, affinity reagent binding probability is a higher probability of binding to a first proteoform of a polypeptide species compared to the probability of binding to a second proteoform of the polypeptide species. In some configurations, affinity reagent binding affinity is a higher binding affinity to a first proteoform of a polypeptide species compared to the binding affinity to a second proteoform of the polypeptide species. In some configurations, affinity reagent binding probability is a lower probability of binding to a first proteoform of a polypeptide species compared to the probability of binding to a second proteoform of the polypeptide species. In some configurations, affinity reagent binding affinity is a lower binding affinity to a first proteoform of a polypeptide species compared to the binding affinity to a second proteoform of the polypeptide species.

An affinity reagent may have a known or characterized binding probability or binding affinity for a PTM. In some configurations, the characterized binding probability or binding affinity includes a binding probability or binding affinity for a PTM where binding occurs independently of amino acid sequence context. For example, an affinity reagent may bind directly to a functional group or moiety added to a polypeptide by a PTM (e.g., a phosphate group, a methyl group, an acetyl group, a ubiquitin, a glycosylation, etc.). In some examples, an affinity reagent may bind to a polypeptide epitope having a post-translationally modified amino acid residue independently of a flanking amino acid sequence adjacent to the modified amino acid residue. For example, an affinity reagent may bind to epitopes of the sequence aXb, where X is a post-translationally modified amino acid and a and b are subsets of all possible 1, 2, or 3 residue amino acid sequences. In alternative configurations, the characterized binding affinity can be a binding probability or binding affinity for a PTM where binding is influenced by amino acid sequence context. For example, an affinity reagent may bind to epitopes of the sequence aXb, where X is a post-translationally modified amino acid and a and b are particular 1, 2, or 3 residue amino acid sequences, whereas the affinity reagent does not substantially bind to epitopes having other residues in the a or b portion of the epitope. In another example, an affinity reagent may only bind to a post-translationally modified amino acid in the presence of a particular non-contiguous tertiary structure.

An affinity reagent of the present invention may include any conceivable species of affinity reagent, including, without limitation, aptamers, antibodies, antibody fragments, mini-protein binders, DARPins, and avimers. An affinity reagent of the present invention may be contacted with a polypeptide array in a pool of affinity reagents. A pool of affinity reagents may include a homogeneous or heterogeneous plurality of affinity reagents. A plurality of affinity reagents may include a plurality of individual affinity reagents. A plurality of affinity reagents may include a plurality of monovalent affinity reagents, a plurality of polyvalent affinity reagents, or a plurality of polyvalent and monovalent affinity reagents. In some configurations, an affinity reagent of the present disclosure may include a polyvalent detectable affinity reagent including a plurality of affinity reagents (e.g., aptamers, antibodies, antibody fragments, mini-protein binders, or combinations thereof) coupled to the detectable affinity reagent. A polyvalent detectable affinity reagent may include an enhanced avidity for one or more binding targets in comparison to the individual binding affinities of the constituent affinity reagents of the detectable affinity reagent.

In some cases, an affinity reagent may have a known or characterized binding affinity or binding probability for one or more PTMs. In other cases, an affinity reagent may have an unknown or uncharacterized binding affinity or binding probability for one or more PTMs. In some cases, an affinity reagent having a known or characterized binding affinity or binding probability for an unmodified polypeptide epitope may have an unknown or uncharacterized binding affinity or binding probability for the epitope when it has been post-translationally modified. In other cases, an affinity reagent may have a binding affinity for a polypeptide epitope that exists in a target polypeptide and a polypeptide-containing PTM (e.g., SUMO, ubiquitin, etc.) attached to the target polypeptide.

Additional affinity reagents can also be useful in a polypeptide decoding process or other method set forth herein. For example, affinity reagents can recognize and bind to moieties other than amino acids. Lectins are polypeptides that show affinity for carbohydrate structures and can be used to decode glycosylation patterns on proteins. Carbohydrate binding motifs, often though not exclusively found as domains in carbohydrate-active proteins, may also be useful affinity reagents for the analysis of glycosylation or glycation structures on proteins. Non-biological compounds may also be useful affinity reagents. Titanium dioxide and zirconium dioxide have affinity for phosphorylated structures and can be used as probes to identify the presence and location of phosphoryl moieties on polypeptides.

After contacting an affinity reagent with a polypeptide array, bound or retained affinity reagents can be removed from the polypeptide array. Removal of a bound or retained affinity reagent from the polypeptide array may include a rinsing, washing, stripping, denaturing, degrading (e.g., photocleaving), or deactivating (e.g., photobleaching) process. An affinity reagent removal process may occur before a subsequent contacting of the polypeptide array with an affinity reagent. In some cases, bound or retained affinity reagents may be retained on the polypeptide array. For example, a removal step may be carried out to remove a first affinity reagent from an array with or without removing a second affinity reagent from the array. Accordingly, conditions can be deployed to selectively remove one affinity reagent while retaining another affinity reagent.

A method of the present disclosure can be configured to identify, characterize or quantify one or more proteoforms based on results of a detection assay set forth herein. For example, after contacting a polypeptide array with a first affinity reagent and a second affinity reagent, information on the presence or absence of interaction (e.g., binding) of the first affinity reagent and/or the second affinity reagent with each address on the polypeptide array may be utilized to infer the presence or absence of a first proteoform and/or a second proteoform at the address on the array. In some configurations, the characterizing of the presence or absence of the first proteoform and the second proteoform at each observable address of the array may include: i) providing the presence or absence of a first detectable signal at each address of the array and the presence or absence of a second detectable signal at each address of the array to a computer-implemented decoding algorithm; and ii) determining a characterization or identity of the polypeptide at each address of the array using a decoding algorithm. Optionally, the characterization can indicate presence of the first proteoform, the second proteoform, both proteoforms, or neither proteoform at an address. In some configurations of methods set forth herein, the number of polypeptides or proteoforms having a particular identity or other particular characteristic can be quantified. It will be understood that in some cases, the presence or absence of a polypeptide or proteoform at a given address can be uncertain.

Determining a characteristic of a polypeptide, such as its identity, may further include determining a confidence interval for the characterization. A characterization of polypeptide identity or other characteristic may occur to a confidence interval of at least about 50%, 60%, 70%, 80%, 85%, 90%, 91%, 92%, 93%, 94%, 95%, 96%, 97%, 98%, 99%, 99.9%, 99.99%, 99.999%, 99.9999%, 99.99999%, 99.999999%, 99.9999999%, 99.99999999%, or more. Alternatively or additionally, a characterization of polypeptide identity may occur to a confidence interval of no more than about 99.99999999%, 99.9999999%, 99.999999%, 99.99999%, 99.9999%, 99.999%, 99.99%, 99.9%, 99%, 98%, 97%, 96%, 95%, 94%, 93%, 92%, 91%, 90%, 85%, 80%, 70%, 60%, 50%, or less.

A polypeptide detection assay of the present disclosure can be carried out in a cyclic manner. For example, a first cycle can include a step of contacting one or more proteoforms, for example, an array of proteoforms for one or more polypeptides, with a first affinity reagent. A second cycle can include a step of contacting the one or more proteoforms with a second affinity reagent. Binding of the first and second affinity reagents to one or more proteoforms can be detected. The detected binding results can be analyzed in a decoding method to identify the one or more proteoforms. Multiple cycles of affinity reagent binding and/or data decoding may be performed to increase the confidence in a polypeptide prediction when utilizing affinity reagents with unknown PTM binding behavior or promiscuity for unmodified and modified binding targets. In some cases, decoding by a decoding algorithm may be performed with every affinity reagent considered. An affinity reagent may be cycled more than once to increase the strength of the inference made based upon the binding data of the affinity reagent. For example, an array of proteoforms can be contacted with the same affinity reagent in multiple cycles and the binding results from the multiple cycles can be evaluated together to improve accuracy compared to the results from a single cycle. Additionally, decoding steps may be performed with one or more affinity reagents removed from the analysis. For example, 300 binding steps can be decoded, each with a different single affinity reagent removed from the analysis. In cases where an affinity reagent binds an unknown PTM, removal of the affinity reagent from the decoding process may increase the identification confidence for any proteoform (e.g. a proteoform at a given address on an array) where the affinity reagent bound a PTM. Affinity reagents for which removal often results in increased protein identification confidence may be selected as candidates for a binding screen against a set of PTMs.

A decoding algorithm that is used to identify or characterize proteoforms in a method set forth herein may include one or more constitutive algorithms, such as a machine learning, deep learning, statistical learning, supervised learning, unsupervised learning, clustering, expectation maximization, maximum likelihood estimation, Bayesian inference, linear regression, logistic regression, binary classification, multinomial classification, or other pattern recognition algorithm. For example, a decoding step may perform the one or more algorithms to analyze signals or other information acquired from a binding assay (e.g., as inputs of the one or more algorithm) of (i) the binding characteristic of each affinity reagent, (ii) the database of the proteins in the sample, (iii) the list of binding coordinates, and/or (iv) the pattern of binding of affinity reagents to proteins, in order to generate or assign (e.g., as outputs of the one or more algorithms) (a) a probable identity to each coordinate and/or (b) a confidence (e.g., confidence level and/or confidence interval) for that identity. Examples of machine learning algorithms include, but are not limited to, support vector machines (SVMs), neural networks, convolutional neural networks (CNNs), deep neural networks, cascading neural networks, k-Nearest Neighbor (k-NN) classification, random forests (RFs), and other types of classification and regression trees (CARTs). Exemplary decoding algorithms for distinguishing different polypeptide species, and that can be adapted for use in distinguishing proteoforms in accordance with the teaching herein, are set forth in U.S. Pat. No. 10,473,654; US Pat. App. Pub. Nos. 2020/0286584 A1 or 2020/0082914 A1; or Egertson et al., BioRxiv (2021), DOI: 10.1101/2021.10.11.463967, each of which is incorporated herein by reference.

A particular affinity reagent or type of affinity reagent may be contacted with a polypeptide array one or more additional times. The polypeptide array can be detected during or after the contacting step such that addresses to which the affinity reagent binds can be identified. Optionally, the affinity reagent can be removed from the array after detection and prior to performing an additional step of contacting the array with affinity reagent. Alternatively, affinity reagent that was previously contacted with a polypeptide array need not be removed prior to contacting the polypeptide array with a subsequent affinity reagent. In the alternative configuration, the polypeptide array can be detected after both contacting steps have been performed, with or without detecting the array between the two contacting steps. Repeated contacting of a polypeptide array and detection of any resultant binding can increase the likelihood of identifying possible binding targets, or to increase confidence in identifications based on the binding data.

In some configurations, a polypeptide array can be serially contacted with different affinity reagents that recognize and bind to different polypeptides or proteoforms. A polypeptide assay may include contacting a polypeptide array with at least about 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900, 1000, 1500, 2000, 2500, 3000, 4000, 5000, or more unique affinity reagents, wherein one or more of the affinity reagents differ from each other with regard to the polypeptide or proteoform bound. Alternatively or additionally, a polypeptide assay may include contacting a polypeptide array with about 5000, 4000, 3000, 2000, 1500, 1000, 900, 800, 700, 600, 500, 450, 400, 350, 300, 250, 200, 150, 100, 90, 80, 70, 60, 50, 45, 40, 35, 30, 25, 20, 15, 10, 9, 8, 7, 6, 5, 4, 3, or fewer unique affinity reagents, wherein one or more of the affinity reagents differ from each other with regard to the polypeptide or proteoform bound.

Based upon identification of polypeptide species and proteoforms thereof, the absolute or relative abundances of one or more proteoforms for a particular polypeptide species may be quantified. A method set forth herein, such as an above-described method, may further include calculating a quantity of a first proteoform or a quantity of a second proteoform in an array of polypeptides. The array of polypeptides may include one or more additional polypeptide species. In some configurations, at least one polypeptide species of the one or more additional polypeptide species may include two or more proteoforms. In some cases, a method set forth herein, such as an above-described method, may include quantifying the absolute or relative abundances of one or more proteoforms of two or more polypeptide species on a polypeptide array. In some cases, a method set forth herein, such as an above-described method may include quantifying the absolute or relative abundances of one or more proteoforms of all identified polypeptide species on the polypeptide array.

A polypeptide array may include at least about 1, 2, 3, 4, 5, 10, 15, 20, 25, 30, 35, 40, 45, 50, 60, 70, 80, 90, 100, 150, 200, 250, 300, 350, 400, 450, 500, 600, 700, 800, 900, 1000, 1500, 2000, 2500, 3000, 4000, 5000, 10000, 15000, 20000, 30000, 40000, 50000, or more different polypeptide species. Alternatively or additionally, in some cases, a polypeptide array may include no more than about 50000, 40000, 30000, 20000, 15000, 10000, 5000, 4000, 3000, 2500, 2000, 1500, 1000, 900, 800, 700, 600, 500, 450, 400, 350, 300, 250, 200, 150, 100, 90, 80, 70, 60, 50, 45, 40, 35, 25, 20, 15, 10, 5, 4, 3, 2 or 1 different polypeptide species.

A polypeptide array may include at least about 1, 2, 3, 4, 5, 10, 15, 20, 25, 30, 35, 40, 45, 50, 60, 70, 80, 90, 100, 150, 200, 250, 300, 350, 400, 450, 500, 600, 700, 800, 900, 1000, 1500, 2000, 2500, 3000, 4000, 5000, 10000, 15000, 20000, 30000, 40000, 50000, or more different proteoforms, the proteoforms being isoforms of one or more different polypeptide species. Alternatively or additionally, a polypeptide array may include no more than about 50000, 40000, 30000, 20000, 15000, 10000, 5000, 4000, 3000, 2500, 2000, 1500, 1000, 900, 800, 700, 600, 500, 450, 400, 350, 300, 250, 200, 150, 100, 90, 80, 70, 60, 50, 45, 40, 35, 25, 20, 15, 10, 5, 4, 3, 2 or 1 different proteoforms, the proteoforms being isoforms of one or more different polypeptide species.

A protein characterization method may produce data regarding the characteristics and/or composition of a sample including a protein or proteoform(s) thereof. The data produced by a protein characterization method may include physical measurements produced by instrumentation as well as computational data based upon computer-implemented analysis of the physical measurement data. The computer-implemented analysis of physical measurement data from a protein characterization may produce data on the identities or other characteristics of proteins observed within a sample.

A protein characterization method may include collecting physical data by one or more methods. Protein characteristics (e.g. identities) may be determined by the analysis of physical data from one or more physical analysis methods carried out for various proteins or proteoforms thereof. In some cases, protein characteristics and/or identities may be determined by merging physical data from more than one physical analysis method, then analyzing the data. In other cases, protein characteristics and/or identities may be determined by separately analyzing physical data from more than one analysis method, then merging the data. Physical analysis methods may include any known method of obtaining physical data regarding protein characteristics or identities. In some cases, physical analysis methods may include single molecule measurements.

A protein or proteoform characterization method may include a single cell heterogeneity analysis. A single cell heterogeneity analysis may include a comparison of protein content between at least two individual cells producing at least one different proteoform or set of proteoforms. The at least two individual cells may be from the same type of organism or differing types of organisms. The at least two individual cells may be from the same individual organism or differing individual organisms. The at least two individual cells may be from the same tissue or differing tissues. Each analyzed individual cell in a single cell heterogeneity analysis may be collected at a different time or may be collected from a differing cellular environment (e.g., tumor cells collected before and after exposure to a chemotherapy compound). Each analyzed individual cell in a single cell heterogeneity analysis may be collected at the same time and from a same cellular environment (e.g., from a tumor). Each analyzed individual cell in a single cell heterogeneity analysis may be from a different stage of cell growth, e.g., division, growth, stasis, metastasis, stress, senescence, or death. Different samples from these two individual cells may have many different sets of proteoforms. Different cell types may be identified by methods described herein, for example, including but not limited to, microglia from astrocytes and animal cells from microbial cells. Different samples from these two individual cells may have the same set of proteoforms, however, they may include different amounts of proteoforms which may be quantified by methods described herein.

A single cell heterogeneity analysis utilizing a proteoform characterization method described herein may identify or quantify the difference in proteoform expression levels or quantities for one or more protein molecules in the subject cell. In some cases, a single cell heterogeneity analysis may include quantification by a protein characterization method of the expression levels of a single proteoform molecule in two differing cells or cell types. In other cases, a single cell heterogeneity analysis may include quantification by a protein characterization method of the expression level of one or more proteoform molecule in the same cell type under differing environmental conditions, due to different manipulations or at differing portions of the cell life cycle.

A single cell heterogeneity analysis may include identification or quantification by a proteoform characterization method of some or all polypeptides within a cellular proteome. A single cell heterogeneity analysis may include identification or quantification by a protein characterization method of all protein families within a cellular proteome. A single cell heterogeneity analysis may include identification or quantitation of at least about 0.01%, 0.1%, 1%, 5%, 10%, 15%, 20%, 25%, 30%, 35%, 40%, 45%, 50%, 55%, 60%, 65%, 70%, 75%, 80%, 85%, 90%, 95%, 99%, 99.9%, 99.99% or 100% of all polypeptides within a cellular proteome. Alternatively, or additionally, a single cell heterogeneity analysis may include identification or quantitation of no more than about 99.99%, 99.9%, 99%, 95%, 90%, 85%, 80%, 75%, 70%, 65%, 60%, 55%, 50%, 45%, 40%, 35%, 30%, 25%, 20%, 15%, 10%, 5%, 1%, 0.1%, 0.01% or less of all protein species or protein molecules within a cellular proteome.

A protein characterization method for proteoforms may utilize an array having a plurality of proteoforms at a plurality of sites in the array. In some embodiments, the proteoforms are applied to a functionalized substrate to chemically attach them to the substrate. In some cases, the proteoforms may be attached to the substrate via biotin attachments. In some cases, the proteoforms may be attached to the substrate via nucleic acid attachment. In some embodiments, the proteoforms may be applied to an intermediate substance (e.g., a structured nucleic acid particle or SNAP, such as nucleic acid origami or nucleic acid nanoball), where the intermediate substance is then attached to the substrate. In some cases, proteoforms may be conjugated to beads (e.g., gold beads) which may then be captured on a surface (e.g., a thiolated surface). In some cases, one proteoform may be conjugated to each SNAP or to each bead. In some cases, proteoforms may be conjugated to SNAPs or beads (e.g., one proteoform per SNAP or one proteoform per bead) and the SNAPs or beads may be captured on a surface (e.g., in microwells and/or nanowells).

A plurality of proteoforms may be contacted with a first set of affinity reagents, each affinity reagent including a detectable label, for example, a fluorescent moiety. A first set of affinity reagents may be applied to polypeptides in an appropriate solution. Optionally, each affinity reagent binds with a low to medium specific binding affinity to a plurality of different proteoforms of the polypeptides. A set of affinity reagents may include high binding affinity reagents with or without low to medium binding affinity reagents. a given affinity reagent may specifically recognize or bind to no more than one proteoform, or a given affinity reagent may be promiscuous, recognizing or binding more than one proteoform. For example, an individual affinity reagent may bind to two or more proteoforms of a given polypeptide. In some configurations of methods set forth herein, a promiscuous affinity reagent may bind to different individual proteoforms which have different primary structures, for example, having been expressed from different genes. An individual proteoform may be observed to bind to only one type of affinity reagent, or, it may be observed to bind to more than one different type of affinity reagent. Upon binding detectable labels of an affinity agent may provide binding reporter signals in real time (e.g. while a binding complex is present) or after the binding event. In some cases, the detectable labels may include nucleic acid tags or barcodes which may be read post-binding.

Figure 10:
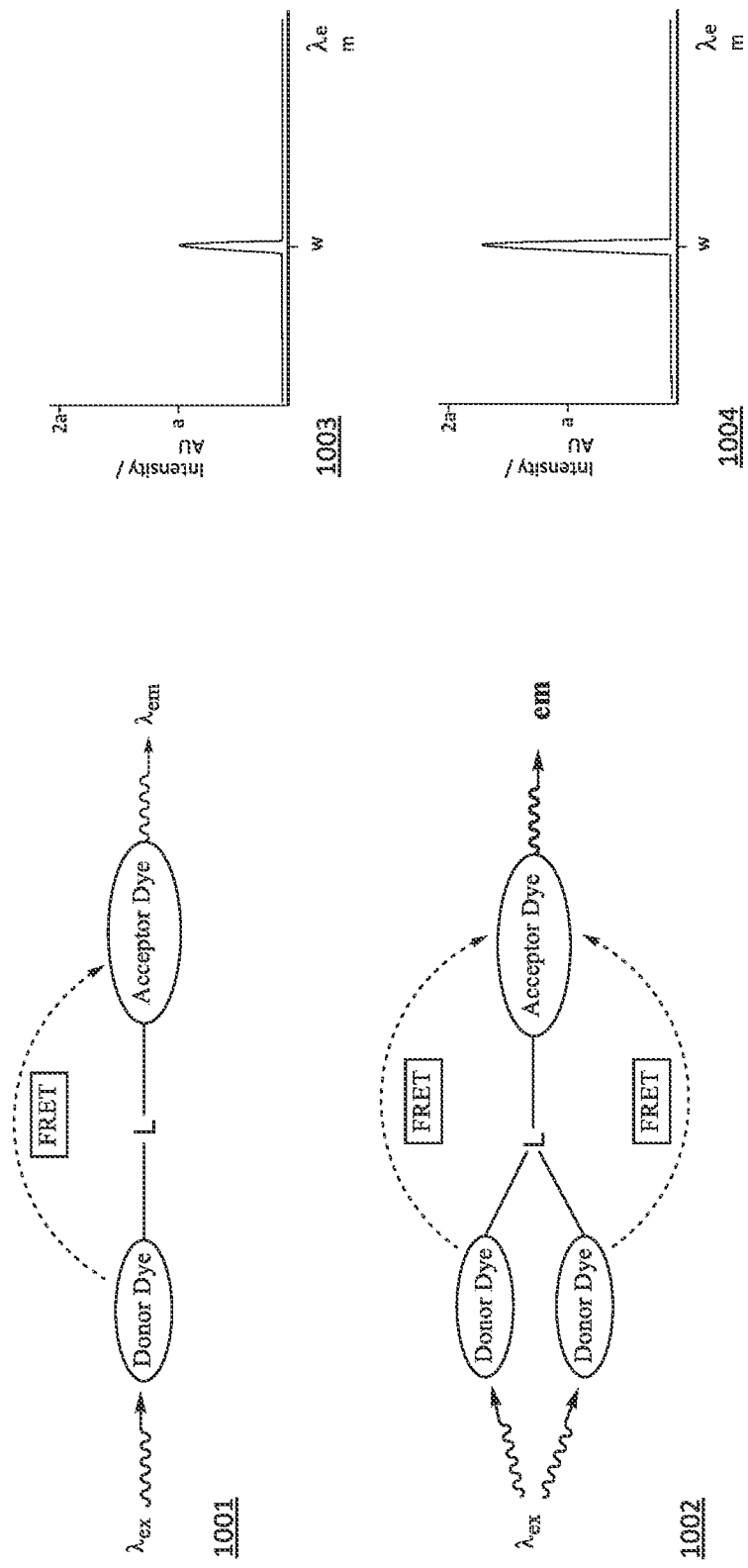
FIG. 10 illustrates two intramolecular FRET systems, one with one donor dye and one acceptor dye and one with two donor dyes and one acceptor dye. Both systems have the same excitation and emission wavelengths but the one with two donor dyes and one acceptor dye shows a greater emission intensity.

The absence of a binding signal between any one proteoform and any one affinity reagent can provide a useful contribution to the overall binding data information used to identify and quantitate a plurality of proteoforms. A first set of affinity reagents may be added to an array such that all of the affinity reagents are in contact with the array simultaneously or affinity reagents of the set can be added to an array serially such that two or more of the affinity reagents in the set are not in simultaneous contact with the array. Whether added together or serially, a set of affinity reagents can be in simultaneous contact with one or more proteoforms (e.g., an array of proteoforms). Accordingly, one or more reagents may be added sequentially without removing the previously added reagents. For example, a set of five different affinity reagents, Ap, Bp, Cp, Dp and Ep may be added to an array as a mixture of all five affinity reagents at the same time. Alternatively, affinity reagents of a set may be added individually and discretely to one or more proteoforms (e.g., an array of proteoforms) such that one affinity reagent is removed prior to adding a subsequent affinity reagent. Another method of contacting affinity reagents to an array of proteoforms may include adding a first group of affinity reagents, for example, Ap and Bp, followed by the cumulative addition of a second group of affinity reagents, Cp and Dp, and finally Ep may be cumulatively added. Binding signals in this case may be detected after each serial addition step or after the final addition step, or detection can occur after each addition as well as after the addition of the final affinity reagent. The latter case may be particularly useful when using different FRET labels having substantially the same excitation and emission wavelengths but different output intensities as exemplified in FIG. 10.

After binding signals are detected from a set of one or more affinity reagents bound to proteoforms on an array, the set of bound affinity reagents may be removed from the array. Removal of the affinity reagents may include one or more wash steps with appropriate solvents or buffer solutions. Appropriate solvents and buffer solutions may be chosen by observing the disappearance or significant reduction in affinity reagent binding signals upon washing with each solvent or buffer solution. Wash solutions may include one or more solutions of salts, detergents, preservatives or organic components. A wash solution may be an aqueous solvent or organic solvent. Buffer solutions may be used at various pH levels in combination with various concentrations of salts and detergents and may be used at various temperatures. Binding, detection and wash steps used in a method set forth herein can be carried out for a predetermined length of time or for a length of time that is determined empirically during the method.

After removal of a first set of one or more affinity reagents from an array of proteoforms, a second set of one or more affinity reagents may be added, for example, as described above for the first set of affinity reagents. Third, fourth, and higher sets of one or more affinity reagents may be added in the same way up to a final number of sets of affinity reagents. Subsequent sets of affinity reagents added after the first set may independently include any of the combinations of affinity reagents as described for the set of affinity reagents above. Detection of signals from affinity reagents and, optionally, analysis of the detected signals may begin after the addition of each set of affinity reagents or after the last affinity reagent is added. Part of the binding reporter signal analysis can include characterizing at least one of the proteoforms in the array.

Figure 12:
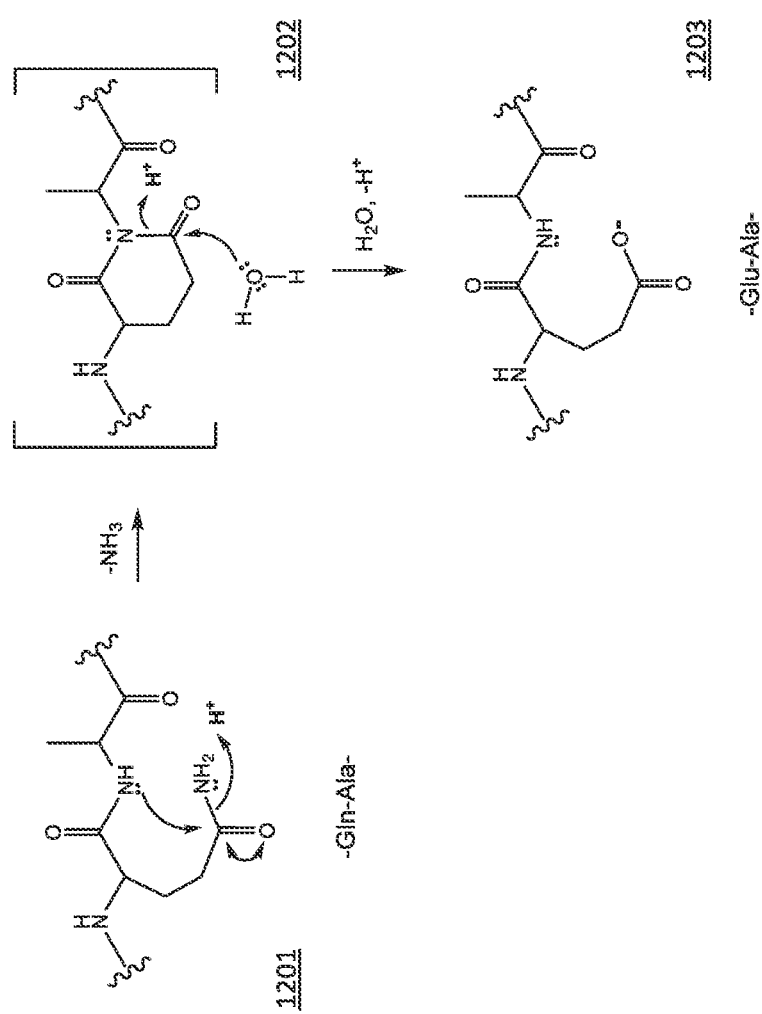
FIG. 12 shows a proposed mechanism for the formation of a glutamine deamidation post translational modification (PTM).

Deamidation of glutamine (Gln) residues may be a spontaneous or enzymatic process which may have significant implications in aging and human pathology. FIG. 12 shows a glutamine residue forming a glutarimide ring by the spontaneous loss of ammonia. The ring can open up two different ways to form a glutamic acid residue or at the alternative carbonyl group to form a g-glutamyl residue (not shown). Embodiments of the present invention may identify the γ/α-glutamyl and isoaspartyl/n-aspartyl products of Gln/Asn deamidation respectively using differing fingerprint binding patterns of sets of affinity reagents for any given proteoforms whereas characterization of this PTM from complex biological samples by shotgun proteomics is challenging. Spontaneous degenerative protein modifications (DPM) may control polypeptide turnover, alter structure and regulate function. Of these crucial modifications, deamidation of glutamine (Gln) residues in particular has been implicated in aging and degenerative proteinopathies, including cataracts, Alzheimer's disease (AD), Parkinson's disease (PD), and vascular dementia (VaD). The study of Gln deamidated isomers by liquid chromatography coupled to tandem mass spectrometry (LC-MS/MS) remains tremendously challenging due in part to only a +1 Dalton mass difference per residue between amidated and deamidated residues. Referring to FIG. 12, the product of a spontaneous deamidation involving a glutamine residue is a glutamic acid residue which carries a side chain negative charge at ambient pH while glutamine itself has a neutral side chain. As the product shown in FIG. 12 does not result in a change in molecular weight (O— is the same as NH2) it may often be challenging to detect using mass spectrometry. Under some LC conditions the O— would be protonated to afford an hydroxyl group, and the modification would have a +1 Dalton difference in molecular weight. This is still a tiny differential to detect proteoforms of larger molecular weights, for example, typical optimum molecular weight mass accuracies with the best high resolution mass accuracy mass spectrometers are presently around +/−2 Daltons for IgG antibodies which have molecular weights of around 150 kDa. Advantages of some embodiments of the present invention revolve around mapping differences in proteoform molecular surface characteristics using a plurality of sets of affinity reagents. A change in the charge state of one amino acid from neutral to negatively charged where the negative charge is confined over only three atoms of the carboxyl group is relatively massive in terms of changing the surface characteristics of a polypeptide. Hence, a deamidation PTM may dramatically change the overall binding affinities of at least one of the sets affinity reagents and may therefore provide a clear difference in binding signals between a non-deamidated polypeptide and a corresponding deamidated proteoform.

Similarly, asparagine (Asn) residues may deamidate at neutral pH via succinimide intermediate generating isoaspartyl (isoAsp) and n-aspartyl (Asp) products. While deamidation of Gln and Asn residues may be influenced by environmental factors, neighboring sequence and three-dimensional conformation of a protein, deamidation of Gln residues proceeds at a much slower rate than Asn due to the slower rate of formation of the six-membered glutaramide ring versus the five-membered succinimide ring. Spontaneous deamidation of Gln is thus considered an irreversible process which affects mainly long-lived proteins and can serve as a timeline of their functional and degradative states. In addition, nonspontaneous deamidation of Gln residues may be caused by NtQ-amidase and transglutaminases (TGs), a family of enzymes that mediate transamidation via ε-(γ-glutamyl) lysine cross-linking. Although transamidation mediated by these enzymes has been tentatively linked with the pathophysiology of celiac disease (CD), AD, and PD, very few protein substrates of these enzymes have been successfully identified in human tissues.

In some embodiments, described methods include deriving information on PTMs of unknown proteins. The information on PTMs may include the presence of a PTM without knowledge of the nature of a specific modification. For example, once a protein candidate sequence has been assigned to an unknown protein, a pattern of affinity reagent binding for assayed proteins may be compared to a database containing binding measurements for affinity reagents to the same or similar candidates from previous experiments. For example, a database of binding measurements may be derived from binding to a Nucleic Acid Programmable Protein Array (NAPPA) containing unmodified proteins of known sequence at known locations. Alternatively, a database of binding measurements may be derived from previous experiments in which protein candidate sequences were confidently assigned to unknown proteins.

Discrepancies in binding measurements between assayed proteins and databases of existing measurements may provide information on the likelihood of PTM. For example, if an affinity agent has a high frequency of binding to a candidate protein in a database, but does not bind the assayed protein, there may be a higher likelihood that the protein includes a PTM. If a binding epitope were known for the affinity reagent for which a binding discrepancy existed, the location of the PTM may be localized to, at or near the affinity reagent's epitope.

In some embodiments, information on specific PTMs may be derived by performing repeated affinity reagent measurements both before and after treatment of a protein-substrate conjugate with a natural or non-natural enzyme or by known chemical reagents which remove specific PTMs. For example, binding measurements may be acquired for a sequence of affinity reagents prior to treatment of a phosphorylated substrate with a phosphatase enzyme, and then repeated after treatment with a natural or unnatural phosphatase enzyme. Chemical reagents known to remove phosphate groups on phosphopeptides may be used in place of, or in combination with de-phosphorylating enzymes. Affinity reagents which bind an unknown protein prior to phosphatase treatment but not after phosphatase treatment (differential binding) may provide evidence of proteoform phosphorylation. Likewise, affinity reagents which bind to an epitope only after removal of a PTM in the epitopic region may be used. For example, an affinity reagent may not bind to a polypeptide having a phosphorylated tyrosine but may bind when the phosphate group is removed.

In some embodiments, a count of a particular PTM may be determined using binding measurements with one or more affinity reagents against a particular PTM. For example, an antibody that recognizes phosphorylated amino acid residues may be used as an affinity reagent. The binding of this reagent may indicate the presence of at least one phosphorylated amino acid residue on a known or unknown polypeptide. In some cases, the number of discrete PTMs of a particular type on an unknown polypeptide may be determined by counting the number of binding events measured for an affinity reagent specific to the particular PTM. For example, a phosphorylation specific antibody may be conjugated to a reporter molecular entity including one or more fluorescent labels. In this case, the intensity of the fluorescent signal may be used to determine the number of phosphorylation-specific affinity reagents bound to an unknown protein. The number of phosphorylation-specific affinity reagents bound to the unknown protein may in turn be used to determine the number of phosphorylation sites on the unknown protein.

In some embodiments, evidence from affinity reagent binding experiments may be combined with pre-existing knowledge of amino acid sequence motifs or specific protein locations likely to be post-translationally modified (e.g., from dbP™, PhosphoSitePlus, or UniProt) to derive more accurate count, identification, or localization of PTMs. For example, if the location of a PTM is not exactly determined from affinity measurements alone, a location containing an amino acid sequence motif frequently associated with the PTM of interest may be used.

In some embodiments, in cases where a single proteoform candidate match cannot be assigned to an unknown proteoform, a group of potential candidate matches may be assigned. A confidence level may be assigned to the unknown proteoform being one of any of the candidates in the group. The confidence level may include a probability value. Alternatively, the confidence level may include a probability value with an error. Alternatively, the confidence level may include a range of probability values, optionally with a confidence (e.g., about 90%, about 95%, about 96%, about 97%, about 98%, about 99%, about 99.9%, about 99.99%, about 99.999%, about 99.9999%, about 99.99999%, about 99.999999%, about 99.9999999%, about 99.99999999%, about 99.999999999%, about 99.9999999999%, about 99.99999999999%, about 99.999999999999%, about 99.9999999999999% confidence, or above 99.9999999999999% confidence). For example, an unknown proteoform may match strongly with two candidates. The two candidates may have high sequence similarity to each other (e.g., two proteoforms, such as proteoforms with single amino acid variants compared to a canonical sequence). In these cases, no individual candidates may be assigned with high confidence but a high confidence may be ascribed by matching it to a single proteoform group.

In some embodiments, the decoding approach further includes deriving information on PTMs of the unknown protein or peptide. The information on PTMs may include the presence of a PTM without knowledge of the nature of the specific modification. The database may be considered to be an exhaustive combinatorial space of PTMs. For example, once a candidate protein sequence has been assigned to an unknown protein or peptide, the pattern of affinity reagent binding for the assayed protein may be compared to a database containing binding measurements for the affinity reagents to the same candidate from previous experiments. For example, a database of binding measurements may be derived from binding to a Nucleic Acid Programmable Protein Array (NAPPA) containing unmodified proteins or peptides of known sequence at known locations.

Additionally or alternatively, a database of binding measurements may be derived from previous experiments in which protein or peptide candidate sequences were confidently assigned to unknown proteins or peptides. Discrepancies in binding measurements between the assayed protein or peptide and the database of existing measurements may provide information on the likelihood of PTM. For example, if an affinity agent has a high frequency of binding to the candidate protein or peptide in the database, but does not bind the assayed protein or peptide, there is a higher likelihood of a PTM being present somewhere on the protein or peptide. If the binding epitope is known for the affinity reagent for which there is a binding discrepancy, the location of the PTM may be localized to at or near the binding epitope of the affinity reagent. In some embodiments, information on specific PTMs may be derived by performing repeated affinity reagent measurements before and after treatment of the protein-substrate conjugate with an enzyme that specifically removes the particular PTM. For example, binding measurements may be acquired for a sequence of affinity reagents prior to treatment of the substrate with a phosphatase, and then repeated after treatment with a phosphatase. Affinity reagents which bind an unknown protein prior to phosphatase treatment but not after phosphatase treatment (differential binding) may provide evidence of phosphorylation. If the epitope recognized by the differentially binding affinity reagent is known, the phosphorylation may be localized to at or near the binding epitope for the affinity reagent In some cases, the count of a particular PTM may be determined using binding measurements with an affinity reagent against a particular PTM. For example, an antibody that recognizes phosphorylation events may be used as an affinity reagent. The binding of this reagent may indicate the presence of at least one phosphoryl moiety on the unknown protein. In some cases, the number of discrete PTMs of a particular type on an unknown protein or peptide may be determined by counting the number of binding events measured for an affinity reagent specific to the particular PTM. For example, a phosphorylation specific antibody may be conjugated to a fluorescent reporter. In this case, the intensity of the fluorescent signal may be used to determine the number of phosphorylation-specific affinity reagents bound to an unknown protein or peptide. The number of phosphorylation-specific affinity reagents bound to the unknown protein or peptide may in turn be used to determine the number of phosphorylation sites on the unknown protein or peptide. In some embodiments, evidence from affinity reagent binding experiments may be combined with pre-existing knowledge of amino acid sequence motifs or specific protein or peptide locations likely to be post-translationally modified (e.g., from dbP™, PhosphoSitePlus, or UniProt) to derive more accurate count, identification, or localization of PTM. For example, if the location of a PTM is not exactly determined from affinity measurements alone, a location containing an amino acid sequence motif frequently associated with the PTM of interest may be favored.

Samples

A sample used for a proteoform characterization method may be any sample containing protein. The samples may be taken from tissue or cells or from the environment of tissue or cells. In some examples, the sample could be a tissue sample or biopsy, biological fluid sample (e.g., blood, blood plasma, extracellular fluid, urine, mucus, saliva, semen, etc.), fecal samples, hair samples, cultured cells, culture media, discarded tissue, plant or fungal tissue, synthetic proteins, archaeal, bacterial and/or viral samples, archaeal samples, or protozoans. In some examples, a protein may be isolated from its primary source (cells, tissue, bodily fluids such as blood, environmental samples etc.) during sample preparation. A primary source may include any sample where a protein is a native or expected constituent. For example, primary sources for gastric enzymes may include cells from digestive organs, sample from gastric ducts, or fluid samples from digestive organs (e.g., bile). In a second example, a primary source for a cancer biomarker protein may be a tumor biopsy sample. In some examples, a protein may be isolated from a secondary source during sample preparation. A secondary source may include any sample where a protein is found even if the protein is not a native or expected constituent. For example, a secondary source for a pathogenic bacterial or viral protein may be a blood sample. In a second example, a secondary source for a cancer biomarker protein may be a bodily fluid (e.g., a blood sample containing a circulating tumor cell). Secondary sources may also include forensic samples when collected from non-native environments (e.g., blood, hair, or skin cell samples collected from fabric). A protein present in a method or composition herein may or may not be purified from its primary source or secondary source. In some cases, a primary or secondary source may be homogenized prior to further processing. The sample may contain intact proteins, denatured proteins, agglomerated proteins, protein fragments or partially degraded proteins. In some cases, sample polypeptides may be in a native state. In some cases, sample polypeptides may be in a non-native state, for example, in a denatured state or in a partially-folded or truncated state. A protein may be denatured at any stage during manipulation, including for example, upon removal from its native milieu or the protein can be maintained in a native state until a later stage of processing such as a stage where it is separated from other cellular components, fractionated from other proteins, functionalized for attachment to a solid support, attached to a solid support or contacted with a binding reagent or other reagent used for detection. In some cases, samples may include pure PTMs or PTM derivatives which may have been removed from polypeptide proteoforms. A cleaved PTM may be analyzed separately from, or in combination with, its corresponding polypeptide.

In some cases, a sample may be derived or collected from any type of organism. A sample may be derived or collected from an animal, plant, fungi, bacteria, virus, protozoan, or archaea. In some cases, a sample may be derived or collected from a primate such as a human or non-human primate. In some cases, a sample may be derived or collected from a domesticated animal (e.g., cat, dog, cow, pig, sheep, goat, horse, llama, alpaca, oxen, chicken, turkey, etc.). In some cases, a sample may be derived or collected from a model organism or a research organism (e.g., *C. elegans*, *D. melanogaster*, pig, rat, monkey, etc.). In some cases, a sample may be derived from a plant, including trees, shrubs, grasses, flowers, and crop plants (e.g., grains, legumes, vegetables, fruits, wheat, soy, rice, corn, palm, sorghum, oat, etc.) In some cases, a sample may include an organism that is collected from a host organism. A sample may include a parasitic, pathogenic, symbiotic, or latent organism collected from a host organism. A sample may include an organism linked with a disease state or disorder (e.g., an oncogenic virus). In some cases, a sample may include a protein derived from an organism. In some cases, a sample collected from a host organism may include a protein derived from an organism other than its native host organism such as a genetically modified organism. A sample may include a microbiome. A sample may include a plurality of proteins contributed by microbiome constituents.

In some cases, a sample having a protein may include a single cell, protein-containing particle (e.g., a viral particle), or a fragment thereof. In some cases, a single cell, protein-containing particle, or fragment thereof may be collected for a single cell heterogeneity analysis. A single cell, protein-containing particle, or fragment thereof may be collected by any known method in the art, such as fluorescence assisted cell sorting, magnetic-assisted cell sorting, and buoyancy-assisted cell sorting. In some cases, a single cell, protein-containing particle, or fragment thereof may be collected by an emulsion technique such as liposome or micellar capture.

A method, composition or apparatus of the present disclosure can use or include a plurality of polypeptides having any of a variety of compositions such as a plurality of polypeptides composed of a proteome or fraction thereof. For example, a plurality of polypeptides can include solution-phase polypeptides, such as polypeptides in a biological sample or fraction thereof, or a plurality of polypeptides can include polypeptides that are immobilized, such as polypeptides attached to a particle or solid support. By way of further example, a plurality of polypeptides can include polypeptides that are detected, analyzed or identified in connection with a method, composition or apparatus of the present disclosure. The content of a plurality of polypeptides can be understood according to any of a variety of characteristics such as those set forth below or elsewhere herein.

A plurality of polypeptides can be characterized in terms of total polypeptide mass. The total mass of polypeptide in a liter of plasma has been estimated to be 70 g and the total mass of polypeptide in a human cell has been estimated to be between 100 pg and 500 pg depending upon cells type. See Wisniewski et al. Molecular & Cellular Proteomics 13:10.1074/mcp.M113.037309, 3497-3506 (2014), which is incorporated herein by reference. A plurality of polypeptides used or included in a method, composition or apparatus set forth herein can include at least 1 pg, 10 pg, 100 pg, 1 ng, 10 ng, 100 ng, 1 mg, 10 mg, 100 mg, 1 mg, 10 mg, 100 mg or more polypeptide by mass. Alternatively or additionally, a plurality of polypeptides may contain at most 100 mg, 10 mg, 1 mg, 100 mg, 10 mg, 1 mg, 100 ng, 10 ng, 1 ng, 100 pg, 10 pg, 1 pg or less polypeptide by mass.

A plurality of polypeptides can be characterized in terms of percent mass relative to a given source such as a biological source (e.g. cell, tissue, or biological fluid such as blood). For example, a plurality of polypeptides may contain at least 60%, 75%, 90%, 95%, 99%, 99.9% or more of the total polypeptide mass present in the source from which the plurality of polypeptides was derived. Alternatively or additionally, a plurality of polypeptides may contain at most 99.9%, 99%, 95%, 90%, 75%, 60% or less of the total polypeptide mass present in the source from which the plurality of polypeptides was derived.

A plurality of polypeptides can be characterized in terms of total number of polypeptide molecules. The total number of polypeptide molecules in a *Saccharomyces cerevisiae* cell has been estimated to be about 42 million polypeptide molecules. See Ho et al., Cell Systems (2018), DOI: 10.1016/j.cels.2017.12.004, which is incorporated herein by reference. A plurality of polypeptides used or included in a method, composition or apparatus set forth herein can include at least 1 polypeptide molecule, 10 polypeptide molecules, 100 polypeptide molecules, $1 \times 10^4$ polypeptide molecules, $1 \times 10^6$ polypeptide molecules, $1 \times 10^8$ polypeptide molecules, $1 \times 10^{10}$ polypeptide molecules, 1 mole ($6.02214076 \times 10^{23}$ molecules) of polypeptide, 10 moles of polypeptide molecules, 100 moles of polypeptide molecules or more. Alternatively or additionally, a plurality of polypeptides may contain at most 100 moles of polypeptide molecules, 10 moles of polypeptide molecules, 1 mole of polypeptide molecules, $1 \times 10^{10}$ polypeptide molecules, $1 \times 10^8$ polypeptide molecules, $1 \times 10^6$ polypeptide molecules, $1 \times 10^4$ polypeptide molecules, 100 polypeptide molecules, 10 polypeptide molecules, 1 polypeptide molecule or less.

A plurality of polypeptides can be characterized in terms of the variety of full-length primary polypeptide structures in the plurality. For example, the variety of full-length primary polypeptide structures in a plurality of polypeptides can be equated with the number of different polypeptide-encoding genes in the source for the plurality of polypeptides. Whether or not the polypeptides are derived from a known genome or from any genome at all, the variety of full-length primary polypeptide structures can be counted independent of presence or absence of post translational modifications in the polypeptides. A human proteome is estimated to have about 20,000 different polypeptide-encoding genes such that a plurality of polypeptides derived from a human can include up to about 20,000 different primary polypeptide structures. See Aebersold et al., Nat. Chem. Biol. 14:206-214 (2018), which is incorporated herein by reference. Other genomes and proteomes in nature are known to be larger or smaller. A plurality of polypeptides used or included in a method, composition or apparatus set forth herein can have a complexity of at least 2, 5, 10, 100, $1 \times 10^3$, $1 \times 10^4$, $2 \times 10^4$, $3 \times 10^4$ or more different full-length primary polypeptide structures. Alternatively or additionally, a plurality of polypeptides can have a complexity that is at most $3 \times 10^4$, $2 \times 10^4$, $1 \times 10^4$, $1 \times 10^3$, 100, 10, 5, 2 or fewer different full-length primary polypeptide structures.

In relative terms, a plurality of polypeptides used or included in a method, composition or apparatus set forth herein may contain at least one representative for at least 60%, 75%, 90%, 95%, 99%, 99.9% or more of the polypeptides encoded by the genome of a source from which the sample was derived. Alternatively or additionally, a plurality of polypeptides may contain a representative for at most 99.9%, 99%, 95%, 90%, 75%, 60% or less of the polypeptides encoded by the genome of a source from which the sample was derived.

A plurality of polypeptides can be characterized in terms of the variety of primary polypeptide structures in the plurality including transcribed splice variants. The human proteome has been estimated to include about 70,000 different primary polypeptide structures when splice variants ae included. See Aebersold et al., Nat. Chem. Biol. 14:206-214 (2018), which is incorporated herein by reference. Moreover, the number of the partial-length primary polypeptide structures can increase due to fragmentation that occurs in a sample. A plurality of polypeptides used or included in a method, composition or apparatus set forth herein can have a complexity of at least 2, 5, 10, 100, $1 \times 10^3$, $1 \times 10^4$, $7 \times 10^4$, $1 \times 10^5$, $1 \times 10^6$ or more different primary polypeptide structures. Alternatively or additionally, a plurality of polypeptides can have a complexity that is at most $1 \times 10^6$, $1 \times 10^5$, $7 \times 10^4$, $1 \times 10^4$, $1 \times 10^3$, 100, 10, 5, 2 or fewer different primary polypeptide structures.

A plurality of polypeptides can be characterized in terms of the variety of polypeptide structures in the plurality including different primary structures and different proteoforms among the primary structures. Different molecular forms of polypeptides expressed from a given gene are considered to be different proteoforms. Protoeforms can differ, for example, due to differences in primary structure (e.g. shorter or longer amino acid sequences), different arrangement of domains (e.g. transcriptional splice variants), or different post translational modifications (e.g. presence or absence of phosphoryl, glycosyl, acetyl, or ubiquitin moieties). The human proteome is estimated to include hundreds of thousands of polypeptides when counting the different primary structures and proteoforms. See Aebersold et al., Nat. Chem. Biol. 14:206-214 (2018), which is incorporated herein by reference. A plurality of polypeptides used or included in a method, composition or apparatus set forth herein can have a complexity of at least 2, 5, 10, 100, $1 \times 10^3$, $1 \times 10^4$, $1 \times 10^5$, $1 \times 10^6$, $5 \times 10^6$, $1 \times 10^7$ or more different polypeptide structures. Alternatively or additionally, a plurality of polypeptides can have a complexity that is at most $1 \times 10^7$, $5 \times 10^6$, $1 \times 10^6$, $1 \times 10^5$, $1 \times 10^4$, $1 \times 10^3$, 100, 10, 5, 2 or fewer different polypeptide structures.

A plurality of polypeptides can be characterized in terms of the dynamic range for the different polypeptide structures in the sample. The dynamic range can be a measure of the range of abundance for all different polypeptide structures in a plurality of polypeptides, the range of abundance for all different primary polypeptide structures in a plurality of polypeptides, the range of abundance for all different full-length primary polypeptide structures in a plurality of polypeptides, the range of abundance for all different full-length gene products in a plurality of polypeptides, the range of abundance for all different proteoforms expressed from a given gene, or the range of abundance for any other set of different polypeptides set forth herein. The dynamic range for all polypeptides in human plasma is estimated to span more than 10 orders of magnitude from albumin, the most abundant polypeptide, to the rarest polypeptides that have been measured clinically. See Anderson and Anderson Mol Cell Proteomics 1:845-67 (2002), which is incorporated herein by reference. The dynamic range for plurality of polypeptides set forth herein can be a factor of at least 10, 100, $1 \times 10^3$, $1 \times 10^4$, $1 \times 10^6$, $1 \times 10^8$, $1 \times 10^{10}$, or more. Alternatively or additionally, the dynamic range for plurality of polypeptides set forth herein can be a factor of at most $1 \times 10^{10}$, $1 \times 10^8$, $1 \times 10^6$, $1 \times 10^4$, $1 \times 10^3$, 100, 10 or less.

An array of polypeptides may be prepared with a plurality of polypeptides derived from any conceivable source. A sample may be derived from an organism or an organism-derived substance or material. A sample may include any type of organism, including animals, non-human animals, humans, plants, fungi, bacteria, protozoa, archaea, viruses, or combinations thereof. The organism may be a domesticated, modified, or engineered organism, such as poultry, livestock, genetically-modified crops, non-modified crops, transgenic animals, transgenic plants, or production strains of microorganisms (e.g., *E. coli, S. cerevisiae*). A sample may include a substance derived from an organism, such as an extracellular secretion or debris from a deceased cell. A sample may be collected from a 2D cell culture line, a 3D cell culture line, a plant tissue sample, an animal tissue sample, a non-human animal tissue sample, a fungal tissue sample, a cultured tissue sample, a human patient-derived tissue sample, a veterinary patient-derived tissue sample, a skin or tissue swab, a tissue biopsy sample, a bodily fluid sample (e.g., blood plasma, blood serum, whole blood, urine, cerebrospinal fluid, saliva, semen, vaginal secretions, tears, mucus), a fecal sample, a cellular lysate, a fixed tissue sample (e.g., FFPE), a single-cell organism, a tissue-derived single cell, a secreted sample, an environmental sample, a microbial sample, a microbiome sample, a biofilm sample, or a non-biological sample. A polypeptide array may include a plurality of polypeptides derived from a non-biological source such as a forensic sample, an industrial sample, a consumer product, a geological sample, an archeological sample, a paleontological sample, an extraterrestrial sample, or a combination thereof.

The polypeptides of an array of polypeptides may be derived from a proteomic sample. A proteomic sample may include a sample that contains a substantially complete proteome, such as a cell sample, tissue sample, or microorganism. For example, a proteomic sample may contain at least 90%, 95%, 97%, 99%, 99.9% or more of the proteins present in the source from which the sample was derived. A proteomic sample may include a sample derived from a human, domesticated animal, wild animal, domesticated plant, wild plant, engineered microorganism, or natural microorganism. A sample may include a single proteome. A sample may include a plurality of proteomes, such as a population of organisms, a microbiome sample or a biome sample. A sample may include a pooled sample collected from a plurality of organisms within a population of organisms. A sample collected or derived from a microbiome or a biome may include one or more polypeptide species including two or more proteoforms, where a first proteoform of the one or more polypeptide species is derived from a first constituent organism of the microbiome or biome, and a second proteoform of the one or more polypeptide species is derived from a second constituent organism of the microbiome or biome. A microbiome sample or a biome sample may include one or more polypeptide species including two or more proteoforms, where a first proteoform and a second proteoform of the one or more polypeptide species are derived from a same constituent organism of the microbiome or biome.

A polypeptide array may include a plurality of polypeptides with each polypeptide of the plurality of polypeptides present at an individually observable address of the array. A plurality of polypeptides may include multimeric polypeptides (e.g., hemoglobin) or polypeptide complexes. A polypeptide complex may include a polypeptide that is reversibly or irreversibly coupled to a second biomolecules, such as, for example, a second polypeptide, a nucleic acid, a polysaccharide, or a lipid. A polypeptide complex may be formed naturally, for example through the biological function of a polypeptide (e.g., a nucleic-acid binding protein) or may be formed artificially through a means such as chemical cross-linking of neighboring or adjacent polypeptides.

Affinity Reagents

An affinity reagent of the present invention may include a detectable label that permits detection of a binding event by generating a detectable signal. A detectable signal from a binding event may be measured in real-time (e.g., fluorescence, luminescence) or may be measured after a binding event has ended (e.g., a recorded barcode). A polypeptide array may be contacted with a first pool of affinity reagents including a first detectable label, then contacted with a second pool of affinity reagents including a second detectable label. In some configurations, the first detectable label may be the same as the second detectable label. In other configurations, the first detectable label may be different from the second detectable label. A polypeptide array may be simultaneously contacted with a first pool of affinity reagents including a first detectable label, and a second pool of affinity reagents including a second detectable label. In some configurations, the first detectable label may be the same as the second detectable label. In other configurations, the first detectable label may be different from the second detectable label.

The first detectable label or the second detectable label may be selected from the group consisting of a fluorescent label; two or more fluorescent labels in the same molecule including, for example, intramolecular donor-acceptor FRET pairs with one or more donor fluorophores and one or more acceptor fluorophores, where the one or more donors and the one or more acceptors are in the same molecule and may be tuned to give a variety of different emission intensities; a luminescent label; a radiolabel; an isotopic label; and a nucleic acid label. In some configurations, a detectable label may include a fluorescent dye or label, such as FITC, Alexa Fluor® 350, Alexa Fluor® 405, Alexa Fluor® 488, Alexa Fluor® 532, Alexa Fluor® 546, Alexa Fluor® 555, Alexa Fluor® 568, Alexa Fluor® 594, Alexa Fluor® 647, Alexa Fluor® 680, Alexa Fluor® 750, Pacific Blue, Coumarin, BODIPY FL, Pacific Green, Oregon Green, Cy3, Cy5, Pacific Orange, TRITC, Texas Red, R-Phycoerythrin, and Allophcocyanin (APC). In some cases, the label may be an Atto dye, for example Atto 390, Atto 425, Atto 430, Atto 465, Atto 488, Atto 490, Atto 495, Atto 514, Atto 520, Atto 532, Atto 540, Atto 550, Atto 565, Atto 580, Atto 590, Atto 594, Atto 610, Atto 611, Atto 612, Atto 620, Atto 633, Atto 635, Atto 647, Atto 655, Atto 680, Atto 700, Atto 725, Atto 740, Atto MB2, Atto Oxa12, Atto Rho101, Atto Rho12, Atto Rho13, Atto Rho14, Atto Rho3B, Atto Rho6G, or Atto Thio12, or a combination thereof.

In some cases, the measurement of affinity reagent binding may be an average measurement. A series of repeated binding experiments may be performed, for example, due to imperfect binding of affinity reagents to targets, and the results of the series of binding experiments used to determine an average binding or a probability of the target being present. In some cases, a same affinity reagent may be applied to a sample at least 2, 3, 4, 5, 6, 7, 8, 9, 10, 11, 12, 13, 14, 15, 16, 17, 18, 19, 20, 30, 40, 50, 60, 70, 80, 90, or 100 times. In some cases, a pool of affinity reagents may be applied to the sample in such repetitions. In such cases, the same pool of affinity reagents may be applied to the sample, or different pools of affinity reagents may be applied such that at least one single affinity reagent is applied to the sample multiple times. Repeated binding cycles may be more important for affinity reagents with weak affinity for their target. The number of binding cycles each affinity reagent is subjected to may be determined based on the affinity of the affinity reagent for its one or more targets. In some cases, an affinity reagent may have a high affinity for a first target and a low affinity for a second target. In such a case the number of binding cycles may be determined based on either the high affinity target or the low affinity target. In some cases, the number of binding cycles is the same for all affinity reagents used in an assay, regardless of the affinities of the affinity reagents for their targets. In some cases, an affinity reagent used in the methods of this disclosure may be highly specific for a single epitope containing a PTM.

Solid Support/Substrate

The array of polypeptides of the current invention may include a solid support, wherein each polypeptide of the array is coupled to an address on the solid support. A solid support may include a material with desired characteristics such as hydrophobicity or hydrophilicity, amphipathicity, low adhesion of particular chemical or biological species, and particular chemical, optical, electrical, or mechanical properties. In some cases, a solid support material may be chosen for its compatibility with a detection technique or method (e.g., confocal fluorescent microscopy). For example, a material may be selected due to its low autofluorescence characteristic if a fluorescent detection method is to be utilized. A solid support may be a solid surface to which molecules can be covalently or non-covalently attached. Non-limiting examples of solid supports include slides, coverslips, surfaces of elements of devices, membranes, flow cells, wells, chambers, and macrofluidic chambers. Solid supports used herein may be flat or curved, or can have other shapes, and can be smooth or textured. In some cases, solid support surfaces may contain microwells. In some cases, solid support surfaces may contain nanowells. In some cases, solid support surfaces may contain one or more microwells in combination with one or more nanowells. A solid support may include polymers, glasses, semiconductors (e.g., silicon, germanium), ceramics, metals, minerals, a combination thereof, or other materials. In some instances, a solid support may include components made of a glass such as silicon dioxide, borosilicate glass, fused silica, or quartz. In other instances, a solid support may include an optical glass or a photochromatic glass. In some cases, a glass with a high sodium or potassium content may be selected as a material for a fluidic device component. A solid support may be fabricated from polymers or plastics such as polycarbonate, polyethylene, polypropylene, polyethylene terephthalate, polyvinyl chloride, polymethyl methacrylate, polydimethylsiloxane, polystyrene acrylics, latex and others. A solid support may include metals, metal oxides, and metal alloys such as stainless steel, brass, bronze, aluminum, gold, chromium, titanium, titanium oxide, tin oxide, zirconium oxide, or silicon dioxide. A solid support may include carbohydrates such as dextrans or cellulose. In some cases, a solid support may include two or more components with different (e.g. plastic vs. glass) or differing (e.g. borosilicate vs. quartz glass) material types. The solid support may have properties that are modified by the presence of polypeptide or polypeptide composites (e.g. intrinsic fluorescence that is blocked or shifted due to binding of polypeptide). A solid support may be patterned to create addresses having one or more of the materials or structural features exemplified above. The addresses may optionally be separated from each other by interstitial regions that lack the materials or have a different material from the addresses. The interstitial regions can optionally be selected from the materials or structural features exemplified above.

A solid support may be contained within a fluidic device. The fluidic device may include a flow cell, a microfluidic device, a cartridge, a tube such as a capillary tube, a channel, or a chip. In some configuration, a fluidic device may include a plurality of solid supports. A solid support of the plurality of solid supports may be fluidically isolated or fluidically connected to one or more additional solid supports.

A solid support or an address on a solid support may be characterized by a thickness or depth. The thickness of a solid support may be uniform or may vary over the body of the solid support. The thickness of the solid support may be altered by a fabrication, forming or machining process. In some cases, a solid support or address may have a thickness of about 1 micrometer ($\mu m$), 10 $\mu m$, 50 $\mu m$, 100 $\mu m$, 250 $\mu m$, 500 $\mu m$, 750 $\mu m$, 1 millimeter (mm), 5 mm, 1 centimeter (cm), 10 cm or more. In some cases, a solid support may have a thickness of at least about 1 micrometer ($\mu m$), 10 $\mu m$, 50 $\mu m$, 100 $\mu m$, 250 $\mu m$, 500 $\mu m$, 750 $\mu m$, 1 millimeter (mm), 5 mm, 1 centimeter (cm), 10 cm or more than 10 cm. Alternatively or additionally, a solid support or address may have a thickness of no more than about 10 cm, 1 cm, 5 mm, 1 mm, 750 $\mu m$, 500 $\mu m$, 250 $\mu m$, 100 $\mu m$, 50 $\mu m$, 10 $\mu m$, 1 $\mu m$ or less.

A solid support or address may include one or more surface coatings. A surface coating may be organic or inorganic. In some cases, a surface coating may be deposited by a suitable deposition process, e.g., atomic layer deposition, chemical vapor deposition, self-assembling monolayers. In some cases, a surface coating may be patterned by a suitable patterning process, e.g., dry etch, wet etch, lift-off, deep UV lithography or combination thereof. A deposited surface coating may have a uniform thickness or a variable thickness over a surface of a solid support. In some cases, a surface coating may include an atomic or molecular monolayer. In some cases, a surface coating may include a self-assembled monolayer. In some cases, a surface coating may include a metal or metal oxide layer. In some cases, a surface coating may include a silane layer (e.g., ethoxy-, methoxy- or chloro-silane), a phosphonate layer, or a phosphate layer. In some cases, a surface coating may include a polymer, a gel such as a hydrogel, a mineral, a ceramic, or an ink. A surface coating may provide a surface electrical charge density, such as a net positive charge or a net negative charge. A solid support may be patterned to create addresses having one or more of the surface coatings exemplified above. The addresses may optionally be separated from each other by interstitial regions that lack the surface coatings or have a different surface coating from the addresses. The interstitial regions can optionally be selected from the surface coatings exemplified above.

A surface coating on a solid support or address may be characterized by a particular thickness. A surface coating may be at least about 1 Angstrom (Å), 5 Å, 1 nanometer (nm), 5 nm, 10 nm, 20 nm, 30 nm, 40 nm, 50 nm, 100 nm, 250 nm, 500 nm, 1 micrometer ($\mu m$), 5 $\mu m$, 10 $\mu m$, 50 $\mu m$, 100 $\mu m$ or more. Alternatively or additionally, a surface coating may be no more than about 100 $\mu m$, 50 $\mu m$, 10 $\mu m$, 5 $\mu m$, 1 $\mu m$, 500 nm, 250 nm, 100 nm, 50 nm, 40 nm, 30 nm, 20 nm, 10 nm, 5 nm, 1 nm, 5 Å, 1 Å or less.

A solid support or address may include one or more surfaces that are coated with a layer of metal or metal oxide. A metal or metal oxide layer may include a particular species depending upon the preferable chemistry. Candidate metals or metal oxides may include zirconium oxide ($ZrO2$), hafnium (Hf), gold (Au), titanium dioxide ($TiO2$), aluminum (Al), aluminum oxide ($Al2O3$) or a combination thereof. A solid support may be patterned to create addresses having one or more of the metals or metal oxides exemplified above. The addresses may optionally be separated from each other by interstitial regions lack a particular metal or metal oxide. The interstitial regions can optionally be selected from the metals or metal oxides exemplified above.

In some cases, a solid support or address may be optically opaque. In some cases, a solid support or address may be optically clear at one or more wavelengths. In some cases, the solid support may be partially optically clear, or may be optically clear in some regions. For example, a solid support may be optically opaque in regions that are not functionalized (e.g. interstitial regions), and optically clear in regions that are functionalized (e.g. addresses).

In some configurations, the solid support may include a patterned array. A patterned array may include a plurality of distinct, structured binding addresses that are arranged in an ordered or random fashion. A patterned array may be formed by a lithographic process or any other conceivable microfabrication technique. In some configurations, a solid support may include a non-patterned array. A non-patterned array may include an array of polypeptides that is formed without pre-patterning of the solid support. For example, a non-patterned array may include a solid support with a uniform or blanket surface layer or surface coating. Polypeptides may be located at unique addresses on a non-patterned array by a mechanism such as intermolecular repulsions or steric blocking of adjacent molecules.

In some cases, a polypeptide or a plurality of polypeptides may be directly coupled or conjugated onto a solid support surface such as a surface at an address of an array, or a surface of a flow cell, microwell or microbead. For example, a polypeptide that has been functionalized with an NHS group may be contacted with a silicon surface covered in an aminated (including a primary or a secondary amine, or a primary or a secondary aniline) silane monolayer, thereby forming a covalent bond between the polypeptide and the silane. In other cases, a polypeptide may be functionalized with a magnetic nanoparticle that is configured to couple or conjugate with a complementary magnetic material (e.g., a surface with an array of embedded or tethered magnetic nanoparticles). In a further option, a polypeptide can be attached to an anchoring group such as a structured nucleic acid particle (SNAP) and the anchoring group can be attached to a solid support surface to mediate attachment of the polypeptide to the surface.

Anchoring Groups

Figure 11:
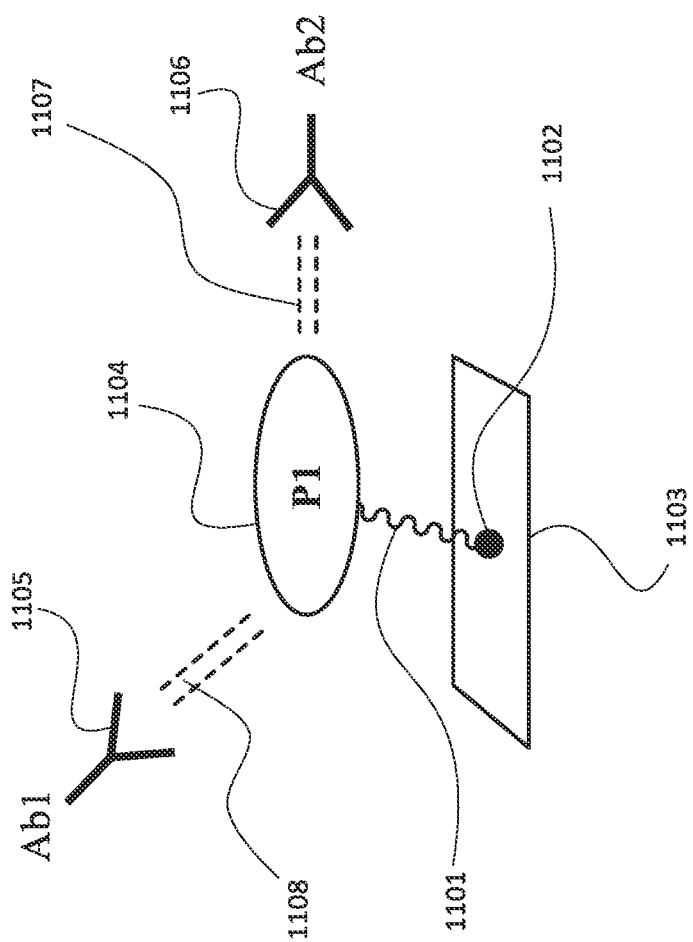
FIG. 11 shows two different affinity reagents binding with two different binding affinities to a single proteoform (P1) anchored to a surface.

Polypeptides from a functionalized or unfunctionalized polypeptide fraction may be coupled or conjugated to one or more anchoring groups. An anchoring group may include a particle that mediates or facilitates the binding of the polypeptide to a substrate or surface as shown in FIG. 11. An anchoring group may include a particle that couples a sample polypeptide to a solid support. An anchoring group may include a particle such as a nucleic acid particle, a structured nucleic acid particle, a polypeptide, a polymer, an inorganic nanoparticle, an organic nanoparticle, or a combination thereof. An anchoring group may interact with a surface by an interaction such as electrostatic adhesion, magnetic adhesion, covalent bonding, ionic bonding, hydrogen bonding, or coordinate bonding. An anchoring group may interact with a surface in a reversible fashion or an irreversible fashion.

A polypeptide (e.g. a sample polypeptide or standard polypeptide) from a plurality of polypeptides may be coupled or conjugated to an anchoring group by a reversible or irreversible interaction. A polypeptide of a plurality of polypeptides may be coupled to an anchoring group of a plurality of anchoring groups by a covalent bond. In some configurations, a polypeptide of a plurality of polypeptides may be coupled to an anchoring group of a plurality of anchoring groups by a click reaction or other covalent coupling chemistry exemplified elsewhere herein. A polypeptide of a plurality of polypeptides may be coupled to an anchoring group of a plurality of anchoring groups by a non-covalent interaction. In some configurations, the non-covalent interaction may be an electrostatic interaction, magnetic interaction, a hydrogen bond, or a binding interaction. In some configurations, the non-covalent hydrogen bond interaction may include nucleic acid hybridization. In other configurations, the non-covalent binding interaction may include a receptor-ligand interaction or a receptor-small molecule interaction, such as streptavidin-biotin, FITC-anti-FITC antibody, or digoxigenin-anti-digoxigenin antibody or other non-covalent interaction exemplified elsewhere herein.

An anchoring group may include a macromolecule or particle that possesses a positive or negative overall surface charge density. An anchoring group may include a macromolecule or particle that possesses a positive or negative region of surface charge density. The surface charge density of an anchoring group may be the opposite charge of a surface that a polypeptide conjugate is to be deposited upon. The surface charge density of an anchoring group may be neutral. The surface charge density of an anchoring group may be uniform over the available surface area of the anchoring group. A uniform surface charge density may increase the speed and/or likelihood of the anchoring group depositing upon a surface or material. Regions of positive or negative surface charge density of an anchoring group may be localized to one or more regions of the anchoring group structure. Localized surface charge density on an anchoring group may cause a polypeptide conjugate containing the anchoring group to deposit on a surface or material with a uniform or controlled orientation. Surface charge density of an anchoring group or a polypeptide conjugate containing an anchoring group may be measured by a suitable method such as electrophoretic measurement of zeta potential. A surface charge density of an anchoring group or a polypeptide conjugate containing an anchoring group may be determined by experimental measurement, computational modeling, or a combination thereof.

Anchoring groups may include one or more macromolecules. A suitable macromolecule for an anchoring group may include a macromolecule with a uniform or localized region of positive or negative surface charge density. A macromolecule in an anchoring group may possess a controlled or engineered structure, including a feature such as a polypeptide coupling or conjugation site, or a surface bonding site. A polypeptide coupling or conjugation site on an anchoring group may include a functional group configured to react with a functional group of a functionalized or unfunctionalized polypeptide, thereby forming a covalent bond between the anchoring group and the polypeptide. Suitable macromolecules may include nucleic acids, proteins, or polymers. A nucleic acid anchoring group may include a structured nucleic acid particle (SNAP) such as a DNA nanoball, DNA nanotube, or DNA origami. A polypeptide-based anchoring group may include an engineered or non-engineered polypeptide that has a tendency to deposit on a surface or material. A polypeptide for a polypeptide-based anchoring group may be prepared for conjugation to a polypeptide from a polypeptide fraction by methods similar to those described above. A polymer-based anchoring group may include ionic or non-ionic polymers.

In other configurations, an anchoring group may include a particle, such as a nanoparticle, that provides a plurality of attachment sites for two or more binding components, and optionally one or more label components. In some configurations, a particle may include a surface that is functionalized, can be functionalized, or is otherwise modifiable to provide attachment sites for polypeptide coupling. In some configurations, a particle may provide a template for a shell, surface coating, or surface layer (e.g., a surface coating including a polymer or hydrogel coating, a surface layer of functional groups) that contains or can be modified to contain attachment sites for detectable label components. A surface coating may include a polymer, biopolymer, metal, or metal oxide. In some configurations, an anchoring group may effectively function as a label component (e.g., a fluosphere or quantum dot). A particle for an anchoring group may include a surface coating or surface layer that has a surface electrical charge. The surface electrical charge may have a net positive charge or a net negative charge. An anchoring group may be formulated or modified to include a plurality of functional groups that are configured to couple to a solid support by a covalent or non-covalent interaction. In some configurations, the plurality of functional groups may include a functional group selected from the group consisting of an alkyl, alkenyl, alkynyl, phenyl, halide, hydroxyl, carbonyl, aldehyde, acyl halide, ester, carboxylate, carboxyl, carboalkoxy, methoxy, hydroperoxy, ether, hemiacetal, hemiketal, acetal, ketal, orthoester, epoxide, carboxylic anhydride, carboxamide, amine, ketimine, aldimine, imide, azide, azo, cyanate, isocyanate, nitrate, nitrile, isonitrile, nitrosoxy, nitro, nitroso, oxime, pyridyl, carbamate, sulfhydryl, sulfide, disulfide, sulfinyl, sulfonyl, sulfo, thiocyanate, isothiocyanate, carbonothioyl, thioester, thionoester, phosphino, phosphono, phosphonate, phosphate, borono, boronate, and a borinate. In some configurations, an anchoring group may be modified to include a functional group that is configured to undergo a click reaction. In other configurations, an anchoring group may be modified to include a functional group that is configured to undergo a chemical cross-linking or a photo-initiated cross-linking reaction.

An anchoring group may include a detectable label that permits detection of the anchoring group. A detectable label may include a fluorescent label, a luminescent label, a radiolabel, an isotopic label, an enzymatic tag, or a nucleic acid label or barcode. An anchoring group may be conjugated with a detectable label. The conjugated detectable label may be conjugated by a covalent bond (e.g., a reactive dye) or a non-covalent interaction (e.g., hybridization of a nucleic acid tag, an intercalation dye). A detectable label may be used to quantify anchoring groups in solution or detect anchoring groups at individual locations on a substrate.

An anchoring group or a linkage between an anchoring group and a polypeptide may further include a linker. A linker may be a bifunctional, trifunctional, or polyfunctional linker. A bifunctional linker may be a homobifunctional linker or a heterobifunctional linker. A linker may include a reporting molecule that is released upon successful coupling of an anchoring group to a polypeptide. For example, a click-to-release strategy may be utilized to covalently couple a polypeptide having a click handle with an anchoring group having a second click handle (e.g., inverse-electron demand Diels Alder click-to-release).

An anchoring group may be configured to be coupled or conjugated to a functionalized or unfunctionalized polypeptide (e.g. sample polypeptide or standard polypeptide). Functional groups capable of rapidly forming covalent bonds with functionalized or unfunctionalized polypeptides may be of particular interest for the functionalization of anchoring groups. In general, functional groups of interest will include most common species for bioconjugation. Such functional groups may include "click" reagents that are capable of forming highly specific products with complementary functional groups in a rapid and irreversible fashion. Exemplary functionalization chemistries are described above. An anchoring group may include one or more sites for polypeptide coupling or conjugation. An anchoring group with more than one attachment site may be capable of coupling or conjugating more than one polypeptide. An anchoring group may include a fixed number of polypeptide attachment sites, such as at least about 1, 2, 3, 4, 5, 6, 7, 8, 9, 10, 20, 30, 40, 50, 75, 100, 200, 300, 400, 500, 1000, 5000, 10000, 50000, 100000, 500000, 1000000, or more than 1000000 attachment sites. Alternatively or additionally, an anchoring group may include a fixed number of polypeptide attachment sites, such as no more than about 1000000, 500000, 100000, 50000, 10000, 5000, 1000, 500, 400, 300, 200, 100, 75, 50, 40, 30, 20, 10, 9, 8, 7, 6, 5, 4, 3, 2, or less than 2 attachment sites. An anchoring group may include a fixed number of coupled polypeptides, such as at least about 1, 2, 3, 4, 5, 6, 7, 8, 9, 10, 20, 30, 40, 50, 75, 100, 200, 300, 400, 500, 1000, 5000, 10000, 50000, 100000, 500000, 1000000, or more than 1000000 coupled polypeptides. Alternatively, or additionally, an anchoring group may include a fixed number of coupled polypeptides, such as no more than about 1000000, 500000, 100000, 50000, 10000, 5000, 1000, 500, 400, 300, 200, 100, 75, 50, 40, 30, 20, 10, 9, 8, 7, 6, 5, 4, 3, 2, or less than 2 coupled polypeptides.

Polypeptide Assays/Detection Methods

A method of the present invention may include: a) performing any of the above-described methods; and b) quantifying proteoforms for at least about a certain percentage of a proteome. A proteomic characterization method may characterize or identify proteoforms for at least a certain percentage of polypeptide species within the proteome. A proteomic characterization method may characterize or identify proteoforms for at least about 0.0000001%, 0.000001%, 0.00001%, 0.0001%, 0.001%, 0.01%, 0.1%, 0.5%, 1%, 5%, 10%, 15%, 20%, 25%, 30%, 35%, 40%, 45%, 50%, 55%, 60%, 65%, 70%, 75%, 80%, 85%, 90%, 95%, 99%, 99.9%, 99.99%, 99.999%, 99.9999%, 99.99999%, 99.999999%, or more than 99.999999% of all polypeptide species in a proteome. Alternatively or additionally, a proteomic characterization method may characterize or identify proteoforms for no more than about 99.999999%, 99.99999%, 99.9999%, 99.999%, 99.99%, 99.9%, 99%, 95%, 90%, 85%, 80%, 75%, 70%, 65%, 60%, 55%, 50%, 45%, 40%, 35%, 30%, 25%, 20%, 15%, 10%, 5%, 1%, 0.5%, 0.1%, 0.01%, 0.001%, 0.0001%, 0.00001%, 0.000001%, 0.0000001%, or less than 0.0000001% of all polypeptide species in a proteome.

The present disclosure further provides methods for detecting one or more polypeptide proteoforms or polypeptide proteoform products (e.g., polypeptide proteoform composites). A polypeptide proteoform can be detected using one or more affinity reagent having known binding affinity for the polypeptide. The affinity reagent and/or the polypeptide can be bound to form a complex and then formation of the complex can be detected. The complex can be detected directly, for example, due to a label that is present on the affinity reagent or polypeptide. In some configurations the complex need not be directly detected, for example, in formats where the complex is formed and then the affinity reagent, polypeptide, or a tag or label component that was present in the complex is then detected.

In some detection assays, a polypeptide isoform can be modified in a multicycle assay and modified products from each cycle can be detected. For example, the polypeptide can be modified in at least one cycle, two cycles, or substantially all cycles of the multicycle assay. Exemplary modifications to polypeptides include, but are not limited to, removal of a terminal amino acid, chemical modification of a terminal amino acid, chemical modification of a particular type of PTM, chemical modification of a particular type of amino acid, or the like.

Figure 13:
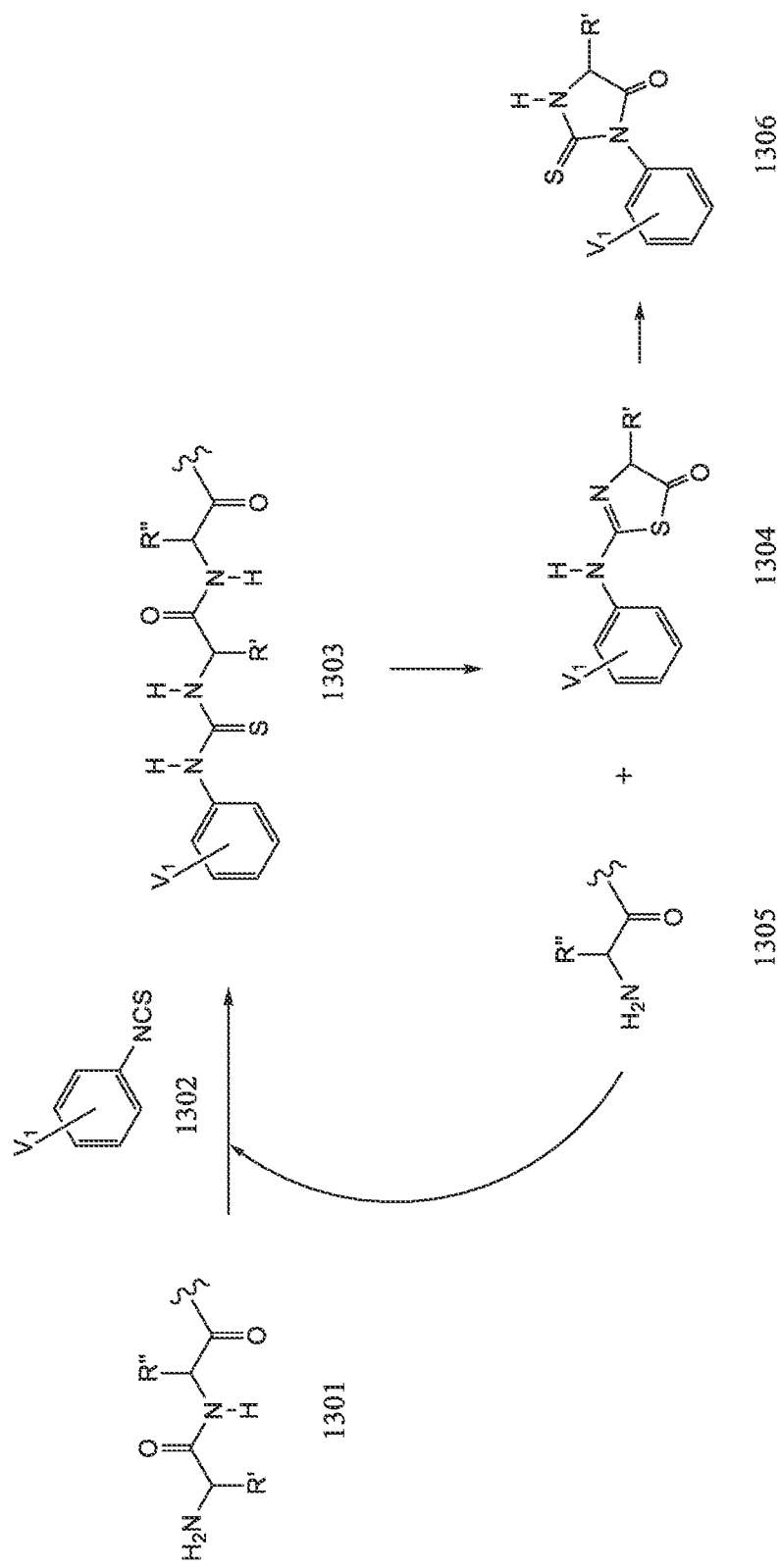
FIG. 13 shows an Edman-type sequencing reaction.

FIG. 13 shows a polypeptide 1301 being sequenced by a sequential process in which each cycle includes steps of labeling and removing N-terminal amino acids of a polypeptide isoform in a step-wise manner, and detecting released N-terminal labels. An example of this configuration is an Edman-type sequencing reaction in which a phenyl isothiocyanate 1302 reacts with a N-terminal amino group under mildly alkaline conditions, for example, about pH 8, to form an isolable, relatively stable cyclical phenylthiocarbamoyl Edman complex derivative 1303. The phenyl isothiocyanate 1302 may be substituted or unsubstituted with one or more functional groups, linker groups, or linker groups containing functional groups (shown as a V1 substituent on the phenyl group of 1302). An Edman-type sequencing reaction can include variations to reagents and conditions that yield a detectable removal of amino acids from a protein terminus, thereby facilitating determination of the amino acid sequence for a protein or portion thereof. For example, the phenyl group may also be replaced with at least one aromatic, heteroaromatic or aliphatic group which may participate in an Edman-type sequencing reaction, non-limiting examples including: pyridine, pyrimidine, pyrazine, pyridazoline, fused aromatic groups such as naphthalene and quinoline), methyl or other alkyl groups or alkyl group derivatives (e.g., alkenyl, alkynyl, cyclo-alkyl). Under certain conditions, for example, acidic conditions of about pH 2, derivatized terminal amino acids may be cleaved, for example, as a thiazolinone derivative 1304. The thiazolinone amino acid derivative under acidic conditions may form a more stable phenylthiohydantoin (PTH) or similar amino acid derivative 1306 which can be detected (for example, by chromatography, capillary electrophoresis, binding to an affinity reagent such as an antibody or aptamer, or mass spectrometry). This procedure can be repeated iteratively for residual polypeptide 1305 to identify the subsequent N-terminal amino acids and so forth as depicted in the cyclic nature of FIG. 13. Many variations of the Edman degradation have been described and may be used including, for example, a one step removal of an N-terminal amino acid using alkaline conditions (Chang, J. Y., FEBS LETTS., 1978, 91(1), 63-68, which is incorporated herein by reference).

Non-limiting examples of V1 in 1302 may further include; biotin and biotin analogs, fluorescent groups, click functionalities, for example, an azide or an acetylene. V1 may be part of these groups, for example, fluorescein isothiocyanate may react with the N-terminus of a polypeptide in place of phenyl isothiocyanate. V1 may be a DNA, RNA, peptide or small molecule barcode or other tag which may be further processed and/or detected. Barcodes may contain stable isotopes of hydrogen, carbon, nitrogen, oxygen, sulfur, phosphorus, boron or silicon. Barcodes containing stable isotopes may be detected by mass spectrometry. V1 may also include a metal complexing agent such as NTA (nitrolotriacetic acid) which binds strongly to certain metal ions, such as nickel (II) ions (Ni2+), where the Ni2+ ions may link V1 to another molecular entity or surface including histidines or equivalents.

Affinity reagents described herein may be used in combination with Edman-type sequencing reactions. For example, an array including a plurality of polypeptides may have a first proteoform of a polypeptide including an N-terminal phosphotyrosine residue. The polypeptide may have a second proteoform with a phosphotyrosine amino acid residue remote from its N-terminus. A first affinity reagent having a first detectable label may bind to the first proteoform of the polypeptide but not to the second proteoform of the polypeptide. A second affinity reagent having a second detectable label may bind to the second proteoform of the polypeptide and not to the first proteoform of the polypeptide. The two proteoforms of the polypeptide may be characterized by analyzing signals from the first and second affinity reagents binding to their respective first and second proteoforms of the polypeptide. The first and second labels may optionally be distinguishable from each other, but need not be, for example when used in separate cycles of a detection method set forth herein. Further characterization may be performed by employing one or more Edman-type sequencing steps. After contacting the array with first and second affinity reagents and detecting corresponding binding signals as described above, one or more Edman-type sequencing step may be performed. Edman sequencing can include at least two main steps, the first step includes reacting an isothiocyanate or equivalent with polypeptide N-terminal residues at about pH 8. This forms a relatively stable Edman complex, for example, a phenylthiocarbamoyl complex. The phenylthiocarbamoyl complex may include further chemical functionalities, for example, in some Edman-type methods it may include a fluorescent group, or a click chemistry functionality. The second Edman sequencing step can include warming or heating the Edman complex until the N-terminal amino acid residue is removed. A similar step can be used in other Edman-type methods. This may remove all N-terminal residues of the polypeptides on the array including the N-terminal phosphotyrosine residue from the first proteoform of the polypeptide. The array may be contacted again with the first affinity reagent which now lacks a binding signal for the first proteoform of the polypeptide. Contacting the array with the second affinity reagent may show a positive binding result for the second proteoform of the polypeptide. In this way further characterization of at least the first proteoform of the polypeptide can be achieved. N-terminal residues cleaved by an Edman-type process, for example as phenylthiohydantoins may be further analyzed. The method may also be used for a polypeptide having an N-terminal PTM within about five or fewer amino acid residues of its N-terminus. In these cases, before an N-terminal amino acid residue including a PTM is cleaved, changes in binding signals may be seen from the affinity reagents as PTM neighboring N-terminal amino acids are sequentially removed.

Figures 14A, 14B, 14C, 14D, 14E, 14F, 14G:
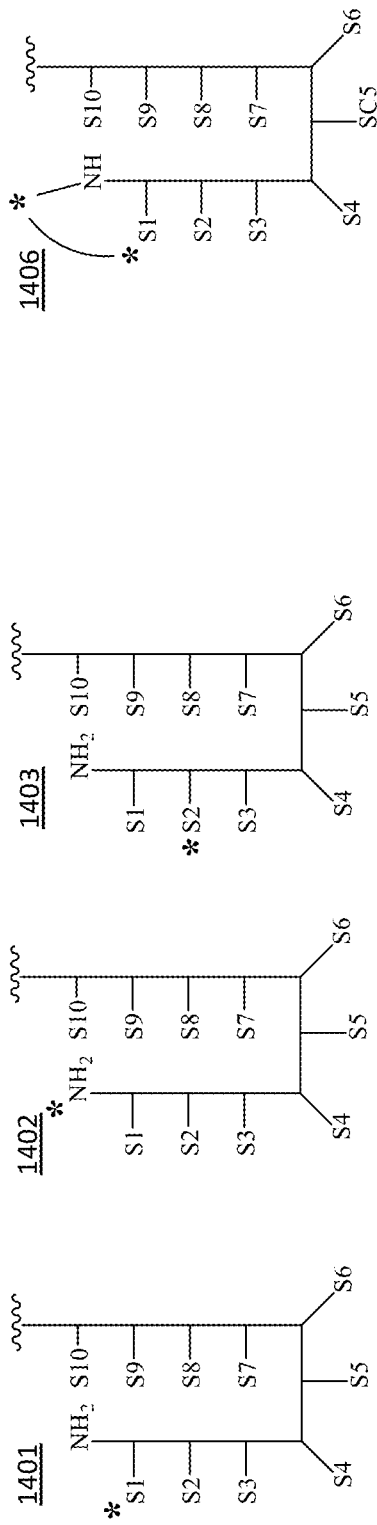
FIG. 14A-G shows six truncated polypeptide N-termini carrying one or more PTMs (PTMs) at various amino-acid residues which are relatively close to the N-terminal amino acid residue.

FIGS. 14A-E show five different truncated proteoforms of the same polypeptide where at least one PTM (*) resides in different locations in spatial proximity to the N-terminal portion of the polypeptide. FIG. 14A includes a PTM on the side chain of N-terminal residue (S1). A first affinity reagent to this polypeptide may bind to an epitope, for example, the first three amino acid residues including at least the N-terminal primary amino group (NH2) and at least one of the amino acid side chains of the first three amino acid residues (S1*, S2 and S3) where a substantial amount of binding affinity may occur between the first affinity reagent and the PTM moiety. Removal of the N-terminal amino acid residue together with the PTM (*) by a first Edman-type degradation may result in the first affinity reagent showing substantially less affinity to the shortened polypeptide to the extent that it would be considered to be non-binding to this epitope. At the same time, a second affinity reagent may show substantial binding to one of the first Edman-type degradation intermediate products but show negligible binding to the polypeptide prior to performing the first Edman-type reaction. FIGS. 14B and 14C may show similar losses of binding affinity to the same or different affinity reagents after the first Edman degradation reaction where the PTM resides within the binding epitope region of a first affinity reagent (contiguous epitope). FIG. 14D may also show the same trend even though the PTM is on amino acid residue number 10 (side chain=S10) as the polypeptide may fold in such a manner where the S10 side-chain in the tertiary or quaternary structure of the polypeptide may be in close proximity to the first three amino acid residues as part of a non-contiguous epitope for the first affinity reagent.

Referring to FIG. 14E where there is no PTM near the first three residues of the polypeptide, either contiguous or non-contiguous, this polypeptide may not show a substantial change in binding (or non-binding) for the first affinity reagent either before or after a first Edman-type sequencing reaction. In the case of FIG. 14E, a second affinity reagent which may bind to the S6 region of the polypeptide (remote from the first amino acid residue) may show little or no change in binding when compared to both before and after the first Edman-type sequencing reaction for the first amino acid residue.

Affinity reagents described herein may be used in combination with other chemical reagents which may be used to modify proteoforms of polypeptides, for example, dansyl chloride is a chemical reagent used to modify protein amino groups including N-termini (Walker, J. M., Methods Mol Biol. 1984; (1) 203-12. doi: 10.1385/0-89603-062-8:203). Affinity reagents may be used before, after, or both before and after such chemical modifications to further characterize proteoforms of polypeptides. For example, an array including a plurality of polypeptides may have a first proteoform of a polypeptide including an N-terminal phosphotyrosine residue. The polypeptide may have a second proteoform with a phosphotyrosine amino acid residue remote from its N-terminus. A first affinity reagent having a first detectable label may bind to the first proteoform of the polypeptide but not to the second proteoform of the polypeptide. A second affinity reagent having a second detectable label may bind to the second proteoform of the polypeptide and not to the first proteoform of the polypeptide. The two proteoforms of the polypeptide may be characterized by analyzing signals from the first and second affinity reagents binding to their respective first and second proteoforms of the polypeptide. Further characterization may be performed by employing one or more steps using dansyl chloride. After contacting the array with first and second affinity reagents and detecting corresponding binding signals, dansyl chloride may be introduced to the array. This may label all polypeptide N-termini with a dansyl group. Acid hydrolysis of the array yields a mixture of free amino acids plus dansyl amino acid derivatives of N-terminal amino acids. These may be detected using immobilized or free affinity reagents, for example, including FRET fluorescent groups which interact with the fluorescent dansyl group. The affinity reagents to N-terminal dansyl groups may be immobilized on solid supports, surfaces or beads and detected by, for example, fluorescence activated cell sorting. The beads may be tagged or barcoded, for example, with DNA barcodes that can be cleaved and amplified by PCR and used to quantification of the captured affinity reagent.

In some cases, Edman-type reactions may be thwarted by N-terminal modifications which may be selectively removed, for example, N-terminal acetylation or formylation (e.g., see Gheorghe M. T., Bergman T. (1995) in Methods in Protein Structure Analysis, Chapter 8: Deacetylation and internal cleavage of Polypeptides for N-terminal Sequence Analysis. Springer, Boston, MA https://doi.org/10.1007/978-1-4899-1031-8_8).

Polypeptide isoforms can also be detected based on their enzymatic or other biological activity. For example, a polypeptide isoform can be contacted with a reactant that is converted to a detectable product by an enzymatic activity of the polypeptide isoform. In other assay formats, a first polypeptide having a known enzymatic function can be contacted with a second polypeptide to determine if the second polypeptide changes the enzymatic function of the first polypeptide. As such, the first polypeptide serves as a reporter system for detection of the second polypeptide. Exemplary changes that can be observed include, but are not limited to, activation of the enzymatic function, inhibition of the enzymatic function, degradation of the first polypeptide or competition for a reactant or cofactor used by the first polypeptide. The first polypeptide can be a proteoform having an activity that differs from another proteoform of the first polypeptide. For example, the proteoform can have a different affinity for the second polypeptide compared to the affinity of another proteoform of the first polypeptide. The second polypeptide can be a proteoform having an activity that differs from another proteoform of the second polypeptide. For example, the proteoform can have a different affinity for the first polypeptide compared to the affinity of another proteoform of the second polypeptide.

In some configurations of the polypeptide detection methods set forth herein, the polypeptides can be detected on a solid support. For example, polypeptides can be attached to a support, the support can be contacted with affinity reagents in solution, the affinity reagents can interact with the polypeptides, thereby producing a detectable signal, and then the signal can be detected to determine the presence of the polypeptides. In multiplexed versions of this approach, different polypeptides (e.g., one or more different proteoforms of a particular polypeptide species) can be attached to different addresses in an array, and the probing and detection steps can occur in parallel. In another example, affinity reagents can be attached to a solid support, the support can be contacted with polypeptides in solution, the polypeptides can interact with the affinity reagents, thereby producing a detectable signal, and then the signal can be detected to determine the presence of the polypeptides. This approach can also be multiplexed by attaching different affinity reagents to different addresses of an array. In yet another approach, polypeptides can be detected using mass spectrometry methods. Several exemplary detection methods are set forth below and elsewhere herein. It will be understood that other detection methods can also be used.

Typical polypeptide detection methods, such as enzyme linked immunosorbent assay (ELISA), achieve high-confidence characterization of one or more polypeptide in a sample by exploiting high specificity binding of antibodies, aptamers or other binding reagents to the polypeptide(s) and detecting the binding event while ignoring all other polypeptides in the sample. ELISA is generally carried out at low plex scale (e.g. from one to several hundred different polypeptides detected in parallel or in succession) but can be used at higher plexity.

ELISA methods can be carried out by detecting immobilized binding reagents and/or polypeptides in multiwell plates, detecting immobilized binding reagents and/or polypeptides on arrays, or detecting immobilized binding reagents and/or polypeptides on particles in microfluidic devices. ELISA methods can be used to distinguish one or more proteoforms in a method or system set forth herein. Exemplary plate-based methods include, for example, the MULTI-ARRAY technology commercialized by MesoScale Diagnostics (Rockville, Maryland) or Simple Plex technology commercialized by Protein Simple (San Jose, California). Exemplary, array-based methods include, but are not limited to those utilizing SimoaÒ Planar Array Technology or SimoaÒ Bead Technology, commercialized by Quanterix (Billerica, MA). Further exemplary array-based methods are set forth in U.S. Pat. Nos. 9,678,068; 9,395,359; 8,415,171; 8,236,574; or 8,222,047, each of which is incorporated herein by reference. Exemplary microfluidic detection methods include those commercialized by Luminex (Austin, Texas) under the trade name xMAPÒ technology or used on platforms identified as MAGPIXÒ, LUMINEXÒ 100/200 or FEXMAP 3DÒ. In some embodiments, methods described herein for assaying proteoforms of polypeptides may be used to further confirm the results of Elisa methods. In other embodiments Elisa methods may be used to further confirm or add to the confidence of results using proteoform methods described herein. In other embodiments, combinations of the proteoform methods described herein in combination with Elisa methods may be used with advantage to detect, identify and/or quantitate polypeptide proteoforms.

Other detection methods that can also be used to identify proteoforms, and that are particularly useful at low plex scale include procedures that employ SOMAmer reagents and SOMAscan assays commercialized by SomaLogic (Boulder, CO). In one configuration, a sample is contacted with aptamers that are capable of binding polypeptides with high specificity for the amino acid sequence and/or PTMs of the polypeptides. The resulting aptamer-polypeptide complexes can be separated from other sample components, for example, by attaching the complexes to beads that are removed from the sample. The aptamers can then be isolated and, because the aptamers are nucleic acids, the aptamers can be detected using any of a variety of methods known in the art for detecting nucleic acids, including for example, hybridization to nucleic acid arrays, PCR-based detection, or nucleic acid sequencing. Exemplary methods and compositions for use in an aptamer-based or other detection method set forth herein are set forth in U.S. Pat. Nos. 8,404,830; 8,975,388; 9,163,056; 9,938,314; 10,239,908; 10,316,321 or 10,221,207. Further examples are set forth in U.S. Pat. Nos. 7,855,054; 7,964,356; 8,975,026; 8,945,830; 9,404,919; 9,926,566; 10,221,421; 10,316,321 or 10,392,621. The above patents are incorporated herein by reference. Methods described herein may be used in combination with SOMAmer reagents or with SOMAscan assays.

Polypeptides (e.g., one or more isoforms of a particular polypeptide species) can also be detected based on proximity of two or more affinity reagents. For example, two affinity reagents can each include a receptor component and a nucleic acid component. When the affinity reagents bind in proximity to each other, for example, due to ligands (e.g. post-translationally modified amino acid residues or non-modified residues, respectively) for the respective receptors being on a single polypeptide, or due to the ligands (e.g. post-translationally modified amino acid residues or non-modified residues, respectively) being present on two polypeptides that associate with each other, the nucleic acids can interact to cause a modification that is indicative of the proximity. For example, one of the nucleic acids can be extended using the other nucleic acid as a template, one of the nucleic acids can form a template that positions the other nucleic acid for ligation to another nucleic acid, or the like. Exemplary methods are commercialized by Olink Proteomics AB (Uppsala Sweden) or set forth in U.S. Pat. Nos. 7,306,904; 7,351,528; 8,013,134; 8,268,554 or 9,777,315, each of which is incorporated herein by reference.

A method of detecting a polypeptide, can include a step of detecting a polypeptide proteoform (e.g., a polypeptide proteoform conjugate) and/or detecting an internal standard polypeptide (e.g., a standard polypeptide conjugate). In one configuration, detection can include steps of (i) contacting a first set of binding reagents with a polypeptide proteoform, and/or an internal standard polypeptide, and (ii) detecting binding of the polypeptide proteoform and/or internal standard polypeptide to a binding reagent in the second set of binding reagents. The method can optionally include one or more of the further steps of (iii) removing the first set of binding reagents, (iv) binding a second set of binding reagents to the polypeptide proteoform, and/or the internal standard polypeptide, wherein binding reagents in the second set are different from binding reagents in the first set, and (v) detecting binding of the polypeptide proteoform and/or internal standard polypeptide to a binding reagent in the second set of binding reagents. The method can optionally be carried out for one or more polypeptides proteoforms in an array or internal standard polypeptides.

High specificity binding reagents can be useful in a number of polypeptide detection methods. Alternatively, detection can be based on multiple low specificity detection cycles that are performed on a sample such that the individual cycles may detect multiple polypeptides while not necessarily distinguishing one of the detected polypeptides from another in any one of the cycles. For example, the multiple separate measurements can include subjecting the sample to reagents that are promiscuous with regard to recognizing multiple components of the sample. However, using compositions and methods set forth herein, results from multiple cycles can be combined to achieve high-confidence quantification, identification or characterizations of a plurality of individual polypeptides in the sample. Accordingly, a first measurement carried out using a first promiscuous reagent may perceive a first subset of sample components without distinguishing one component from another. A second measurement carried out using a second promiscuous reagent may perceive a second subset of sample components, again, without distinguishing one component from another. However, a comparison of the first and second measurements can distinguish: (i) a sample component that is uniquely present in the first subset but not the second; (ii) a sample component that is uniquely present in the second subset but not the first; (iii) a sample component that is uniquely present in both the first and second subsets; or (iv) a sample component that is uniquely absent in the first and second subsets. Accordingly, one or more of the individual cycles yield ambiguous results with regard to distinguishing the identity of a subset of polypeptides that produce detectable signal; however, characterizing the signals across the multiple cycles allows individual polypeptides to be individually and unambiguously identified. The resulting set of identified polypeptides can be larger than the number of polypeptides that produce signal from any of the individual cycles.

Some configurations of detection methods that are based on multiple low specificity detection cycles may be understood, to some extent, via analogies to the children's game "20 Questions." An objective of this game is to identify a target answer in as few questions as possible. An effective tactic is to ask questions on characteristics ranging from broad characteristics (e.g., "Is it a person, place, or thing?", "Is the person in this room?") to narrow characteristics (e.g., "Is the person named 'Jamie'?"). In general, it is possible to identify a character in the game by asking substantially fewer questions (N) than the possible number of answers (M), i.e., N<<M. By analogy, affinity reagents used in some configurations of the detection methods set forth herein, may have a broad range of interactions with respect to a population of polypeptides. For example, an affinity reagent may be considered to be a 'promiscuous' affinity reagent due to its affinity for a single epitope that is present in a plurality of different polypeptides in a sample, or due to its affinity for a plurality of different epitopes that are present in one or more polypeptides in the sample. By testing for the interaction of an affinity reagent with a polypeptide, information is acquired regardless of whether an interaction is observed. For example, a failure of an affinity reagent to bind a polypeptide is indicative of the polypeptide lacking the epitope for the affinity reagent.

In the above-described analogy of 20 Questions, the outcome is based upon clear articulation of queries and answers, and is also based upon accurate and reliable answers (e.g., type, size, attributes, etc.). By analogy, polypeptide characterization by the measurement of affinity reagent interactions may be more difficult when the measurements are prone to a degree of systematic or random error or uncertainty. For example, measurement accuracy of affinity reagent (e.g., antibody) interactions with binding targets (e.g. epitopes) may be affected by numerous factors such as system detection limits or sensitivity, non-specific interactions between epitopes and affinity reagents (false positives), or stochastic, time-dependent reversal of an interaction (false negatives).

It is not uncommon for polypeptide characterization measurements to contain a degree of uncertainty. High-confidence characterization may be achieved by utilizing multiple low specificity detection cycles in combination with a probabilistic decoding approach. The overlaying or combining of binary polypeptide interaction data (e.g., affinity reagent A1, which interacts with epitope X, was not observed to interact with unknown polypeptide P, therefore, polypeptide P does not contain epitope X) may lead to improper polypeptide characterization due to the inclusion or exclusion of possible candidate states due to measurement error. By contrast, overlaying or combining probabilistic polypeptide interaction data may permit an algorithm to converge to a high-confidence prediction of polypeptide identity without needing to exclude any candidate states. For example, if affinity reagents A1 to A6 are known to interact with a known polypeptide P1 with interaction probabilities, and measurable interactions of affinity reagents A2, A5 and A6 are observed against an unknown polypeptide P, it may be concluded that polypeptide P is likely not polypeptide P1 (2 of 3 likely interactions were not observed; 2 of 3 unlikely interactions were observed). Moreover, a probability-based characterization may be assigned a degree of confidence such that a prediction for each observed polypeptide may be made when the degree of confidence rises above a threshold degree of confidence. For example, in the above observation of polypeptide P, the six described observations may not provide a high enough degree of confidence to eliminate polypeptide P1 as a possible identity, but similar trends over 20 or more affinity reagents may provide sufficient degree of confidence to eliminate P1 as a possible identity. Accordingly, polypeptide P1 can be subjected to binding reactions with a series of promiscuous affinity reagents, and although the observation from each binding reaction taken individually may be ambiguous with regard to identifying the polypeptide, decoding the observations from the series of binding reactions may identify polypeptide P1 with an acceptable level of confidence.

A polypeptide detection assay that is based on multiple low specificity detection cycles may be configured to permit polypeptide characterization at an individual or single-molecule level. Polypeptides to be characterized may be provided on a solid support containing unique, detectably resolvable characterization sites. Such characterization sites may be spaced, arrayed, or otherwise ordered to allow individual sites to be distinguished one from another when detecting their interactions with affinity reagents. A solid support may include a sufficient number of unique, optically resolvable characterization sites to accommodate a plurality, majority, or all polypeptides from a sample, such as at least about $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, or more than $1 \times 10^{12}$ sites. Each site may contain a known number of polypeptides that are to be characterized. In some cases, a characterization site may contain a single polypeptide molecule to be detected, identified or characterized. In other cases, a site may contain multiple polypeptide molecules, with at least one molecule to be detected. For example, the polypeptide molecule to be detected can be one subunit in a larger protein having multiple different subunits.

In some cases, polypeptide detection assays that are based on multiple low specificity detection cycles may utilize affinity reagents such as antibodies (or functional fragments thereof), aptamers, mini protein binders, or any other suitable binding reagent. Affinity reagents may be promiscuous affinity reagents that possess a likelihood to interact with (e.g., bind to) more than one polypeptide in a sample. In some cases, the affinity reagents may possess a likelihood to interact with two or more unique, structurally dissimilar proteins in a sample. For example, an affinity reagent may bind with near-equal probability to a particular membrane protein and a particular cytoplasmic protein based upon a region of structural similarity. In some cases, a binding affinity reagent may possess a likelihood of binding to a particular amino acid epitope or family of epitopes regardless of the sequence context (e.g., amino acid sequence upchain and/or downchain from the epitope).

An affinity reagent that is used for multiple low specificity detection cycles may be characterized such that it has an identified, determined, or assessed probability-based binding profile. An affinity reagent may have the property of binding to a first polypeptide with an identified, determined, or assessed binding probability of greater than about 50% (e.g., at least about 50%, 60%, 70%, 80%, 90%, 95%, 99%, 99.9%, 99.99%, 99.999% or greater than about 99.999%) and binding to a second structurally non-identical polypeptide with an identified, determined, or assessed binding probability of less than about 50% (e.g., no more than about 50%, 40%, 30%, 20%, 10%, 5%, 1%, 0.1%, 0.01%, 0.001% or less than about 0.001%). In a particular case, the difference in observed binding probabilities of the affinity reagent to the first and second polypeptides may be due to the presence, absence, or inaccessibility of a particular epitope or family of epitopes in either the first or second polypeptide. Probabilistic affinity reagent binding profiles may be determined or identified by in vitro measurements or in silico predictions.

Polypeptide detection methods that are based on multiple low specificity detection cycles may further incorporate computational decoding approaches that are optimized for the above-described affinity reagents. The decoding approaches may overlay or combine data from multiple rounds of detecting affinity reagent interaction with individual polypeptides and can assign a degree of confidence for detection of signal from each polypeptide. For example, affinity reagent interactions can be detected for each site in an array of sites, and a degree of confidence can be assigned to detection of each signal at each site. Similarly, a degree of confidence can be assigned to a series of detection events at each site. A polypeptide may be considered identified or characterized if the degree of confidence for a prediction based upon overlayed or combined affinity reagent interaction data exceeds a threshold degree of confidence. The threshold degree of confidence for a polypeptide characterization prediction may depend upon the nature of the characterization. The threshold degree of confidence may fall in a range from about 50% to about 99.999%, such as about 50%, 60%, 70%, 80%, 90%, 95%, 99%, 99.99%, or about 99.999%. In some cases, the threshold degree of confidence may be outside this range. In some cases, the computational decoding approaches may incorporate machine learning or training algorithms to update or refine the determined or identified probabilistic interaction profile for the affinity reagents or polypeptides with increased information or in ever widening contexts.

Methods set forth herein, can be configured to (1) use promiscuous affinity reagents that bind to multiple different candidate polypeptides suspected of being present in a given sample, and (2) subject a plurality of unknown polypeptides to a set of promiscuous affinity agents that, taken as a whole, are expected to bind each candidate polypeptide in a different combination, such that each candidate polypeptide is expected to be encoded by a unique profile of binding and non-binding events. Promiscuity of an affinity reagent is a characteristic that can be understood relative to a given population of polypeptides. Promiscuity can arise due to the affinity reagent recognizing an epitope that is known to be present in a plurality of different candidate polypeptides suspected of being present in a given population of unknown polypeptides. For example, epitopes having relatively short amino acid lengths such as dimers, trimers, or tetramers can be expected to occur in a substantial number of different polypeptides in the human proteome. Alternatively or additionally, a promiscuous affinity reagent can recognize different epitopes (e.g. epitopes differing from each other with regard to amino acid composition or sequence), the different epitopes being present in a plurality of different candidate polypeptides. For example, a promiscuous affinity reagent that is designed or selected for its affinity toward a first trimer epitope may bind to a second epitope that has a different sequence of amino acids when compared to the first epitope.

Although performing a single binding reaction between a promiscuous affinity reagent and a complex polypeptide sample may yield ambiguous results regarding the identity of the different polypeptides to which it binds, the ambiguity can be resolved when the results are combined with other identifying information about those polypeptides. The identifying information can include characteristics of the polypeptide such as length (i.e. number of amino acids), hydrophobicity, molecular weight, charge to mass ratio, isoelectric point, chromatographic fractionation behavior, enzymatic activity, presence or absence of post translational modifications or the like. The identifying information can include results of binding with other promiscuous affinity reagents. For example, a plurality of different promiscuous affinity reagents can be contacted with a complex population of unknown polypeptides, wherein the plurality of affinity reagents is configured to produce a different binding profile for each candidate polypeptide suspected of being present in the population of unknown polypeptides. In this example, each of the affinity reagents can be distinguishable from the other affinity reagents, for example, due to unique labeling (e.g. different affinity reagents having different luminophore labels), unique spatial location (e.g. different affinity reagents being located at different addresses in an array), and/or unique time of use (e.g. different affinity reagents being delivered in series to a population of proteins). Accordingly, the plurality of promiscuous affinity reagents produces a binding profile for each individual protein that can be decoded to identify a unique combination of epitopes present in the individual polypeptide, and this can in turn be used to identify the individual polypeptide as a particular candidate polypeptide having the same or similar unique combination of epitopes. The binding profile can include observed binding events as well as observed non-binding events and this information can be evaluated in view of the expectation that particular candidate polypeptides produce a similar binding profile, for example, based on presence and absence of particular epitopes in the candidate polypeptides.

In some configurations, distinct and reproducible binding profiles may be observed for one or more unknown polypeptides in a sample. However, in many cases one or more binding events produces inconclusive or even aberrant results and this, in turn, can yield ambiguous binding profiles. For example, observation of binding outcome for a single-molecule binding event can be particularly prone to ambiguities due to stochasticity in the behavior of single molecules when observed using certain detection hardware. The present disclosure provides methods that provide accurate polypeptide identification despite ambiguities and imperfections that can arise in many contexts. In some configurations, methods for identifying, quantitating or otherwise characterizing one or more polypeptides in a sample utilize a binding model that evaluates the likelihood or probability that one or more candidate polypeptides that are suspected of being present in the sample will have produced an empirically observed binding profile. The binding model can include information regarding expected binding outcomes (e.g. binding or non-binding) for binding of one or more affinity reagent with one or more candidate polypeptides. The information can include an a priori characteristic of a candidate polypeptide, such as presence or absence of a particular epitope in the candidate polypeptide or length of the candidate polypeptide. Alternatively or additionally, the information can include empirically determined characteristics such as propensity or likelihood that the candidate polypeptide will bind to a particular affinity reagent. Accordingly, a binding model can include information regarding the propensity or likelihood of a given candidate polypeptide generating a false positive or false negative binding result in the presence of a particular affinity reagent, and such information can optionally be included for a plurality of affinity reagents.

Methods set forth herein can be used to evaluate the degree of compatibility of one or more empirical binding profiles with results computed for various candidate polypeptides using a binding model. For example, to identify an unknown polypeptide in a sample of many polypeptides, an empirical binding profile for the polypeptide can be compared to results computed by the binding model for many or all candidate polypeptides suspected of being in the sample. In some configurations of the methods set forth herein, identity for the unknown polypeptide is determined based on a likelihood of the unknown polypeptide being a particular candidate protein given the empirical binding pattern or based on the probability of a particular candidate polypeptide generating the empirical binding pattern. Optionally a score can be determined from the measurements that are acquired for the unknown polypeptide with respect to many or all candidate polypeptides suspected of being in the sample. A digital or binary score that indicates one of two discrete states can be determined. In particular configurations, the score can be non-digital or non-binary. For example, the score can be a value selected from a continuum of values such that an identity is made based on the score being above or below a threshold value. Moreover, a score can be a single value or a collection of values. Particularly useful methods for identifying polypeptides using promiscuous reagents, serial binding measurements and/or decoding with binding models are set forth, for example, in U.S. Pat. No. 10,473,654 US Pat. App. Pub. No. 2020/0318101 A1 or Egertson et al., BioRxiv (2021), DOI: 10.1101/2021.10.11.463967, each of which is incorporated herein by reference.

A method of detecting a polypeptide, can include a process of detecting a polypeptide proteoform and/or detecting an internal standard polypeptide, the process including steps of (i) binding a first binding reagent to a polypeptide proteoform, and/or an internal standard polypeptide, at an address of an array, wherein the binding reagent includes a nucleic acid tag, and wherein a primer nucleic acid is present at the address; (ii) extending the primer nucleic acid, thereby producing an extended primer having a copy of the tag; and (iii) detecting the tag of the extended primer. The extending of the primer can be carried out, for example, by polymerase based extension of the primer, using the nucleic acid tag as a template. Alternatively, the extending of the primer can be carried out, for example, by ligase or chemical based ligation of the primer to a nucleic acid that is hybridized to the nucleic acid tag. The nucleic acid tag can be detected via hybridization to nucleic acid probes (e.g., in a microarray), amplification-based detections (e.g., PCR-based detection, or rolling circle amplification-based detection) or nucleic acid sequencing (e.g., cyclical reversible terminator methods, nanopore methods, or single molecule, real time detection methods). Exemplary methods that can be used for detecting polypeptides using nucleic acid tags are set forth in US Pat. App. Pub. No. 2019/0145982 A1; 2020/0348308 A1; or 2020/0348307 A1, each of which is incorporated herein by reference.

A method of detecting a polypeptide, can include a process of detecting a polypeptide proteoform and/or detecting an internal standard polypeptide, the process including steps of (i) exposing a terminal amino acid on the polypeptide; (ii) detecting a change in signal from the polypeptide; and (iii) identifying the type of amino acid that was removed based on the change detected in step (ii). The terminal amino acid can be exposed, for example, by removal of one or more amino acids from the amino terminus or carboxyl terminus of the polypeptide. Steps (i) through (iii) can be repeated to produce a series of signal changes that is indicative of the sequence for the polypeptide. Optionally, one or more different polypeptides can be attached at respective addresses of a polypeptide array. The signal change can optionally be detected at one or more address on an array.

In a first configuration of the above method, one or more types of amino acids in the polypeptide can be attached to a label that uniquely identifies the type of amino acid. In this configuration, the change in signal that identifies the amino acid can be loss of signal from the respective label. Exemplary compositions and techniques that can be used to remove amino acids from a polypeptide and detect signal changes are set forth in Swaminathan et al., Nature Biotech. 36:1076-1082 (2018); or U.S. Pat. No. 9,625,469 or 10,545,153, each of which is incorporated herein by reference.

In a second configuration of the above method, the terminal amino acid of the polypeptide can be recognized by a binding reagent that is specific for the terminal amino acid or specific for a label moiety that is present on the terminal amino acid. The binding reagent can be detected on the array, for example, due to a label on the binding reagent. Exemplary binding reagents and detection methods are set forth in US Pat. App. Pub. No. 2019/0145982 A1; 2020/0348308 A1; or 2020/0348307 A1, each of which is incorporated herein by reference A method of detecting a polypeptide can include a process of detecting a polypeptide proteoform of an array of polypeptides and/or detecting an internal standard polypeptide of an array of polypeptides, the process including steps of (i) exposing a terminal amino acid on a polypeptide at an address of an array; (ii) binding a binding reagent to the terminal amino acid, wherein the binding reagent includes a nucleic acid tag, and wherein a primer nucleic acid is present at the address; (iii) extending the primer nucleic acid, thereby producing an extended primer having a copy of the tag; and (iv) detecting the tag of the extended primer. The terminal amino acid can be exposed, for example, by removal of one or more amino acids from the amino terminus or carboxyl terminus of the polypeptide. Steps (i) through (iv) can be repeated to produce a series of tags that is indicative of the sequence for the polypeptide. The extending of the primer can be carried out, for example, by polymerase-based extension of the primer, using the nucleic acid tag as a template. Alternatively, the extending of the primer can be carried out, for example, by ligase- or chemical-based ligation of the primer to a nucleic acid that is hybridized to the nucleic acid tag. The nucleic acid tag can be detected via hybridization to nucleic acid probes (e.g., in a microarray), amplification-based detections (e.g., PCR-based detection, or rolling circle amplification-based detection) or nucleic acid sequencing (e.g., cyclical reversible terminator methods, nanopore methods, or single molecule, real time detection methods). Exemplary methods that can be used for detecting polypeptides using nucleic acid tags are set forth in US Pat. App. Pub. No. 2019/0145982 A1; 2020/0348308 A1; or 2020/0348307 A1, each of which is incorporated herein by reference.

A method of detecting a polypeptide, such as a proteoform, can include determining a detected property such as a sequence of amino acids, presence of a known epitope, polypeptide size, polypeptide isoelectric point, polypeptide hydrophobicity, polypeptide hydrodynamic radius, polypeptide pKa, the presence of a PTM, the absence of a PTM, polypeptide charge, the presence of a non-natural amino acid or other non-natural amino acid chemical unit, the presence of secondary, tertiary, or quaternary structure, the absence of secondary, tertiary, or quaternary structure, presence of a bound molecule, or absence of a bound molecule. A bound non-polypeptide molecule may include a chelated ion, a bound metal cluster, a bound cofactor (e.g., a porphyrin), a bound ligand, a bound substrate, or a bound biomolecule (e.g., polysaccharide, nucleic acid, protein, etc.).

Figure 5:
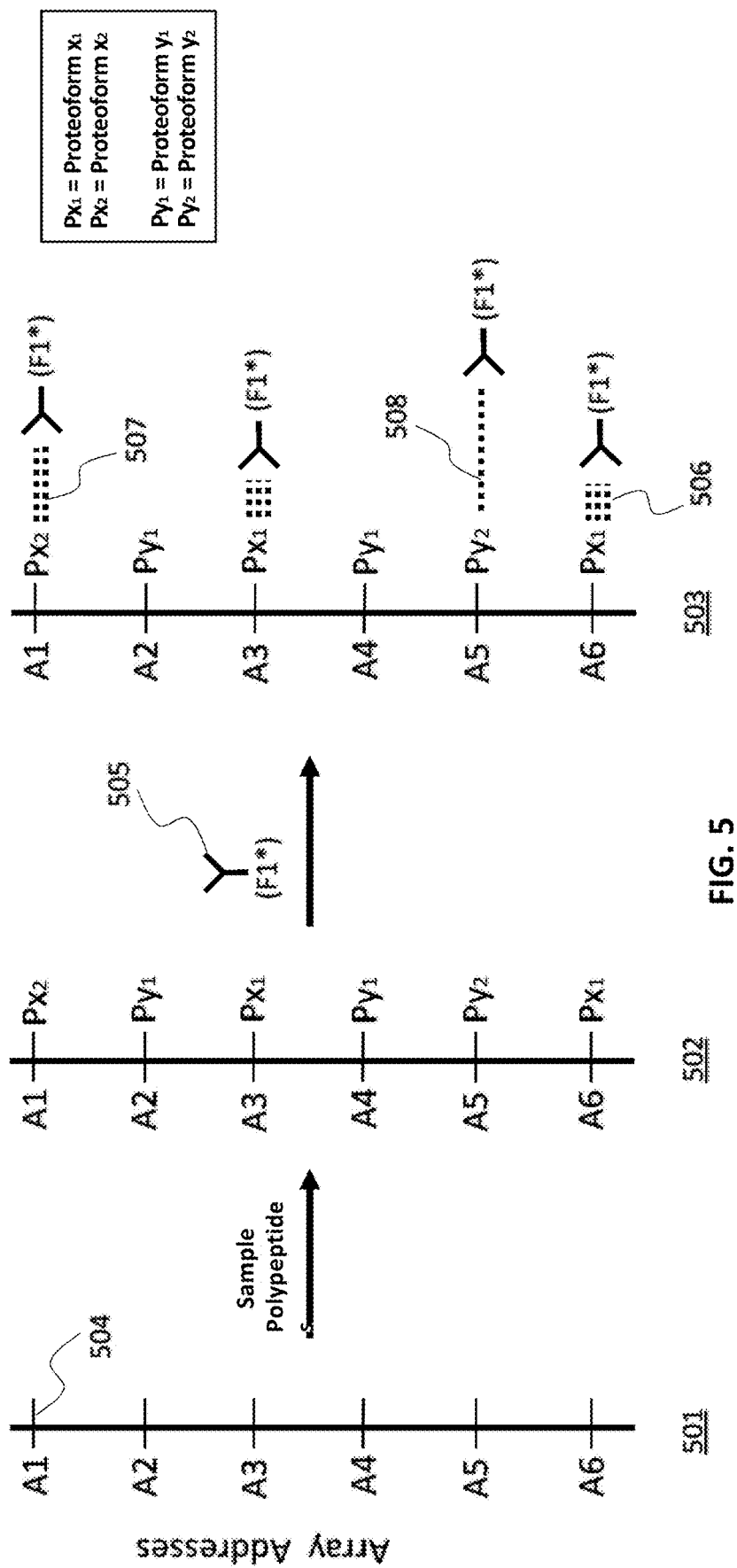
FIG. 5 shows an affinity reagent probing two sets of two different proteoform pairs (Px1, Px2 and Py1, Py2) attached to an addressable array.

Affinity reagents may bind to more than one proteoform of a polypeptide in an array and may also bind to two or more different polypeptides. FIG. 5 illustrates an affinity reagent 505 probing two sets of two different proteoform pairs (Px1, Px2 and Py1, Py2) attached to an addressable array 501. The array has unique addresses A1-A6, each with anchoring groups 504. Proteoforms Px1 and Px2 (proteoforms of a Px polypeptide) and proteoforms Py1 and Py2 (proteoforms of a Py polypeptide) are shown bound individually at addresses A1-A6 in assembly 502. A first affinity reagent 505, known to have different probabilities of binding to Px1, Px2 and Py2, is added to array 502 contacting all proteoforms on the array, and is shown to bind to the proteoforms with decreasing probabilities (506, 507 and 508 respectively, short triple dotted line where 506 has the higher probability of binding and the single longest dotted line where 508 has the lower probability of binding) is shown in assembly 503. Different sets of proteoforms, for example, the Px set (Px1 and Px2) and the Py set (Py1 and Py2) may have the same, similar or very different probabilities of binding to the same affinity reagent. The asterisk on affinity reagent 505 (F1*) denotes that it has an optional detectable label.

Figure 6:
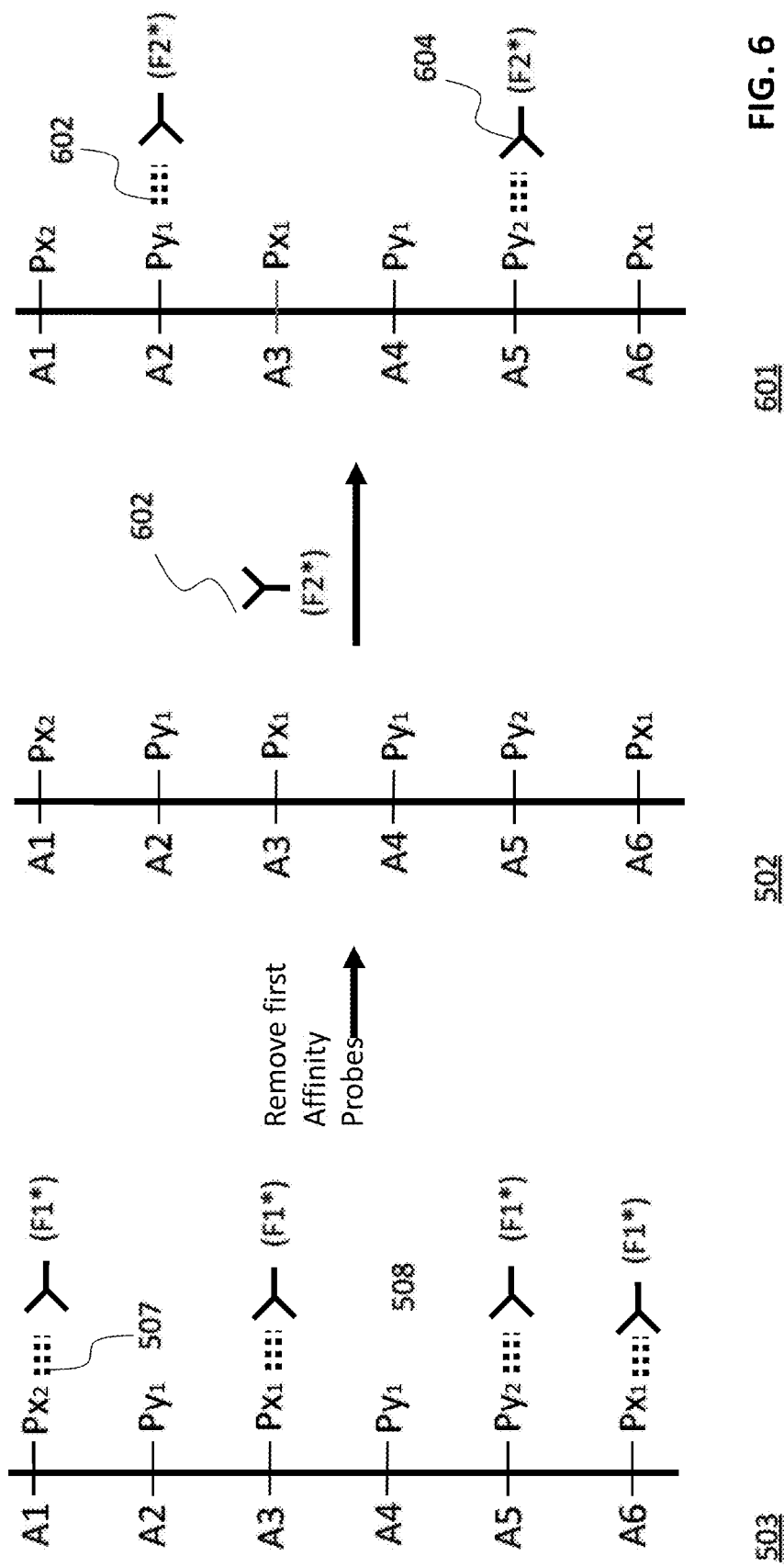
FIG. 6 shows a first set of affinity reagents (F1*) being removed and a second set of affinity reagents (F2*) being introduced to the addressable array.

Removal of the first affinity reagent 505 from assembly 503 regenerates array 502 having no bound affinity reagents, FIG. 6. Addition of a second affinity reagent 602 known to bind to Py1 and Py2 but not to Px1 or Px2 is shown in assembly 601.

Figure 7:
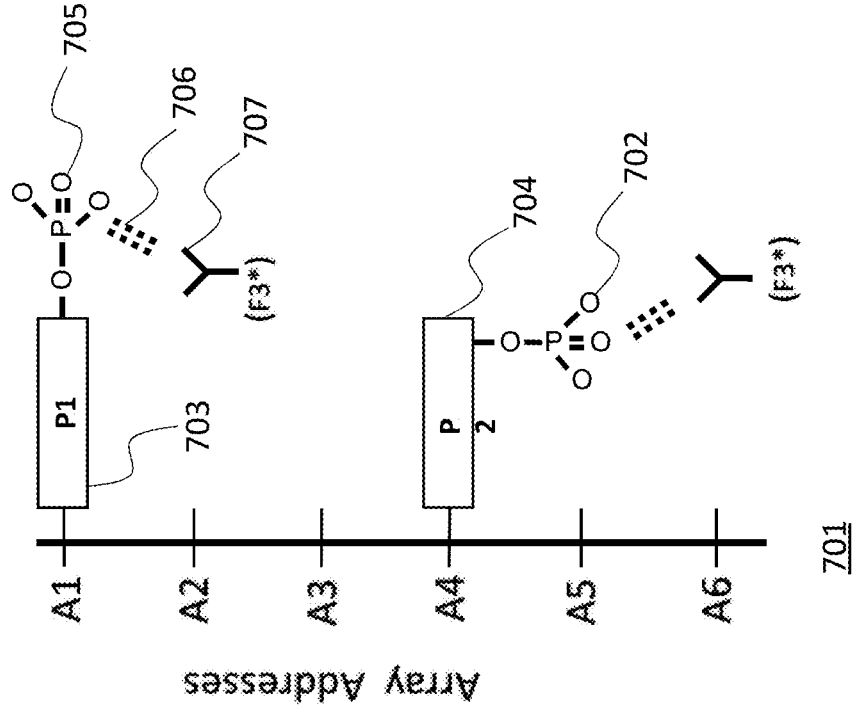
FIG. 7 shows a third affinity reagent (F3*) binding only to the phosphate group of two different phosphorylated polypeptides.

Affinity reagents may bind only to a PTM of a proteoform, for example, only to phosphate groups 702 and 705 in phosphorylated proteoforms P1 and P2 shown in FIG. 7. The affinity reagent does not bind to non-phosphorylated proteoforms of polypeptides 703 or 704.

Figure 8:
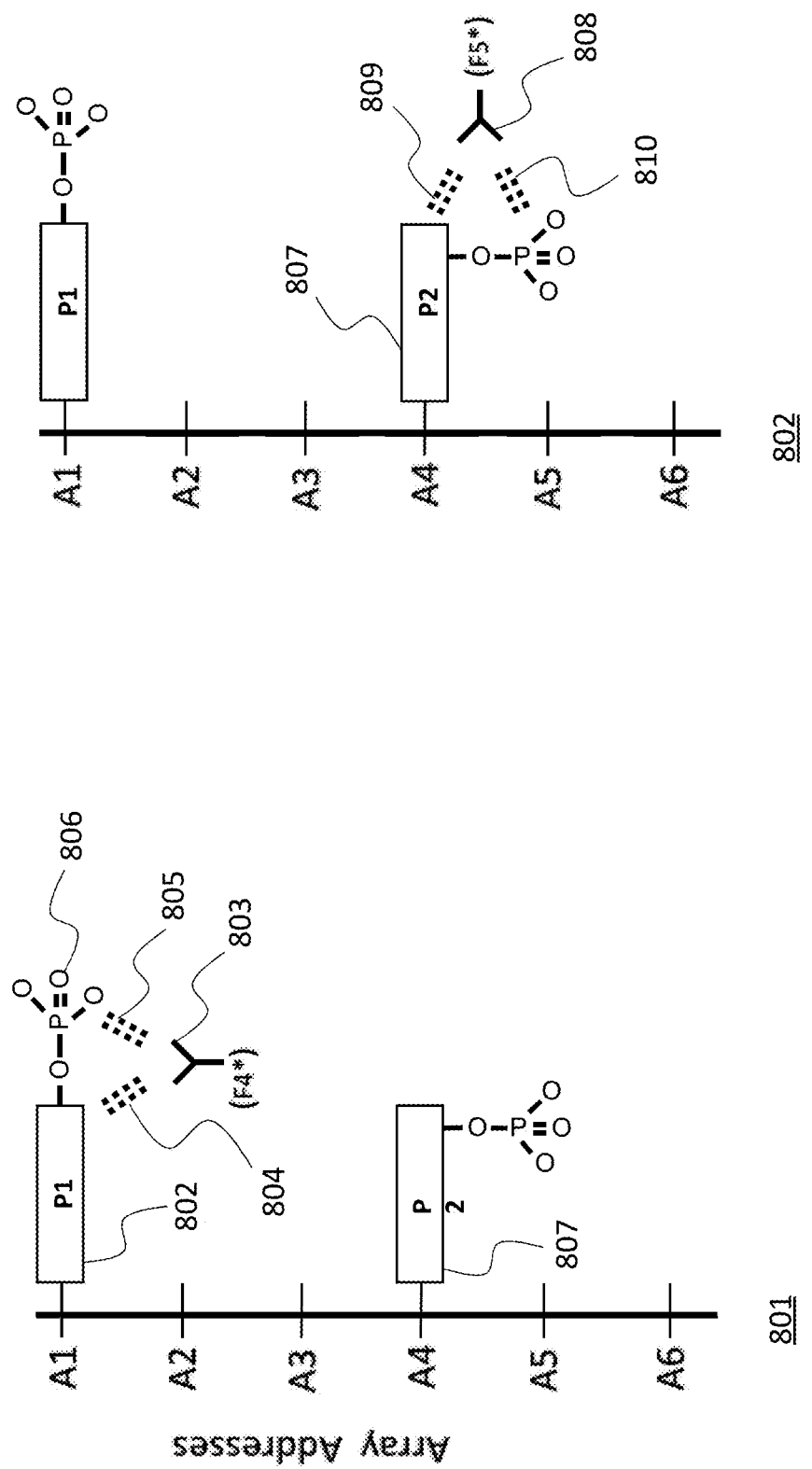
FIG. 8 shows two different affinity reagents (F4* and F5*) binding to two different proteoforms where both reagents are binding to phosphate groups and to the polypeptides (P1 and P2).

Alternatively, affinity reagents may bind to both a PTM, for example, a phosphate group in a phosphorylated proteoform, and to regions of the polypeptide which are close to the phosphate group as shown in FIG. 8. Assembly 801 shows affinity reagent 803 binding to both phosphate group 806 through affinity bond 805 and to the polypeptide 802 through affinity bond 804. Affinity reagent 803 has no apparent affinity for proteoform P2 in assembly 801. Similarly, affinity reagent 808 is shown binding to proteoform P2 in assembly 802 by both a PTM phosphate group and by polypeptide 807. Assemblies 801 and 802 demonstrate two different affinity reagents 803 and 808 respectively having binding specificities for two different proteoforms P1 and P2 respectively, and both binding to their respective polypeptide moieties and to the PTM moieties. In some configurations of the methods set forth herein, affinity reagents may bind only to polypeptides moieties of proteoforms and not to the PTM moieties.

Figure 9:
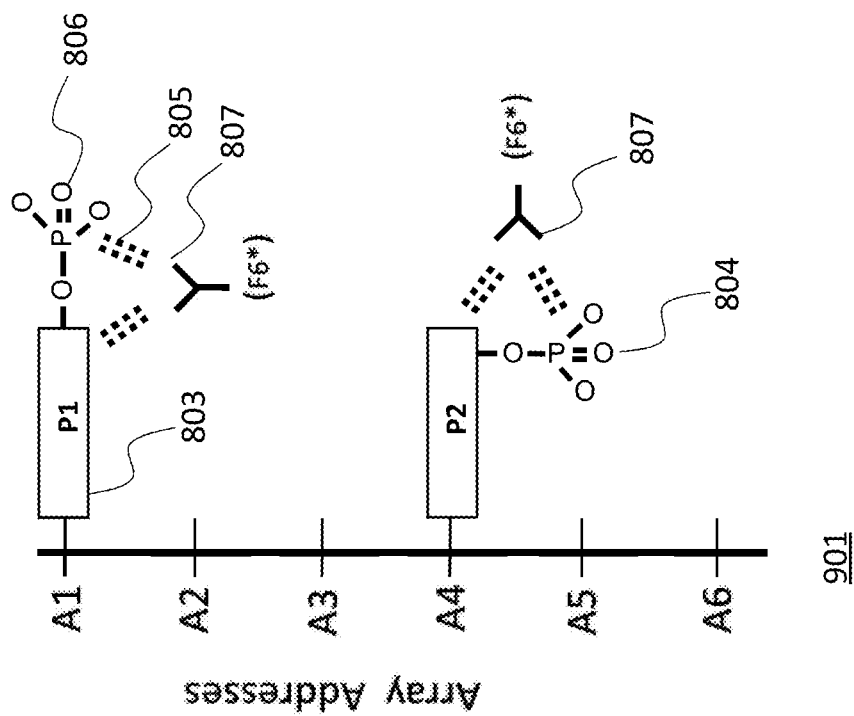
FIG. 9 shows an affinity reagent (F6*) binding to two different proteoforms by both their phosphate groups and by their polypeptides.

FIG. 9 demonstrates that a single affinity reagent 807 may bind to proteoforms of two different polypeptides P1 and P2. Affinity reagent 807 is shown binding to both the polypeptide moieties and to the PTM phosphate moieties of P1 and P2.

Fluorescent labels on affinity reagents may be "on" all the time, for example, standalone tetramethyrhodamine (TMR) or Texas Red (TR) which fluoresce when either bound or unbound. Alternatively, labels may attenuate, for example, turning on or turn off, depending on their local environment. In some embodiments, labels may be off initially (non-fluorescent or quenched) and turned on in presence of chemical reagents or enzymes. In some embodiments fluorescent labels may be associated with quenchers at short distances which quench nearby fluorescence. At greater distances a quencher may have little to no quenching effect on a fluorophore. For example, some DNA or RNA aptamers described herein may have complementary regions with a fluorophore and quencher in close proximity to each other residing on opposing sections of DNA.

Figure 18:
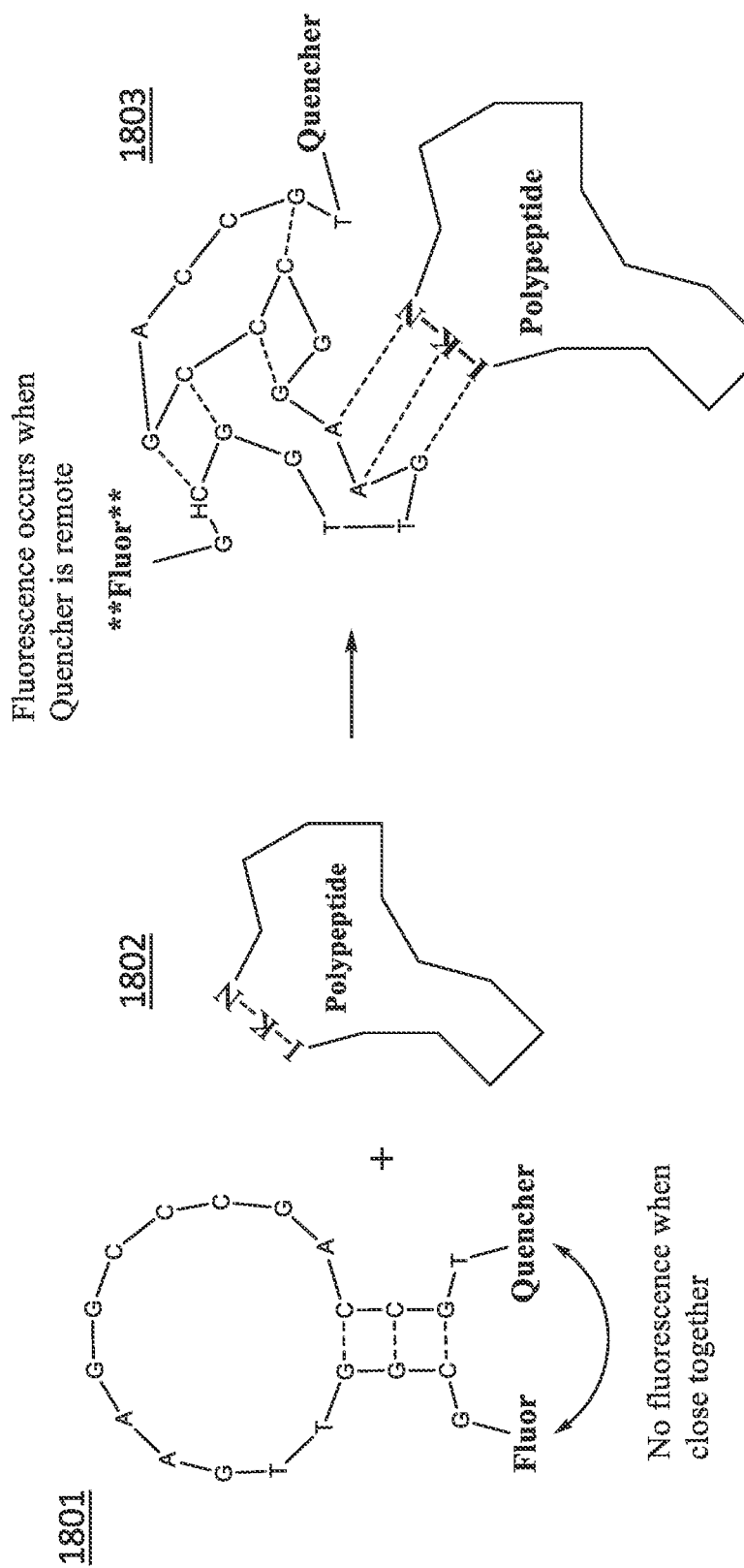
FIG. 18 shows a polypeptide binding to an aptamer and in the process, separating the aptamer's fluorescent and quencher group to allow fluorescence to occur.
Figure 19:
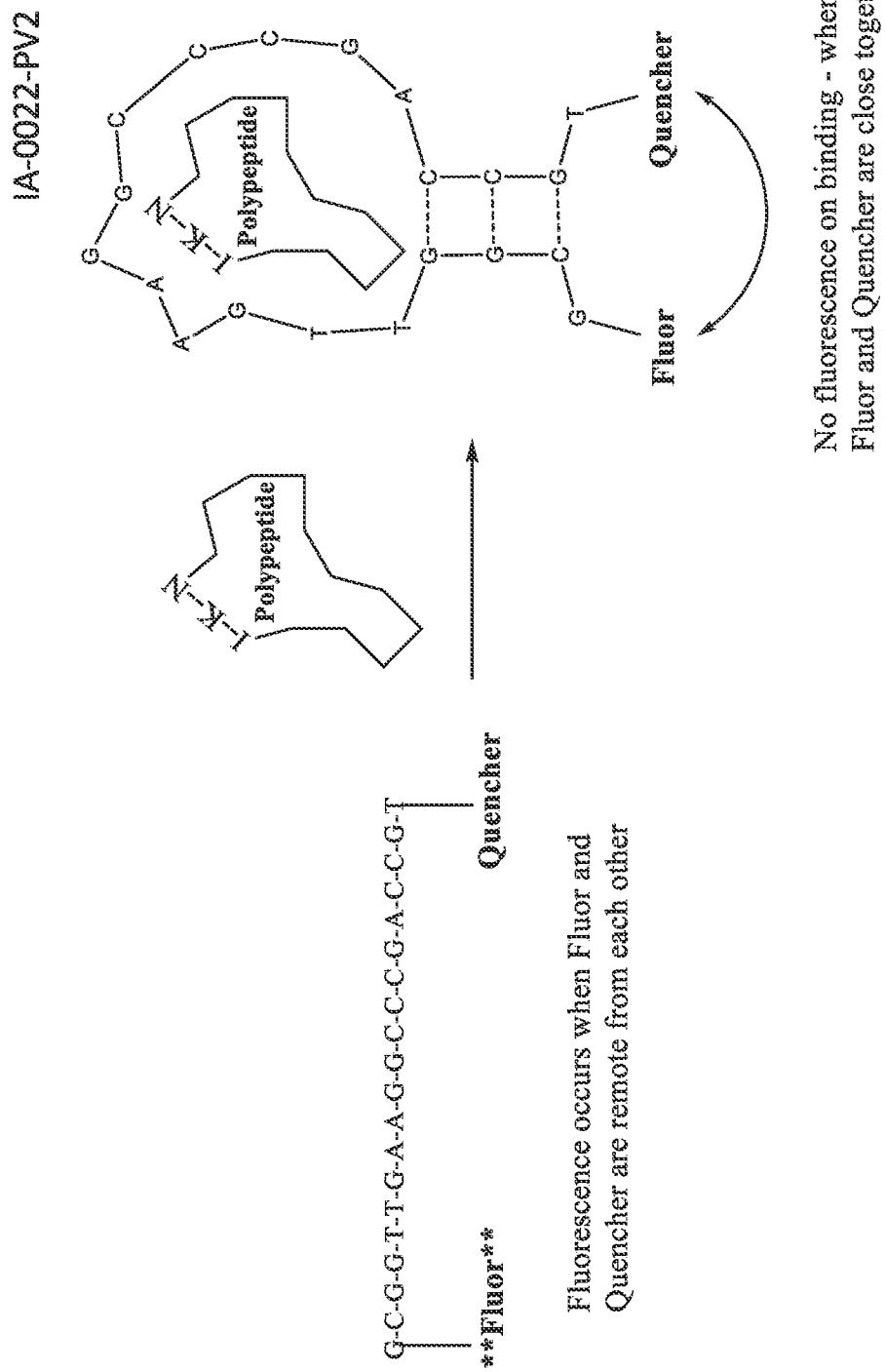
FIG. 19 shows a polypeptide binding to an aptamer and in the process, bringing the aptamer's fluorescent and quencher groups in close proximity to quench fluorescence on binding.

FIG. 18 shows a non-limiting example of such a system. The fluor and quencher are held in close proximity as shown in native aptamer 1801 (similar to molecular beacons) by complementary bases in their vicinity. An amino acid epitope trimer, for example, I-K-N in polypeptide 1802 may complex with an aptamer 1801 to afford complex 1803 where the fluor and quencher are separated to such an extent that the quencher no longer has a quenching effect on the fluorophore. In this case, epitopes may include polypeptide isoforms with one of more families of proteoforms containing PTMs within or in the vicinity of the epitopic trimer amino acid sequence. For example, serine, threonine or tyrosine including side-chain phosphate groups. FIG. 19 shows a similar case to FIG. 18 except in this case, a fluorescent signal is lost on affinity reagent binding due to the polypeptide bringing the fluorophore and quencher within a quenching distance of each other on binding.

Through-bond energy-transfer (TBET) cassettes such as those described by Burgess et al. (U.S. Pat. No. 7,402,677 B2 which is herein incorporated by reference in its entirety) are intramolecular FRET labels containing both donor and acceptor groups connected by a carbon-carbon triple bond. This allows fluorescent compounds to be made which have the same light absorbing donor moieties but have different light-emitting acceptor moieties.

Margulies et al. (U.S. Pat. No. 9,696,310 B2, incorporated by reference in its entirety) describes a series of thiazole orange asymmetrical benzothiazole-quinoline cyanine dyes including two aromatic groups separated by central rotatable linkers. While in free rotation, the cyanine dyes are not fluorescent as fluorescence activity requires both aromatic groups to be in conjugation or substantially coplanar. However, upon binding to, for example, a polypeptide, the two flanking aromatic groups may become conjugated and therefore fluorescent. Such dyes and biological conjugates may be incorporated into affinity reagents/aptamers described herein in order to distinguish between proteoforms of analyte polypeptides.

Detection of different affinity reagent binding to different proteoforms of polypeptides with field-effect transistors (FET) on various surfaces such as graphene or graphene oxide and in combination with silicon reagents such as (polydimethylsiloxane) PDMS may also be used to generate detection signals.

An evanescent field is a residual optical field that "leaks" during total internal reflection (TIR). This leaking of light fades off at an exponential rate. The evanescent field has found a number of applications in nanometer resolution imaging including single molecule detection in, for example, zero mode waveguides. Evanescent fields may be used for excitation of fluorescent reagents used as part of affinity reagents described herein. Detection methods may include, optical imaging, total internal reflection fluorescence (TIRF), super-resolution microscopy, structured-light microscopy, widefield microscopy, or confocal microscopy.

Computer Systems

Figure 15:
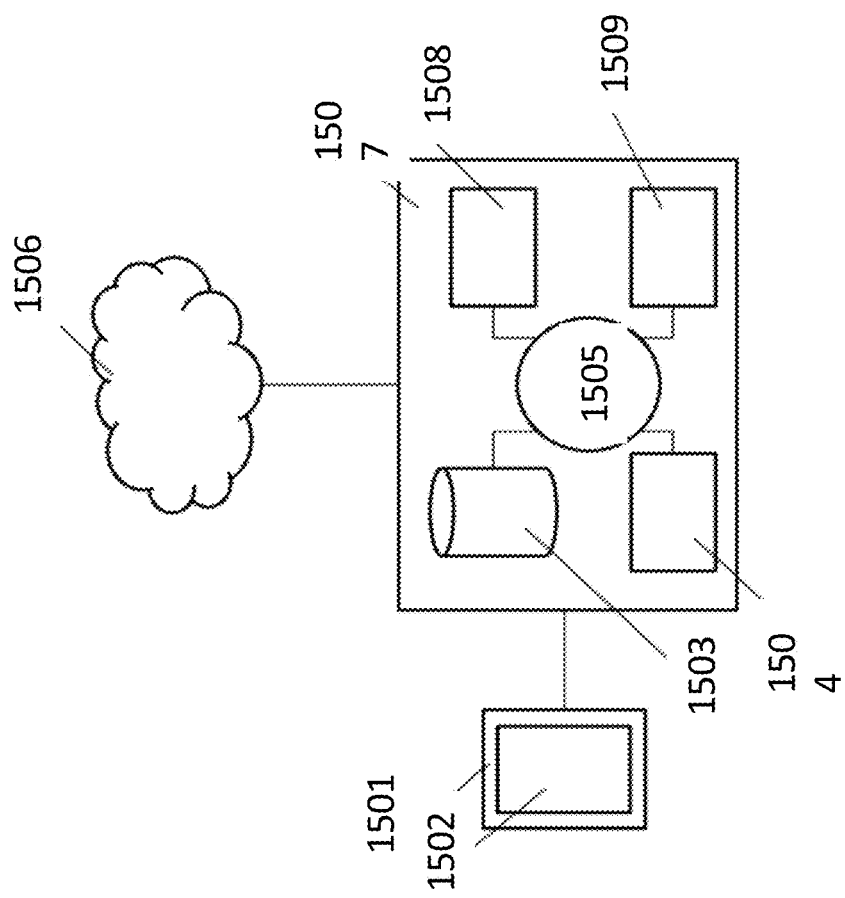
FIG. 15 illustrates a computer control system that is programmed or otherwise configured to implement methods provided herein.

The present disclosure provides computer systems that are programmed to implement methods of the disclosure. FIG. 15 shows a computer system 1507 that is programmed or otherwise configured to, for example, acquire pixel information of an array of biological, chemical, or physical entities; and detect the array of biological, chemical, or physical entities based at least in part on the acquired pixel information. The computer system 1507 can regulate various aspects of analysis, calculation, and generation of the present disclosure, such as, for example, acquiring video, image, or pixel information of an array of biological, chemical, or physical entities; and detecting components of the array of biological, chemical, or physical entities based at least in part on the acquired video, image, or pixel information. The computer system 1507 can be an electronic device of a user or a computer system that is remotely located with respect to the electronic device. The electronic device can be a mobile electronic device.

The computer system 1507 includes a central processing unit (CPU, also "processor" and "computer processor" herein) 1505, which can be a single core or multi core processor, or a plurality of processors for parallel processing. The computer system 1507 also includes memory or memory location 1504 (e.g., random-access memory, read-only memory, flash memory), electronic storage unit 1503 (e.g., hard disk), communication interface 1508 (e.g., network adapter) for communicating with one or more other systems, and peripheral devices 1509, such as cache, other memory, data storage and/or electronic display adapters. The memory 1504, storage unit 1503, interface 1508 and peripheral devices 1509 are in communication with the CPU 1505 through a communication bus (solid lines), such as a motherboard. The storage unit 1503 can be a data storage unit (or data repository) for storing data. The computer system 1507 can be operatively coupled to a computer network ("network") 1506 with the aid of the communication interface 1508. The network 1506 can be the Internet, an internet and/or extranet, or an intranet and/or extranet that is in communication with the Internet. The network 1506 in some embodiments, is a telecommunication and/or data network. The network 1506 can include one or more computer servers, which can enable distributed computing, such as cloud computing. For example, one or more computer servers may enable cloud computing over the network 1506 ("the cloud") to perform various aspects of analysis, calculation, and generation of the present disclosure, such as, for example, acquiring pixel information of an array of biological, chemical, or physical entities; and detecting components of the array of biological, chemical, or physical entities based at least in part on the acquired pixel information. Such cloud computing may be provided by cloud computing platforms such as, for example, Amazon Web Services (AWS), Microsoft Azure, Google Cloud Platform, and IBM cloud. The network 1506, in some embodiments, with the aid of the computer system 1507, can implement a peer-to-peer network, which may enable devices coupled to the computer system 1507 to behave as a client or a server.

The CPU 1505 can execute a sequence of machine-readable instructions, which can be embodied in a program or software. The instructions may be stored in a memory location, such as the memory 1505. The instructions can be directed to the CPU 1505, which can subsequently program or otherwise configure the CPU 1505 to implement methods of the present disclosure. Examples of operations performed by the CPU 1505 may include fetch, decode, execute, and writeback. The CPU 1505 can be part of a circuit, such as an integrated circuit. One or more other components of the system 1507 can be included in the circuit. In some embodiments, the circuit is an application specific integrated circuit (ASIC).

The storage unit 1503 can store files, such as drivers, libraries and saved programs. The storage unit 1503 can store user data, e.g., user preferences and user programs. The computer system 1507 in some embodiments, can include one or more additional data storage units that are external to the computer system 1507, such as located on a remote server that is in communication with the computer system 1507 through an intranet or the Internet.

The computer system 1507 can communicate with one or more remote computer systems through the network 1506. For instance, the computer system 1507 can communicate with a remote computer system of a user (e.g., a physician, a nurse, a caretaker, a patient, or a subject). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1507 via the network 1506.

Methods as described herein can be implemented by way of machine (e.g., computer processor) executable code stored on an electronic storage location of the computer system 1507, such as, for example, on the memory 1504 or electronic storage unit 1503. The machine-executable or machine-readable code can be provided in the form of software. During use, the code can be executed by the processor 1505. In some embodiments, the code can be retrieved from the storage unit 1503 and stored on the memory 1504 for ready access by the processor 1505. In some situations, the electronic storage unit 1503 can be precluded, and machine-executable instructions are stored on memory 1504.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1507, can be embodied in programming. Various aspects of the technology may be thought of as "products" or "articles of manufacture" typically in the form of machine (or processor) executable code and/or associated data that is carried on or embodied in a type of machine-readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

A machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that include a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer-readable media may be involved in carrying one or more sequences of one or more instructions to a processor for execution.

The computer system 1507 can include or be in communication with an electronic display 1501 that includes a user interface (UI) 1502 for providing, for example, video, image, or pixel information of an array of biological, chemical, or physical entities, and detected biological, chemical, or physical entities. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1505. The algorithm can, for example, acquire video, image, or pixel information of an array of biological, chemical, or physical entities; and detect the array of biological, chemical, or physical entities based at least in part on the acquired video, image, or pixel information.

Fluorescence Lifetime Methods

A fluorescence lifetime (FLT) is a time a certain fluorophore in a given environment spends in an excited state before emitting a photon and returning to its ground state under given conditions. FLT may vary, typically from low picoseconds to thousands of nanoseconds depending on the type of fluorophore. Phosphorescent dyes and other luminophores can have longer lifetimes. It will be understood that methods and compositions exemplified herein with regard to FLT can be extended to other luminophores and longer luminescence lifetimes. FLT is an intrinsic property of a fluorophore and does not depend on the fluorophore's concentration, absorption by a sample, sample thickness, method of measurement, fluorescence intensity, and/or excitation intensity. It is affected by external factors, such as temperature, polarity, and the presence of fluorescent quenchers. Any change in the physicochemical environment of a fluorophore may lead to changes in its fluorescence lifetime. Lifetime-based binding assays can be developed including binding assay wherein two components bind to each other. For example, sets of affinity reagents described herein labeled with different fluorescent labels with detectably different fluorescence lifetimes may bind to and characterize different proteoforms of polypeptides.

Figure 16:
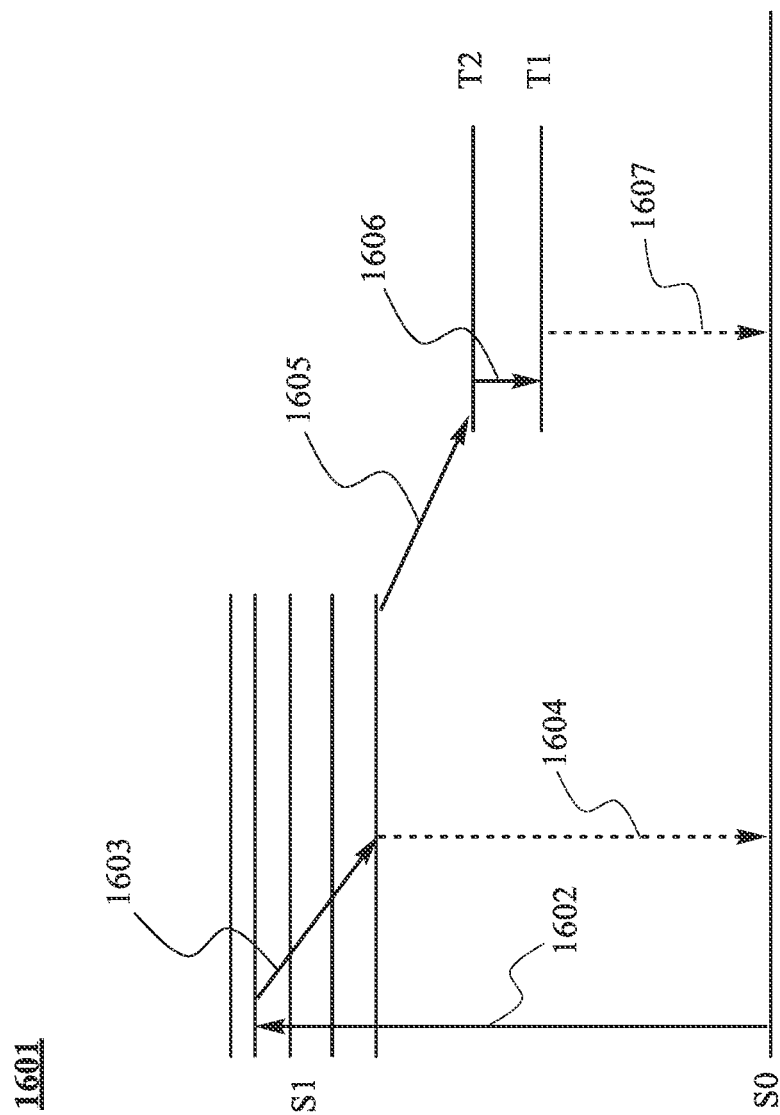
FIG. 16 shows a Jablonski diagram for a fluorescence lifetime process where an excited state may relax back to its ground state by a fluorescence or phosphorescence radiative process. (It may also relax to its ground state via a non-radiative process, for example, by collisional energy transfer).

Fluorescent and phosphorescent dyes have an exponential fluorescent decay transient after the removal of their excitation source, which defines their characteristic lifetime. As light-yielding emission is an average measurement of random emissions, an associated lifetime of a fluorophore is the average time the molecules in a sample spend in their excited state before photon emission occurs. FIG. 16 illustrates a Jablonski diagram for this process 1601. An electronic transition 1602 occurs promoting a ground state S0 electron to a higher electronic state S1. After descending one or more smaller vibrational levels in S1, the electron may drop down to its ground state S0 with concurrent photon emission yielding a fluorescent event 1604. Alternatively, it may cross over from a singlet state to a longer-lived triplet state T2 where it can drop down to T1 and from there afford a phosphorescent event 1607 back to its ground state S0.

FLT may be sensitive to internal factors dependent on fluorophore structure. Methods described herein may use fluorescent lifetime detection methods, for example, as part of one or more affinity reagents, including antibodies, DNA or RNA aptamers, affibodies and as part of macro DNA or RNA scaffold structures. FLT can be measured in either the frequency domain or the time domain. The time domain method includes the illumination of a sample array with short pulses of light, followed by measuring emission intensities against time. The FLT may be determined from the slope of emission decay curves. Several fluorescence detection methods are available for lifetime measurements, for example, time-correlated single photon counting (TCSPC) enables simple data collection and enhanced quantitative photon counting.

The frequency domain method for measuring FLT involves the sinusoidal modulation of incident light at high frequencies. Emission occurs at the same frequency as the incident light accompanied with a phase delay and/or a change in the amplitude relative to excitation light (demodulation). FLT measurements have several advantages over intensity-based measurements. For example, lifetime measurements may not require wavelength-ratiometric labels to provide quantitative determination of an array of proteoforms of polypeptides. Fluorescence lifetime methods may expand sensitivities of analyte concentration ranges (assay dynamic range) by using labels with spectral shifts.

Temporal methods may be used in assays based on fluorescence lifetime measurements. A light source may be pulsed to produce excitation pulses such that excitation light is temporally separated from fluorescence emission signal. Pulsed excitation light may be further separated from fluorescence signals by using spectral filters (e.g., polarization filters, etc.). More recently, arrays of photon counters have been proposed in order to provide parallelized detection of multiple targets. The arrays of photon counters may be formed on a silicon substrate using complementary metal oxide semiconductor (CMOS) technologies where each pixel element may include a single photon avalanche diode (SPAD).

Finkelstein describes fluorescence lifetime based techniques in sequencing biomolecules by synthesis arrays. See the following, which are expressly incorporated by reference for all purposes: Finkelstein et al., Method and System for Fluorescence Lifetime Based Sequencing, U.S. Pat. No. 10,895,534 B2. Joseph R. Lakowicz. Topics in Fluorescence Spectroscopy: Volume 4: Probe Design and Chemical Sensing. Vol. 4. Springer Science & Business Media, 1994. Hutchinson, Christina L., J. R. Lakowicz, and Eva M. Sevick-Muraca. "Fluorescence lifetime-based sensing in tissues: a computational study. "Biophysical Journal 68.4 (1995): 1574; and, "High Performance Silicon Imaging, 2020 Elsevier Ltd., Chapter 12, Henderson, et al., "CMOS Sensors for Fluorescence Lifetime Imaging".

The Molecular Probes Handbook—A Guide to Fluorescent Probes and Labeling Technologies (Thermo Fisher Scientific and Richard P. Haugland, 11th Edition) describes fluorescent labels, labelling methods and references for a wide range of commercially available detection reagents and is hereby expressly incorporated by reference. Fluorescent labels also include, but are not limited to, green fluorescent protein (GFP; Chalfie, et al., Science 263(5148):802-805 (Feb. 11, 1994); and EGFP; Clontech-Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12):5408-5417 (1993)), .beta.-galactosidase (Nolan, et al., Proc Natl Acad Sci USA 85(8):2603-2607 (April 1988)) and Renilla WO 92/15673; WO 95/07463; WO 98/14605; WO 98/26277; WO 99/49019; U.S. Pat. Nos. 5,292,658; 5,418,155; 5,683,888; 5,741,668; 5,777,079; 5,804,387; 5,874,304; 5,876,995; and 5,925,558). All of the above-cited references are expressly incorporated herein by reference.

In some embodiments, an excitation energy may be a pulse of light from a light source. In some embodiments, an excitation energy may be in the visible spectrum. In some embodiments, an excitation energy may be in the ultraviolet spectrum. In some embodiments, an excitation energy may be in the infrared spectrum. In some embodiments, an excitation energy may be at or near the absorption maximum of a luminescent label from which a plurality of emitted photons are to be detected. In some embodiments, the excitation energy may be between about 450 nm and about 750 nm (e.g., between about 450 nm and about 600 nm, between about 600 nm and about 750 nm, between about 500 nm and about 550 nm, between about 550 nm and about 600 nm, between about 600 nm and about 650 nm, or between about 650 nm and about 750 nm). In certain embodiments, an excitation energy may be monochromatic or confined to a spectral range. In some embodiments, a spectral range may have a range of between about 0.1 nm and about 1 nm, between about 1 nm and about 2 nm, or between about 2 nm and about 5 nm. In some embodiments, a spectral range has a range of between about 5 nm and about 10 nm, between about 10 nm and about 50 nm, or between about 50 nm and about 100 nm.

Two Photon Excitation Methods

Two-photon excitation microscopy (TPEF or 2PEF) is a complementary fluorescence excitation/detection technique compared to single photon excitation. In traditional fluorescence microscopy, excitation wavelengths are generally shorter than corresponding emission wavelengths. A photon of $\lambda 1$ may be absorbed by a fluorescent species resulting an electronic transition from a lower electronic level, S0 to a higher electronic level, S1. Typically, after a brief time (picoseconds to milliseconds depending on the type of fluorophore) the photon may be emitted with a wavelength of $\lambda 2$, where $\lambda 1$ is shorter than $\lambda 2$ mainly due to a certain amount of vibrational energy loss during the process. In two-photon excitation, simultaneous excitation of a fluorophore by two photons can use an excitation source having longer excitation wavelengths of light than corresponding emission wavelengths.

Two-photon excitation detection has several advantages over single photon methods. It can penetrate deeper into analyte samples (around 1 mm) due to its long wavelength of operation. As it relies on longer excitation wavelengths of light, it is also less photo-damaging to molecular species. Commonly used wavelengths for two-photon excitation (typically 720 to 1000 nm) lie in the red or near-infrared region of the spectrum where absorption and scattering from a fluorescent label is decreased compared with shorter wavelengths. In contrast, confocal microscopy for example, uses shorter excitation wavelengths (345 to 655 nm) that may damage or photochemically alter analyte or reagent molecules.

Figure 17:
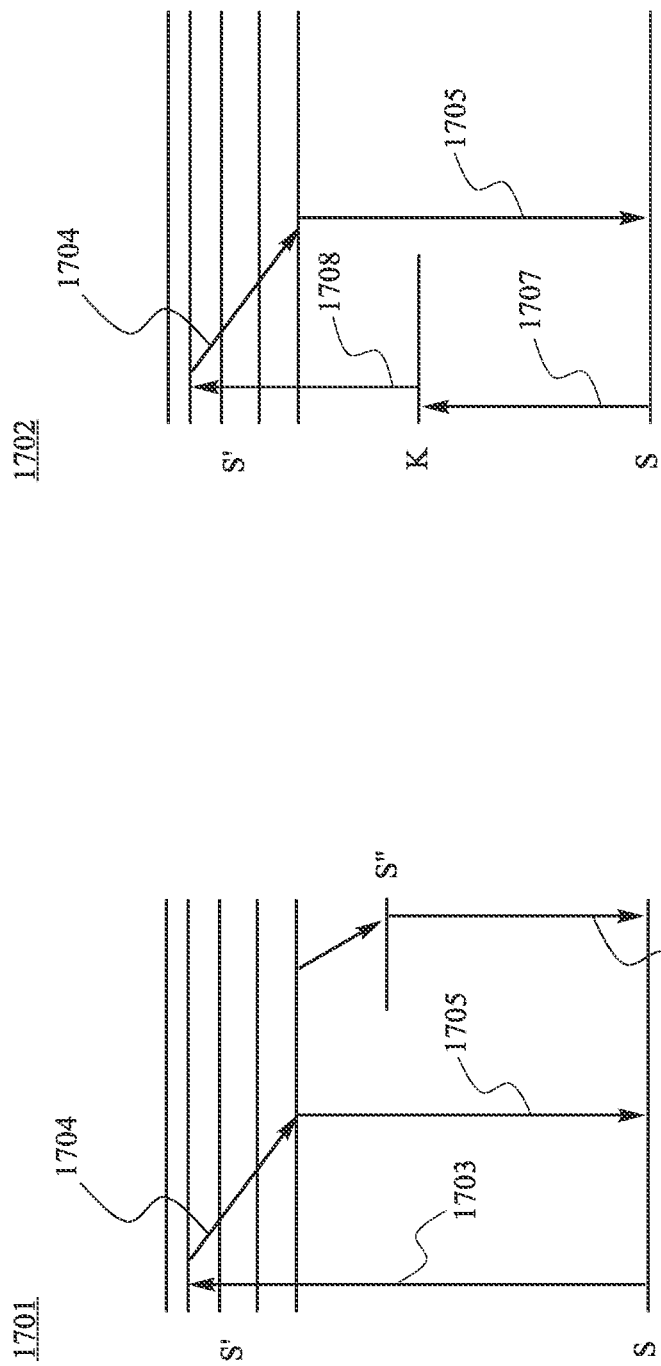
FIG. 17 illustrates comparative Jablonski diagrams for a one photon excitation process and for a two photon excitation process.

FIG. 17 shows Jablonski diagrams for one photon 1701 versus two photon 1702 excitation. In 1701, arrow 1703 represents a ground state (S) electron being promoted to a higher electronic absorbing energy in the form of electromagnetic radiation (hn1, where h is Planck's Constant and where n1 is the frequency of absorbed light) and being promoted to a fourth vibrational level of an electronic excited state (S'). The electron may then drop down one or more vibrational levels (see arrow 1704) and may return to its ground state (S) emitting light with energy hn2 where hn1>hn2. Arrow 1706 represents the electron returning back to the ground state via a non-radiative pathway (S"). Diagram 1702 shows two photon absorption where an electron is promoted to a higher electronic level by two distinct absorption events.

The first absorption event 1707 places the electron in an intermediate energy level, K. Almost simultaneously, a second absorption event 1708 equal in energy to 1707, promotes the electron into the first excited electron state, S'.

The most common type of lasers used in two-photon microscopy are femtosecond-pulsed lasers that deliver short pulses of very high intensity light. A pulsed laser delivers less total energy to the sample which makes it less damaging to the tissues. Two-photon excitation is generally possible only in a small focal volume in the sample and therefore very little out-of-focus fluorescence is generated with most of the detected light emanating from a single point. Methods described herein may use two-photon excitation methods on an array of samples as part of a detection system for detectable labels. Methods described herein may use two-photon excitation methods, for example, where affinity reagents include two photon excitation reporter groups. Detecting signals in two-photon excitation systems may include detecting emission signals resulting from two-photon excitation of a reporting affinity reagent fluorophore. See the following, which are expressly incorporated by reference for all purposes: "Two Photon Uncaging of Glutamate" Ellis-Davies, Frontiers in Synaptic Neuroscience, January 2019, Vol 10, Article 48, Pp. 1-13; and, "Large Field of View, High Resolution Microscope", Svoboda et al., U.S. Pat. No. 10,901,194 B2.

Fluorescence Polarization

The technique of fluorescence polarization (FP) is based on the observation that a fluorescently labeled molecule excited by plane polarized light, emits light with varying degrees of plane polarization from polarized to depolarized that are inversely proportional to its rate of molecular rotation. This property of fluorescence can be used to measure the interaction of a relatively small, labeled ligand with a larger receptor. A protein when used in a method set forth herein can be treated as a ligand or receptor depending upon the configuration of the method. FP can provide a basis for direct or competition binding assays without separation steps. FP or anisotropy measurements (often measured in milli-P units or mP) can provide information on molecular orientation and mobility and processes that affect mobility, for example, receptor—ligand interactions, protein-affinity reagent interactions, protein-SNAP interactions, or protein—DNA interactions.

FP tracers may include a relatively small fluorescent dye coupled with an analyte set forth herein, such as a protein or SNAP. In FP, incident excitation plane polarized light may be depolarized when emitted from the tracer when the time it takes for a fluorescent molecule to rotate or to have significant translational movement is relatively faster than its fluorescent lifetime (about 5 nS for fluorescein). If a FP tracer binds to a large slow-moving molecule, for example, a protein or SNAP, then the tracer-molecule complex as a whole may have a slower molecular rotation time than the dye's fluorescent lifetime and therefore emitted light emerging from the dye essentially remains in a detectable polarized form. Polarization-based readouts from single well, well-plate or other polarimeters may be less susceptible to environmental interferences than assays based on fluorescence intensity measurements alone. Experimentally, the degree of polarization can be determined from measurements of fluorescence intensities parallel and perpendicular with respect to the plane of linearly polarized excitation light. Depolarization due to flexibility in a linker attachment of dyes to tracers, for example, using long alkyl or PEG chains, sometimes referred to as the propeller effect, may clearly reduce fluorescent label sensitivity due to large degrees of freedom and therefore short or rigid linkers are often used to link dyes to FP tracers.

Fluorescent components of tracers which may be used with methods described herein include but are not limited to; fluorescein, Alexa dyes, bodipy, pyrene, rhodamines, cyanine dyes and many more commonly used small molecule fluorophores. FP may be used in methods described herein to detect complex formation between fluorescently labeled aptamers and addressable proteoforms of polypeptides on an array. It may also be used with antibody affinity reagents where a fluorophore of interest may reside either on the antibody or on the polypeptide analyte.

FP has a number of key advantages. It may be carried out entirely in solution phase or by using an array of analytes. It does not require any separation of bound and free ligand or protein, and is readily adaptable to low volumes. In some cases, a free fluorescent aptamer tracer may bind to a proteoform which may be measured, for example, in a well-plate polarimeter. A competitive binding step may then be performed using an excess of a non-labeled aptamer resulting in a depolarized state with a corresponding decrease in mP measurement values.

EXAMPLES

Example 1: Quantitation of EGFR Proteoforms

A sample including EGFR proteins is quantified to determine the relative abundances of EGFR proteoforms. The sample includes a mixture of EGFR proteins of a first proteoform and a second proteoform (hereinafter referred to as EGFR-1 and EGFR-2, respectively). The mixture of polypeptides from an EGFR-containing sample are quantified utilizing an affinity reagent binding assay.

A sample including EGFR proteins is prepared by functionalizing the sample polypeptides with a methyl tetrazine (mTz) moiety. Functionalized polypeptides are prepared by reacting amine-containing sidechains of polypeptides with heterobifunctional NHS-PEG-mTz molecules. After mTz functionalization and purification to remove excess reactants, the mTz-functionalized sample polypeptides are conjugated to DNA origami tiles including a single polypeptide attachment site. An exemplary schematic of a DNA origami tile is shown in FIG. 1. Each DNA origami tile polypeptide attachment site contains a trans-cyclooctene (TCO) moiety. mTz-functionalized polypeptides are combined with DNA origami tiles to form a plurality of polypeptide composites by a click reaction of a mTz moiety with a TCO moiety, where each polypeptide composite includes a polypeptide and a DNA origami anchoring group.

The plurality of polypeptide composites are deposited on a solid support including a patterned array of polypeptide composite binding sites. Each polypeptide composite binding site constitutes a distinct, observable address. The solid support is displayed on a surface of a microfluidic device that is configured for fluorescent imaging. The polypeptide composite binding sites are configured to each bind only a single polypeptide composite. The plurality of polypeptide composites is deposited on the solid support array in the presence of a surfactant. Following the polypeptide composite deposition, the solid support includes an array of polypeptides containing EGFR proteins coupled to the solid support by a DNA origami tile anchoring group.

The array of polypeptides is contacted with multiple cycles of affinity reagents. Each cycle of affinity reagents involves: i) contacting a fluorescently-labeled affinity reagent pool with the array of polypeptides on the solid support; ii) permitting affinity reagents of the affinity reagent pool to bind with polypeptides of the array of polypeptides; iii) removing unbound affinity reagents with a rinse buffer; iv) detecting the presence or absence of a fluorescent signal at each observable address on the solid support; v) removing bound affinity reagents from the polypeptides with a stripping buffer; and vi) optionally detecting the presence or absence of a fluorescent signal at each observable address on the solid support after removal of the affinity reagent.

The array of polypeptides containing EGFR proteins is contacted with two cycles of affinity reagents. The first cycle utilizes an anti-pan-EGFR antibody (i.e., an antibody that binds to both EGFR-1 and EGFR-2). The second cycle utilizes an anti-EGFR-2 antibody (i.e., an antibody that binds EGFR-2 but not EGFR-1). The anti-pan-EGFR and anti-EGFR-2 antibodies are each labeled with Alexa FluorÒ 647 fluorescent dye. Distinct binding profiles are expected for addresses containing EGFR-1 or EGFR-2. Table I shows expected binding profiles for both EGFR proteoforms, where a check mark indicates an optical observation of binding.

TABLE I

EGFR Proteoform Binding Profiles

| | Anti-pan-EGFR | Removal | Anti-EGFR-2 |
|---|---|---|---|
| EGFR-1 | ☑ | | ☑ |
| EGFR-2 | ☑ | ☑ | |

Binding cycles are performed for the anti-pan-EGFR and anti-EGFR-2 antibodies. Fluorescence imaging is performed utilizing a confocal fluorescent microscopy system that senses emission at 647 nm. Optionally, one or more binding cycles of one or both antibodies are performed to increase confidence in the detection data. Imaging data containing address-specific binding detections are transferred to a decoding algorithm. The decoding algorithm determines on an address-by-address basis the confidence of an observed binding event or lack of a binding event. Based upon the binding profile detailed in Table I, each address on the solid support is characterized as containing EGFR-1, containing EGFR-2, containing neither proteoform, containing no polypeptide, or containing an unknown or uncertain polypeptide.

Figure 2B:
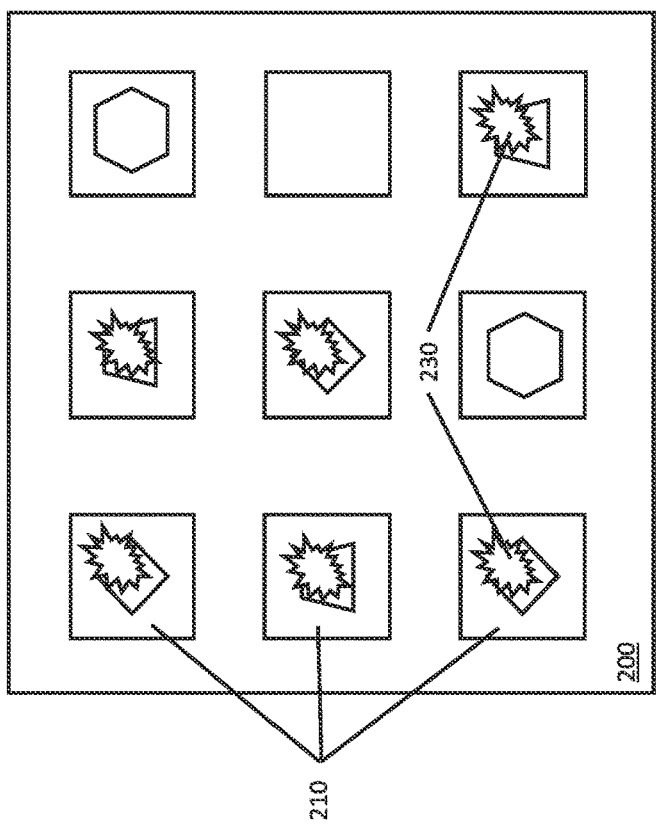
FIG. 2B depicts observed binding events for a first affinity reagent in contact with a polypeptide array, in accordance with some embodiments.
Figure 2A:
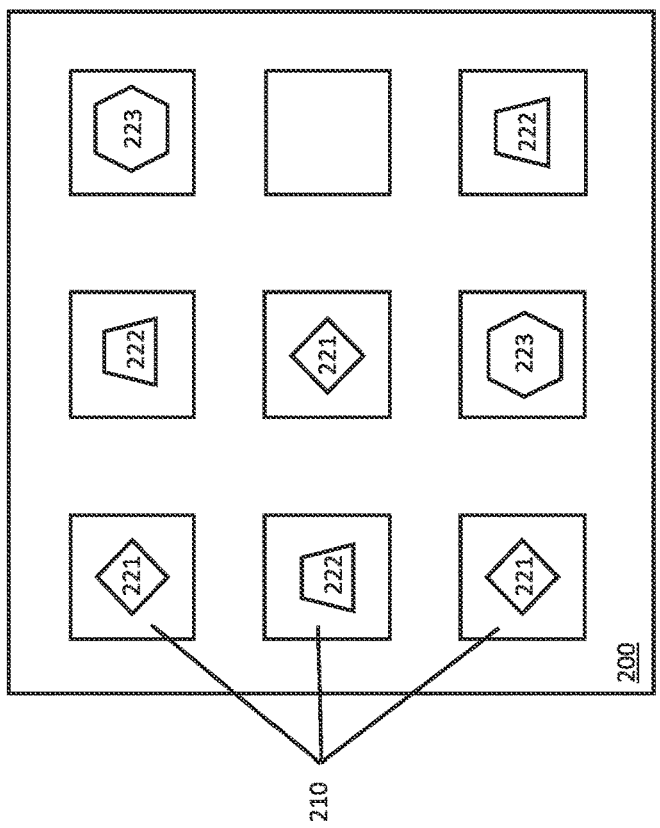
FIG. 2A depicts a polypeptide array including multiple proteoforms of a polypeptide species, in accordance with some embodiments.
Figure 2D:
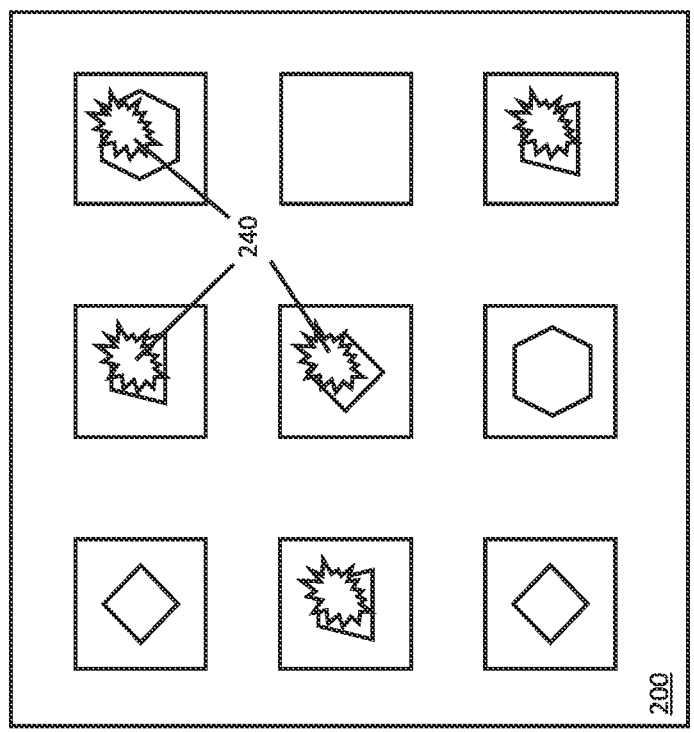
FIG. 2D depicts observed binding events for a second affinity reagent in contact with a polypeptide array, in accordance with some embodiments.
Figure 2C:
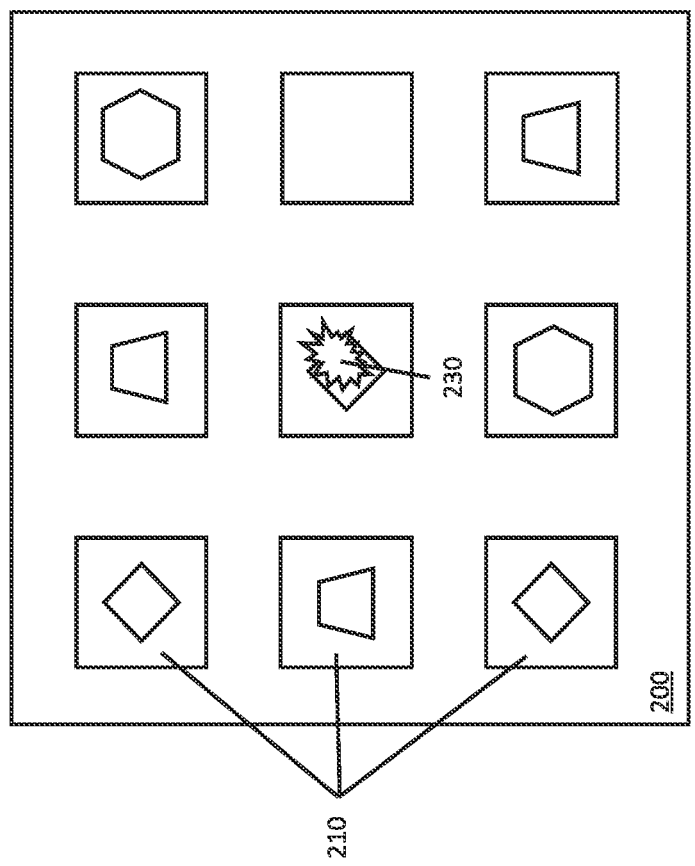
FIG. 2C observed binding events after the removal of a first affinity reagent from a polypeptide array, in accordance with some embodiments.
Figure 2E:
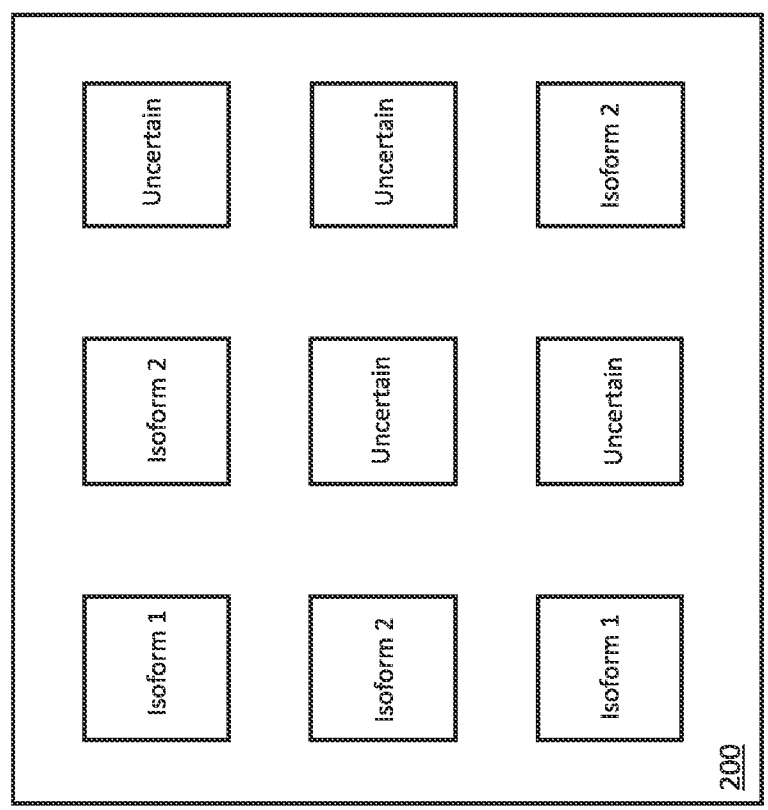
FIG. 2E depicts inferred polypeptide identities for each observable address of a polypeptide array, in accordance with some embodiments.

FIGS. 2A-2E depict exemplary binding observations and data interpretation for an array of polypeptides. As shown in FIG. 2A, polypeptides are bound to a solid support 200 at an ordered array of polypeptide binding sites 210. The plurality of polypeptides includes EGFR proteoform 1 (221) and proteoform 2 (222), as well as non-EGFR polypeptides 223. As shown in FIG. 2B, a plurality of anti-pan-EGFR affinity reagents 230 is contacted with the solid support 200, thereby permitting binding of the affinity reagent to available target polypeptides. Six binding events are observed to occur. As shown in FIG. 2C, after removal of any bound affinity reagents, the array is again detected to observe any residual binding events. One affinity reagent 230 is observed to remain on the array. As shown in FIG. 2D, a plurality of anti-EGFR-2 affinity reagents 240 is contacted with the solid support 200, thereby permitting binding of the affinity reagent to available target polypeptides. Five binding events are observed to occur, although the binding event at the center binding site is likely to be removed due to the persistent signal from the first binding cycle. FIG. 2E depicts predictions based upon the observed binding profiles at each observed address on the array. Four addresses are labeled uncertain due to a lack of observed binding in either cycle or a binding profile that does not conform to either EGFR proteoform. Usage of additional affinity reagents or additional cycles of the two anti-EGFR antibodies could increase the confidence of the prediction to permit identification of each address.

Example 2. Quantitation of EGFR Proteoforms

The method of Example 1 is performed on a mixture containing EGFR proteins. In place of DNA origami tiles with a single polypeptide attachment site, DNA origami tiles including 6 polypeptide attachment sites (all TCO) are utilized. The 6-TCO DNA origami tiles are conjugated to the polypeptide sample per the method of Example 1, thereby generating a plurality of polypeptide composites including 0 to 6 conjugated polypeptides.

The mixture of polypeptide composites are deposited on a solid support per the method of Example 1, thereby creating an array of polypeptides on the solid support. Each address of the solid support may include 0 to 6 polypeptides coupled to the address by the DNA origami tile anchoring group. Each address may contain only EGFR-1, only EGFR-2, a mixture of co-localized EGFR-1 and EGFR-2, or neither proteoform.

The array is cycled with anti-pan-EGFR antibodies and anti-EGFR-2 antibodies as described in Example 1. Optionally, one or more binding cycles of one or both antibodies are performed to increase confidence in the detection data. After imaging of affinity reagent binding for each cycle, the data is transferred to a decoding algorithm. The decoding algorithm determines on an address-by-address basis the confidence of an observed binding event or lack of a binding event. Based upon the binding profile detailed in Table I, each address on the solid support is characterized as containing EGFR-1, containing EGFR-2, containing both EGFR-1 and EGFR-2, containing neither proteoform, containing no polypeptide, or containing an unknown or uncertain polypeptide.

Example 3. Quantitation of EGFR Proteoforms

The methods of Examples 1 and 2 may be extended to quantifying larger numbers of proteoforms. The method of Example 1 or 2 is performed on a mixture including EGFR-1, EGFR-2, and EGFR-3. 3 cycles of affinity reagent binding is utilized to determine polypeptide identity utilizing anti-pan-EGFR antibodies (i.e., able to bind to all EGFR proteoforms), anti-EGFR-1 antibodies, and anti-EGFR-2 antibodies. Table II lists expected binding profiles for each EGFR proteoform.

The array is cycled with anti-pan-EGFR antibodies, anti-EGFR-1 antibodies, and anti-EGFR-2 antibodies as described in Examples 1 or 2. Optionally, one or more binding cycles of one or all antibodies are performed to increase confidence in the detection data. After imaging of affinity reagent binding for each cycle, the data is transferred to a decoding algorithm. The decoding algorithm determines on an address-by-address basis the confidence of an observed binding event or lack of a binding event. Based upon the binding profile detailed in Table II, each address on the solid support is characterized as containing EGFR-1, containing EGFR-2, containing EGFR-3, containing two or more of EGFR-1, EGFR-2, and EGFR-3, containing none of the proteoforms, containing no polypeptide, or containing an unknown or uncertain polypeptide.

TABLE II

EGFR Proteoform Binding Profiles

| | Anti-pan-EGFR | Removal | Anti-EGFR-1 | Removal | Anti-EGFR-2 |
|---|---|---|---|---|---|
| EGFR-1 | ☑ | | ☑ | | |
| EGFR-2 | ☑ | | | | ☑ |
| EGFR-3 | ☑ | | | | |

Example 4. Multiplex Detection of Proteoforms

The methods of Example 1 or 2 may be adapted to perform multiplex detection of proteoforms, thereby possibly reducing the total number of detection cycles utilized. An array of polypeptides is formed according to the method of Example 1 or 2. The array is contacted with a pool of a mixture of anti-pan-EGFR antibodies and anti-EGFR-2 antibodies. The anti-pan-EGFR antibodies are labeled with Alexa FluorÒ 488 fluorescent dyes and the anti-EGFR-2 antibodies are labeled with Alexa FluorÒ 647 fluorescent dyes.

Detection and decoding is performed according to the method of Example 1 or 2, with the addition of imaging at each address at 488 nm emission wavelength. Table III shows a characteristic binding profiles for both proteoforms. The decoding algorithm determines on an address-by-address basis the confidence of an observed binding event or lack of a binding event. Based upon the binding profile detailed in Table III, each address on the solid support is characterized as containing EGFR-1, containing EGFR-2, containing neither proteoform, containing no polypeptide, or containing an unknown or uncertain polypeptide.

TABLE III

| EGFR Proteoform Multiplex Binding Profiles | | |
| --- | --- | --- |
|  | 488 nm | 647 nm |
| EGFR-1 | ☑ |  |
| EGFR-2 | ☑ | ☑ |

Example 5. Proteoform Binding Data

Binding of affinity reagents to samples including differing polypeptide proteoforms was conducted according to the method described in Example 2. The measured polypeptide species included two proteoforms, proteoform 1 and proteoform 2, respectively. Binding was measured against 3 different samples: proteoform 1 only, proteoform 2 only, and a 50:50 mixture on a molar basis of both proteoforms. Binding was measured for a pan-antibody (binds to both proteoforms) and a proteoform 2-specific antibody. Results were replicated across multiple solid supports.

Figures 3A, 3B:
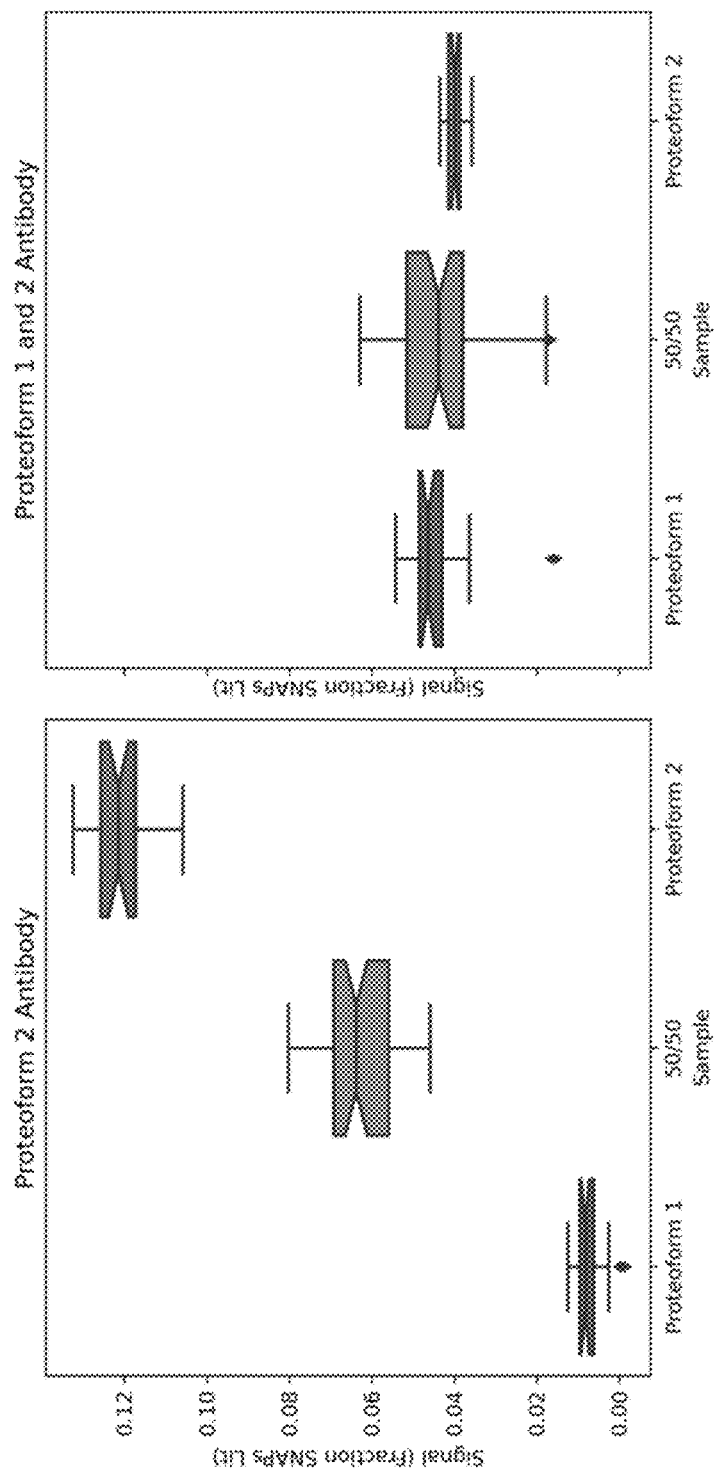
FIG. 3A displays binding measurements for a more specific affinity reagent against single-molecule arrays including two different proteoforms of a polypeptide species.
FIG. 3B displays binding measurements for a less specific affinity reagent against single-molecule arrays including two different proteoforms of a polypeptide species.
Figure 4:
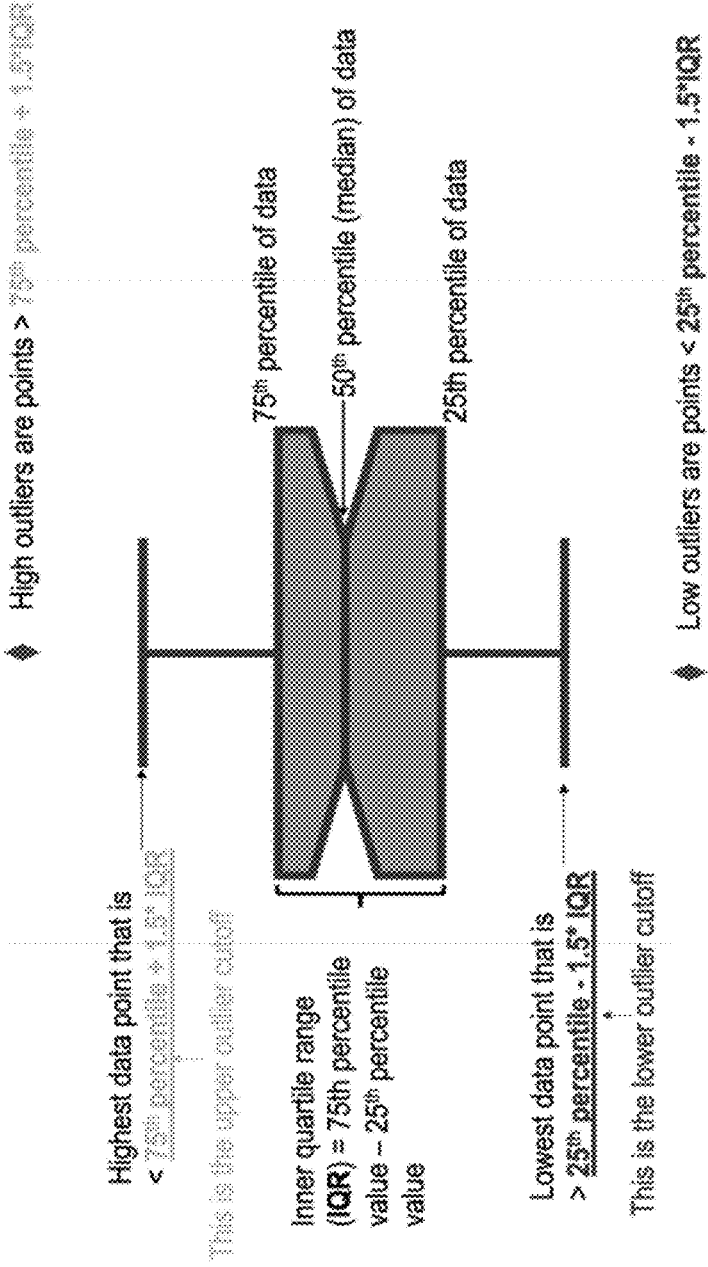
FIG. 4 illustrates the statistical display of information as depicted in FIGS. 3A and 3B.

FIG. 3A shows measured binding for the proteoform 2-specific antibody. A very low level of binding was seen against arrays including only proteoform 1 polypeptides. Binding against addresses on the proteoform 2 array was much more common. The 50:50 arrays had a level of binding that was about half of the binding seen in the proteoform 2 array, as would be expected. FIG. 3B shows measured binding for the pan-antibody. Each array was observed to have observed binding at a near equal number of polypeptide addresses, as would be expected for the less-specific affinity reagent. The pan-antibody and proteoform 2-specific antibody may be used together to identify and distinguish array addresses containing proteoform 1 or proteoform 2 of the polypeptide species. FIG. 4 describes the statistical representation of the data presented in FIGS. 3A and 3B.

Example 6. Proteome-Scale Proteoform Profiling

Tissue samples are collected from a population of organisms that have been diagnosed with the same inflammatory disorder. In parallel, tissue samples are collected from a population of the same organism that have not been diagnosed with the inflammatory disorder. A full proteome polypeptide sample is derived from each tissue sample for each collected samples. Each polypeptide sample is deposited on a unique array. The arrays are prepared according to the method described in Example 1 or 2.

After an array of polypeptides is prepared for each sample, each sample undergoes 300 cycles of affinity reagent binding measurements, as described in Examples 1 or 2. The 300 cycles of affinity reagent binding measurements includes 280 rounds utilizing affinity reagents with characterized binding affinities for trimer epitope sequences. The remaining 20 rounds of affinity reagent binding measurements utilize phosphorylation-specific and methylation-specific antibodies. Binding data is collected for all 300 affinity reagents for each sample. Data from each sample is transferred to a decoding algorithm. The decoding algorithm determines on an address-by-address basis the confidence of an observed binding event or lack of a binding event. The decoding algorithm provides an inferred identity for the observed polypeptides at each address on each solid support. The decoding algorithm further provides an inferred phosphorylation and/or methylation proteoform for all observed polypeptides.

After decoding for each sample, population for the diseased and healthy populations are pooled. Population-wide abundances and variances of phosphorylated and/or methylated proteoforms are determined for the diseased and healthy populations. The abundances and variances of phosphorylated and/or methylated proteoforms are then compared between the diseased and healthy populations to determine one or more biomarkers for diagnosis of the inflammatory disorder or one or more upstream or downstream proteoforms that correlate to the mechanism of the disease state.

Example 7: Methods, Systems and Compositions for Characterizing Proteoforms

The clauses below set forth various embodiments of the methods, systems and compositions of the present disclosure including, for example:

1. A method, comprising: a) providing an array of polypeptides, wherein the array of polypeptides comprises a first proteoform of a polypeptide and a second proteoform of the polypeptide, and wherein each polypeptide of the array of polypeptides is present at an individually observable address of the array; b) contacting the array of polypeptides with a first affinity reagent, wherein the first affinity reagent has a first characterized binding affinity, wherein the first affinity reagent comprises a first detectable label that is configured to transmit a first detectable signal; c) detecting presence or absence of the first detectable signal at each observable address on the array of polypeptides; d) contacting the array of polypeptides with a second affinity reagent, wherein the second affinity reagent has a second characterized binding affinity, wherein the second affinity reagent comprises a second detectable label that is configured to transmit a second detectable signal; e) detecting a presence or absence of the second detectable signal at each observable address on the array; and f) characterizing the presence or absence of the first proteoform and the second proteoform at each address of the array based upon the first characterized binding affinity of the first affinity reagent and the second characterized binding affinity of the second affinity reagent.

2. The method of clause 1, wherein each address of the array comprises a single coupled polypeptide.

3. The method of clause 1, wherein each address of the array comprises more than one coupled polypeptide.

4. The method of any one of the preceding clauses, wherein the first proteoform or the second proteoform is a post-translational modification proteoform of the polypeptide.

5. The method of clause 4, wherein the post-translational modification is selected from groups consisting of glycosylation, methylation, phosphorylation, acetylation, ubiquitination, formylation, pyroglutamyl, alkylation, acylation, and nitrosylation.

6. The method of any one of the preceding clauses, wherein the first proteoform or the second proteoform is a splicing isoform of the polypeptide.

7. The method of any one of the preceding clauses, wherein the first characterized binding affinity comprises a higher probability of binding to the first proteoform compared to the probability of binding to the second proteoform.

8. The method of clause 6, wherein the first characterized binding affinity comprises a higher probability of binding to the first proteoform compared to the probability of binding to the second proteoform.

9. The method of any one of the preceding clauses, wherein the second characterized binding affinity comprises a lower probability of binding to the first proteoform compared to the probability of binding to the second proteoform.

10. The method of clause 8, wherein the second characterized binding affinity comprises a lower probability of binding to the first proteoform compared to the probability of binding to the second proteoform.

11. The method of any one of the preceding clauses, wherein the characterizing the presence or absence of the first proteoform and the second proteoform at each observable address of the array comprises: i. providing the presence or absence of the first detectable signal at each address of the array and the presence or absence of the second detectable signal at each address of the array to a computer-implemented decoding algorithm; and ii. determining a characterization of polypeptide identity at each address of the array using the decoding algorithm, wherein the characterization of polypeptide identity is selected from the group consisting of the first proteoform, the second proteoform, both proteoforms, neither proteoform, and uncertain.

12. The method of clause 11, wherein the determining a characterization of polypeptide identity further comprises determining a confidence interval for the characterization of polypeptide identity.

13. The method of any one of the preceding clauses, wherein one or more of steps b)-e) are repeated.

14. The method of any one of the preceding clauses, further comprising contacting the array with one or more additional affinity reagents comprising a characterized binding affinity.

15. The method of any one of the preceding clauses, further comprising removing the first affinity reagent from the array.

16. The method of any one of the preceding clauses, further comprising removing the second affinity reagent from the array.

17. The method of any one of the preceding clauses, further comprising calculating a quantity of the first proteoform or a quantity of the second proteoform in the array of polypeptides.

18. The method of any one of the preceding clauses, wherein the polypeptide has one or more additional proteoforms.

19. The method of any one of the preceding clauses, wherein the array of polypeptides comprises one or more additional polypeptide species.

20. The method of clause 19, wherein at least one polypeptide species of the one or more additional polypeptide species comprises two or more proteoforms.

21. The method of clause 20, wherein steps b) through f) are repeated for the at least one polypeptide species.

22. The method of clause 21, wherein steps b) through f) are repeated for each polypeptide species comprising two or more proteoforms.

23. The method of any one of clauses 19-21, wherein the one or more additional polypeptide species comprises at least about 10 polypeptide species.

24. The method of clause 22, wherein the one or more additional polypeptide species comprises at least about 100 polypeptide species.

25. The method of clause 23, wherein the one or more additional polypeptide species comprises at least about 1000 polypeptide species.

26. The method of any one of the preceding clauses, wherein the polypeptides of the array of polypeptides are derived from a proteomic sample.

27. The method of clause 26, wherein the proteomic sample comprises a sample derived from a human, domesticated animal, wild animal, domesticated plant, wild plant, engineered microorganism, or natural microorganism.

28. The method of any one of the preceding clauses, wherein the first affinity reagent or the second affinity reagent comprises a characterized binding affinity for a post-translational modification.

29. The method of clause 28, wherein the characterized binding affinity comprises a binding affinity for the post-translational modification that is independent of sequence context.

30. The method of clause 28, wherein the characterized binding affinity comprises a binding affinity for the post-translational modification that is dependent upon sequence context.

31. The method of any one of the preceding clauses, wherein the first detectable label or the second detectable label is selected from the group consisting of a fluorescent label, a luminescent label, a radiolabel, an isotopic label, and a nucleic acid label.

32. The method of clause 30, wherein the first detectable label is the same as the second detectable label.

33. The method of clause 31, wherein the first detectable label is different from the second detectable label.

34. The method of any one of the preceding clauses, wherein the array comprises a solid support and wherein each polypeptide of the array is coupled to an individually observable address on the solid support.

35. The method of clause 34, wherein the solid support comprises a metal, metal oxide, semiconductor, polymer, glass, or ceramic.

36. The method of clause 34 or 35, wherein the solid support comprises a patterned array.

37. The method of any one of clauses 34 or 35, wherein the solid support comprises an non-patterned array.

38. The method of any one of clauses 34-37, wherein each observable address comprises an anchoring group coupled to the array.

39. The method of clause 38, wherein each polypeptide of the array of polypeptides is coupled to the solid support by the anchoring group.

40. The method of clause 39, wherein an anchoring group comprises a single polypeptide of the array of polypeptides.

41. The method of clause 39, wherein an anchoring group comprises two or more polypeptides of the array of polypeptides.

42. The method of any one of clauses 38-41, wherein the anchoring group comprises a structured nucleic acid particle.

43. The method of clause 42, wherein the structured nucleic acid particle comprises a DNA nanoball, a DNA nanotube, or a DNA origami particle.

44. A method, comprising: a) performing the method of any one of clauses 1-42; and b) quantifying proteoforms for at least about 10% of a proteome.

45. The method of clause 44, wherein the quantifying comprises quantifying at least about 50% of a proteome.

46. The method of clause 44, wherein the quantifying comprises quantifying at least about 90% of a proteome.

47. The method of any one of the preceding clauses, wherein the polypeptide comprises a polypeptide complex, wherein the polypeptide complex comprises the polypeptide and a second biomolecule.

48. The method of clause 47, wherein the second biomolecule comprises a second polypeptide, a nucleic acid, a polysaccharide, or a lipid.

49. The method of any one of clauses 1-25 or 28-48, wherein the polypeptides of the array of polypeptides are derived from an environmental source.

50. The method of clause 49, wherein the environmental source comprises a forensic sample, an industrial sample, a consumer product, a geological sample, an archeological sample, a paleontological sample, and an extraterrestrial sample.
51. The method of any one of clauses 1-25 or 28-50, wherein the polypeptides of the array of polypeptides are derived from a population of organisms or a microbiome.
52. A method of characterizing proteoforms, comprising: (a) providing an array, including a plurality of polypeptides, wherein the plurality of polypeptides includes a first polypeptide having a first proteoform and a second polypeptide having a second proteoform and wherein a polypeptide of the plurality of polypeptides is present at an individually observable address of the array; (b) contacting the array with a first affinity reagent and a second affinity reagent, wherein the first affinity reagent is configured to bind to the first proteoform and the second affinity reagent is configured to bind to the second proteoform; (c) detecting signals indicative of the first affinity reagent binding to the first polypeptide and the second affinity reagent binding to the second polypeptide; and (d) using the signals to characterize the first proteoform and the second proteoform.
53. The method of clause 52, wherein the array is contacted with the first affinity reagent and a first signal is detected indicative of the first affinity reagent binding to the first polypeptide; and, wherein subsequently the array is contacted with the second affinity reagent and a second signal is detected indicative of the second affinity reagent binding to the second polypeptide.
54. The method of clause 52, wherein the array is contemporaneously contacted with the first affinity reagent and the second affinity reagent and wherein a first signal is detected indicative of the first affinity reagent binding to the first polypeptide; and a second signal is detected indicative of the second affinity reagent binding to the second polypeptide.
55. The method of clause 52, wherein after the detecting signals indicative of the first affinity reagent binding to the first polypeptide and the second affinity reagent binding to the second polypeptide in step (c), further characterization is performed comprising one or more Edman-type sequencing steps.
56. The method of clause 55, wherein the Edman-type sequencing steps comprise reacting an Edman reagent with at least the first and the second polypeptides to form corresponding first and second Edman complexes.
57. The method of clause 55, wherein step (c) is repeated after reacting an Edman reagent with at least the first and the second polypeptides to form Edman complexes.
58. The method of clause 55, wherein the Edman-type sequencing steps comprise removal of a N-terminal amino acid residue.
59. The method of clause 58, wherein step (c) is repeated after removal of the N-terminal amino acid residue.
60. The method of clause 88, wherein at least one of the first and second Edman complexes include a fluorescent group, a click chemical functionality or a fluorescent group functionality.
61. The method of clause 57, wherein at least one of the first polypeptide and the second polypeptide comprises a post-translational modification covalently connected to an N-terminal amino acid residue.
62. The method of clause 61, wherein the post-translational modification is covalently connected to a N-terminal primary or secondary amino acid group of the N-terminal amino acid residue or is covalently connected to a side chain of the N-terminal amino acid residue, or is dependently or independently covalently connected to both the N-terminal primary or secondary amino group and to the side chain of the N-terminal amino acid residue.
63. The method of clause 62, wherein the post-translational modification covalently connected to the N-terminal amino group is different to the post-translational modification covalently connected to the side chain of the N-terminal amino acid residue.
64. The method of clause 60, wherein the post-translational modification is covalently connected to an amino acid residue wherein substantially different signals indicative of the first affinity reagent binding to the first polypeptide and the second affinity reagent binding to the second polypeptide occur before and after the one or more Edman-type sequencing steps.
65. The method of clause 61, wherein the post-translational modification is a phosphorylated amino acid residue.
66. The method of clause 65, wherein the post-translational modification is a phosphotyrosine, phosphoserine or phosphorthreonine.
67. The method of clause 65, wherein the post-translation modification comprises at least one glycan moieties.
68. The method of clause 52, wherein after the detecting signals indicative of the first affinity reagent binding to the first polypeptide and the second affinity reagent binding to the second polypeptide in step (c), further characterization comprises a dansyl reagent derivatization comprising a detection of a post-translationally modified N-terminal amino acid residue.
69. The method of clause 68, wherein the detection of a N-terminal amino acid residue comprises using immobilized affinity reagents.
70. The method of clause 52, wherein the detecting signals in step (c) comprises detecting fluorescence lifetime (FLT) signals.
71. The method of clause 70, wherein the FLT detection is performed in a frequency domain.
72. The method of clause 70, wherein FLT detection is performed in a time domain.
73. The method of clause 72, wherein at least a portion of a first post-translational modification is removed from the first polypeptide.
74. The method of clause 72, where the first post-translational modification comprises a glycan or a glycan group.
75. The method of clause 73, wherein the glycan or the glycan group is at least partially removed by glycosidase enzymes or chemical regents known to remove the glycan.
76. The method of clause 74, where the first post-translational modification comprises one or more phosphate groups.
77. The method of clause 76, wherein the one or more phosphate groups are removed by de-phosphorylating enzymes or chemical regent.
78. The method of clause 74, wherein the first post-translational modification comprises one or more amino acid residues.
79. The method of clause 74, where the first post-translational modification comprises a cysteine amino acid residue with a free thiol side chain.
80. The method of clause 79, where the first post-translational modification comprises a cysteine thiol amino acid side chain capped by a chemical reagent.
81. The method of clause 80, wherein the chemical reagent is a haloacetamide.
82. The method of clause 52, wherein the detecting signals in step (c) comprises detecting emission signals in a two-photon excitation system comprising an affinity reagent having a reporting fluorophore.

83. The method of clause 52, wherein the detecting signals in step (c) comprises detecting emission signals in an evanescent field system comprising an affinity reagent having a reporting fluorophore.

84. The method of clause 52, wherein a detecting step is performed using optical imaging, total internal reflection fluorescence (TIRF), super-resolution microscopy, structured-light microscopy, widefield microscopy, or confocal microscopy.

85. The method of clause 60, comprising one or more Edman degradation steps.

86. The method of clause 85, wherein one Edman degradation step comprises complexing an N-terminus with an Edman reagent thereby forming an N-terminal Edman complex, followed by removal of the N-terminal Edman complex.

87. The method of clause 86, wherein removal of the N-terminal Edman complex comprises at least one of, heat, change in pH or combinations thereof.

88. The method of clause, 87 wherein at least one affinity reagent is added after forming an N-terminal Edman complex and wherein the at least one affinity reagent binds at least in part to the N-terminal Edman complex.

89. The method of clause 60, wherein the removing the N-terminal amino acid comprises using one or more aminopeptidases.

90. The method of any one of the preceding clauses, wherein the amino acid residues recognized by members in an aptamer library comprise natural amino acids, unnatural amino acid residues, unmodified amino acid residues, and modified amino acid residues.

91. A method of characterizing M proteoforms of a polypeptide, comprising: (a) forming a plurality of first affinity complexes between a plurality of the M polypeptides and a first affinity reagent; (b) detecting a plurality of first reporting signals from the plurality of first affinity complexes; (c) arresting the plurality of first reporting signals; (d) repeating steps (a)-(c) for a second affinity reagent affording a plurality of second reporting signals; and (e) characterizing one or more of the M proteoforms based on a presence or absence of first and second reporting signals.

92. The method of clause 91, wherein each one of the M proteoforms forms an affinity complex with the first affinity reagent or the second affinity reagent but not both first and second affinity reagents.

93. The method of clause 91, wherein each one of a majority of the M proteoforms forms an affinity complex with the first affinity reagent or the second affinity reagent but not both first and second affinity reagents.

94. The method of clause 91, wherein each one of a majority of the M proteoforms forms an affinity complex with the first affinity reagent and the second affinity reagent.

95. A system comprising: at least one hardware processor; and at least one non-transitory computer-readable storage medium storing process or executable instructions that, when executed by the at least one hardware processor, cause the at least one hardware processor to perform the method of any one of clauses 1 through 94.

96. At least one non-transitory computer-readable storage medium storing process or executable instructions that, when executed by at least one hardware processor, cause the at least one hardware processor to perform the method of any one of clauses 1 through 94.

97. A method of characterizing proteoforms of a polypeptide, comprising: (a) providing an array comprising a plurality of polypeptides, wherein the plurality of polypeptides comprises a first proteoform of a polypeptide and a second proteoform of the polypeptide, and wherein each proteoform of the polypeptide is present at an individually observable address on the array; (b) contacting the array with a first affinity reagent and a second affinity reagent, wherein the first affinity reagent binds to the first proteoform and the second affinity reagent binds to the second proteoform, and wherein at least one of the first and second affinity reagents binds promiscuously to the first and second proteoforms of the polypeptide; and (c) detecting the presence or absence of binding of the affinity reagents at the individually observable addresses on the array, thereby characterizing at least one of the proteoforms of the polypeptide.

98. The method of clause 97, wherein each of the first and second affinity reagents comprises a detectable label, and wherein (c) comprises detecting the presence or absence of binding reporter signals from the detectable labels; and analyzing the binding reporter signals thereby characterizing at least one of the proteoforms of a polypeptide in the array.

99. The method of claim 98, wherein detecting the absence of the binding reporter signals from the detectable labels contributes to the characterizing at least one of the proteoforms of the polypeptide.

100. The method of claim 97, wherein the providing an array comprises affixing the plurality of polypeptides to a plurality of sites on the array.

101. The method of claim 97, wherein the detecting further comprises observing the first proteoform at single molecule resolution at a first individually observable address on the array.

102. The method of claim 101, wherein the detecting further comprises observing the second proteoform at single molecule resolution at a second individually observable address on the array.

103. The method of claim 97, wherein the first affinity reagent comprises two or more multiplexed affinity reagents.

104. The method of claim 103, wherein the two or more multiplexed affinity reagents are individually or simultaneously contacted with a plurality of proteoforms.

105. The method of claim 97, wherein at least one affinity reagent binds to 3 or more different proteoforms of the polypeptide in the array.

106. The method of claim 103, wherein at least one proteoform in the array binds to three or more different types of affinity reagents in a first set of affinity reagents.

107. The method of claim 97, wherein the detecting further comprises observing an ensemble of polypeptides comprising the first proteoform at a first individually observable address on the array.

108. The method of claim 107, wherein the detecting further comprises observing an ensemble of polypeptides comprising the second proteoform at a second individually observable address on the array.

109. The method of claim 97, wherein the characterizing at least one of the proteoforms of the polypeptide comprises determining a quality of the proteoform.

110. The method of claim 97, wherein the characterizing at least one of the proteoforms of the polypeptide comprises quantifying the proteoform.

111. The method of claim 97, wherein the characterizing at least one of the proteoforms in the array comprises determining both a quality and quantity of the proteoform.

112. The method of claim 97, wherein step (a) comprises providing a plurality of proteoforms comprising proteoforms of a first polypeptide and proteoforms of a second polypeptide, the plurality of proteoforms being at a plurality of sites in an array.

113. The method of claim 112, wherein step (b) comprises contacting the proteoforms with a first set of affinity reagents, each affinity reagent comprising a detectable label; wherein at least one affinity reagent binds to two or more different types of proteoforms of the first polypeptide and to at least one type of proteoform of the second polypeptide, and wherein at least one type of proteoform of the first polypeptide binds to two or more different types of affinity reagent from the first set of affinity reagents.

114. The method of claim 112, wherein the two or more different proteoforms of the polypeptide and the at least one proteoform of the second polypeptide comprise a common amino acid sequence motif.

115. The method of claim 112, wherein the two or more different proteoforms of the polypeptide and the at least one proteoform of the second polypeptide comprise the same post-translational modification.

116. The method of claim 115, wherein the same post-translational modification is selected from the group consisting of, phosphotyrosine, phosphorthreonine, phosphoserine, deamidation, acetylation, and ubiquitination.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of characterizing proteoforms of a polypeptide, comprising:
    (a) providing an array comprising a plurality of polypeptides, wherein the plurality of polypeptides comprises a first proteoform of a polypeptide and a second proteoform of the polypeptide, wherein each proteoform of the polypeptide is present at an individually observable address on the array, and wherein individual addresses of the array each comprises a single polypeptide of the plurality of polypeptides;
    (b) contacting the array with a first affinity reagent and a second affinity reagent, wherein the first affinity reagent binds to the first proteoform and the second affinity reagent binds to the second proteoform, wherein the first affinity reagent is removed from the array prior to contacting the array with the second affinity reagent, and wherein at least one of the first and second affinity reagents binds promiscuously to the first and second proteoforms of the polypeptide;
    (c) detecting the presence or absence of binding of the affinity reagents at the individually observable addresses on the array, thereby characterizing at least one of the proteoforms of the polypeptide, wherein the detecting further comprises observing the first proteoform at single molecule resolution at a first individually observable address on the array, and wherein the detecting further comprises observing the second proteoform at single molecule resolution at a second individually observable address on the array.

2. The method of claim 1, wherein each of the first and second affinity reagents comprises a detectable label, and wherein (c) comprises detecting the presence or absence of binding reporter signals from the detectable labels; and analyzing the binding reporter signals thereby characterizing at least one of the proteoforms of a polypeptide in the array.

3. The method of claim 2, wherein detecting the absence of the binding reporter signals from the detectable labels contributes to the characterizing at least one of the proteoforms of the polypeptide.

4. The method of claim 1, wherein the providing an array comprises affixing the plurality of polypeptides to a plurality of sites on the array.

5. The method of claim 1, wherein the first affinity reagent comprises two or more multiplexed affinity reagents.

6. The method of claim 5, wherein the two or more multiplexed affinity reagents are individually or simultaneously contacted with a plurality of proteoforms.

7. The method of claim 1, wherein at least one affinity reagent binds to 3 or more different proteoforms of the plurality of the polypeptides in the array.

8. The method of claim 5, wherein at least one proteoform in the array binds to three or more different types of affinity reagents in a first set of affinity reagents.

9. The method of claim 1, wherein the characterizing at least one of the proteoforms of the polypeptide comprises determining a quality of the proteoform.

10. The method of claim 1, wherein the characterizing at least one of the proteoforms of the polypeptide comprises quantifying the proteoform.

11. The method of claim 1, wherein the characterizing at least one of the proteoforms in the array comprises determining both a quality and quantity of the proteoform.

12. The method of claim 1, wherein step (a) comprises providing a plurality of proteoforms comprising proteoforms of a first polypeptide and proteoforms of a second polypeptide, the plurality of proteoforms being at a plurality of sites in an array.

13. The method of claim 12, wherein the proteoforms of the first polypeptide and the proteoforms of the second polypeptide comprise a common amino acid sequence motif.

14. The method of claim 12, wherein the proteoforms of the first polypeptide and the proteoforms of the second polypeptide comprise the same post-translational modification.

15. The method of claim 14, wherein the same post-translational modification is selected from the group consisting of, phosphotyrosine, phosphorthreonine, phosphoserine, deamidation, acetylation, and ubiquitination.

16. The method of claim 1, further comprising treating the array to remove a post-translational modification and repeating steps (b) and (c) using the treated array.

17. The method of claim 16, wherein the treating of the array comprises contacting the array with an enzyme that specifically removes the post-translational modification.

* * * * *